United States Patent
Galen et al.

(10) Patent No.: US 9,446,113 B2
(45) Date of Patent: Sep. 20, 2016

(54) BACTERIAL LIVE VECTOR VACCINES EXPRESSING CHROMOSOMALLY-INTEGRATED FOREIGN ANTIGENS

(71) Applicants: James E. Galen, Eldersburg, MD (US); Jin-Yuan Wang, Silver Spring, MD (US)

(72) Inventors: James E. Galen, Eldersburg, MD (US); Jin-Yuan Wang, Silver Spring, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 14/687,463

(22) Filed: Apr. 15, 2015

(65) Prior Publication Data

US 2015/0216959 A1    Aug. 6, 2015

Related U.S. Application Data

(63) Continuation-in-part of application No. PCT/US2013/064872, filed on Oct. 14, 2013.

(60) Provisional application No. 61/713,806, filed on Oct. 15, 2012.

(51) Int. Cl.
  *A61K 39/08*  (2006.01)
  *C12N 15/74*  (2006.01)
  *A61K 39/02*  (2006.01)
  *A61K 39/00*  (2006.01)

(52) U.S. Cl.
  CPC ........... *A61K 39/08* (2013.01); *A61K 39/0291* (2013.01); *C12N 15/74* (2013.01); *A61K 2039/522* (2013.01); *A61K 2039/523* (2013.01)

(58) Field of Classification Search
  CPC ............. C12N 15/74; A61K 39/0291; A61K 2039/523; A61K 2039/522; A61K 39/08
  See application file for complete search history.

(56) References Cited

U.S. PATENT DOCUMENTS

| | | |
|---|---|---|
| 2008/0233094 A1 | 9/2008 | Vindurampulle et al. |
| 2010/0112674 A1 | 5/2010 | Galen et al. |

FOREIGN PATENT DOCUMENTS

| | | |
|---|---|---|
| WO | 00/32047 | 6/2000 |
| WO | 03/097838 | 11/2003 |
| WO | 2011/060431 | 5/2011 |

OTHER PUBLICATIONS

Galen, J. et al., A new generation of stable, nonantibiotic, low-copy-number plasmids improves immune responses to foreign antigens in *Salmonella enterica* Serovar Typhi live vectors, Infection and Immunity, 2010, vol. 78, No. 1, pp. 337-347.
Galen, J. et al., Mucosal immunization with attenuated Salmonella Typhi expressing anthrax PA83 primes monkeys for accelerated serum antibody responses to parenteral PA83 vaccine, J. Infect. D 24 hr @ 37°C

BACTERIAL LIVE VECTOR VACCINES EXPRESSING CHROMOSOMALLY-INTEGRATED FOREIGN ANTIGENS

STATEMENT OF FEDERALLY SPONSORED RESEARCH AND DEVELOPMENT

This invention was made with government support under Grant Number AI077911 and Grant Number AI095309 awarded by the National Institutes of Health. The government has certain rights in the invention.

TECHNICAL FIELD

The invention generally relates to the provision of live vector vaccines that can be used to vaccinate a subject against bacterial, viral or parasitic pathogens. In particular, the invention relates to bacterial live vector vaccines that express chromosomally-integrated antigen expression cassettes encoding selected antigens, such as protective antigens of unrelated bacterial, viral or parasitic pathogens.

BACKGROUND OF INVENTION

Excellent progress has been made over the past twenty years in the adaptation of attenuated bacterial vaccine strains for expression of foreign antigens to create multivalent live vector vaccines. This has included a devotion of significant effort to the creation of expression technologies which either directly or indirectly address the important problem of metabolic stress often associated with expression of foreign immunogens.[1,2] It is recognized that inappropriate synthesis of high levels of foreign protein in an effort to induce an antigen-specific protective immune response can adversely affect the fitness and growth rate of an already attenuated vaccine strain, resulting in over-attenuation and loss of immunity directed at both the live vector and foreign antigen. If these target immunogens are encoded by multi-copy expression plasmids, these undesirable metabolic fluxes can result in plasmid loss in the absence of selective pressure, which ultimately defeats the strategy of live vector-mediated delivery of vaccine antigens.

Effective genetic stabilization systems have been developed for enhancing the retention of multicopy plasmids encoding regulated synthesis of foreign antigens, without the further requirement to select with antibiotics.[3,4,5] Antigen export systems have also been developed to reduce proteolytic degradation of foreign antigens within the cytoplasm and more effectively deliver these antigens to the immune system to enhance immunogenicity.[6,7,8,9] Thus, a variety of genetic techniques and technologies are now available for efficient delivery of one or more antigens using live vector vaccines. However, significant problems remain associated with this technology. For example inclusion of more than one gene encoding a foreign antigen of interest within a single multicopy plasmid can lead to large plasmids which ultimately prove to be genetically unstable, reducing both antigen synthesis and the ensuing immune responses. [10]

Novel strategies for engineering live vector vaccines to express high levels of a foreign antigen or to express two or more different antigens are needed.

BRIEF SUMMARY OF INVENTION

The present invention is based on a novel strategy of engineering live vector vaccines to have antigen expression cassettes encoding an antigen of interest integrated into two or more different chromosomal locations, and optionally carrying a plasmid-based expression system. Live vector vaccines engineered in this manner can deliver sufficiently immunogenic levels of the chromosomally encoded antigens to a subject. The strategic integration of antigen expression cassettes into multiple locations within the chromosome of the selected live vector results in production of sufficient levels of the encoded antigen, while avoiding adverse effects on the fitness and growth rate of the vector.

In a first embodiment, the invention is directed to an attenuated strain of *Salmonella enterica* serovar *typhi* (hereinafter "*S. typhi*") having disruptions of two or more chromosomal locations selected from the group consisting of the guaBA locus, the htrA locus, the clyA locus, the rpoS locus, and the ssb locus. In one aspect of this embodiment, the attenuated strain of *S. typhi* is the strain CVD 910 which has disruptions of the guaBA locus, the htrA locus, and the rpoS locus.

In a second embodiment, the invention is directed to an antigen-encoding attenuated strain of *S. typhi*, wherein the strain comprises:

(a) disruptions of two or more chromosomal locations, wherein the chromosomal locations are selected from the group consisting of the guaBA locus, the htrA locus, the clyA locus, the rpoS locus, and the ssb locus, and (b) chromosomal-based expression systems integrated into the locations of the chromosomal disruptions, wherein each chromosomal-based expression system comprises an antigen expression cassette encoding an antigen of interest.

In one aspect of this embodiment, the antigen of interest is a protective antigen of, for example, an unrelated bacterial, viral, parasitic, or fungal pathogen. In a particular aspect, the antigen of interest is one or more of the cell binding domain of *C. difficile* toxin A (CBD/A), the cell binding domain of *C. difficile* toxin B (CBD/B), the cell binding domain of *C. difficile* binary toxin (BT), the LcrV antigen of *Yersinia pestis* and the capsular F1 antigen of *Yersinia pestis*. In a further aspect, each chromosomal-based expression system comprises an antigen expression cassette encoding a different antigen of interest.

In another aspect of this embodiment, the antigen-encoding attenuated strain of *S. typhi* is the strain CVD 910 which has disruptions of the guaBA locus, the htrA locus, and the rpoS locus, and which has a chromosomal-based expression system integrated into each site of disruption that encodes one or more antigens of interest. In a particular aspect, the antigen-encoding attenuated strain of *S. typhi* is the strain CVD 910-3A which has disruptions of the guaBA locus, the htrA locus, and the rpoS locus, and which comprises antigen expression cassettes integrated into the locations of chromosomal disruption, wherein each antigen expression cassette encodes the cell binding domain of *C. difficile* toxin A.

In a third embodiment, the invention is directed to an antigen-encoding attenuated strain of *S. typhi*, wherein the strain comprises:

(a) disruptions of two or more chromosomal locations, wherein the chromosomal locations are selected from the group consisting of the guaBA locus, the htrA locus, the clyA locus, the rpoS locus, and the ssb locus, (b) chromosomal-based expression systems integrated into the locations of the chromosomal disruptions, wherein each chromosomal-based expression system comprises an antigen expression cassette encoding an antigen of interest, and (c) one or more plasmid-based expression systems, wherein each plasmid-based expression system encodes an antigen of interest.

In one aspect of this embodiment, the antigens of interest are individually protective antigens of, for example, unrelated bacterial, viral or parasitic pathogens. In a particular aspect, the antigens of interest are individually one or more of the cell binding domain of *C. difficile* toxin A (CBD/A), the cell binding domain of *C. difficile* toxin B (CBD/B), the cell binding domain of *C. difficile* binary toxin (BT), the LcrV antigen of *Yersinia pestis* and the capsular F1 antigen of *Yersinia pestis*. In a further aspect, the antigens of interest are different.

In another aspect of this embodiment, the antigen-encoding attenuated strain of *S. typhi* is the strain CVD 910-3A which has disruptions of the guaBA locus, the htrA locus, and the rpoS locus, and which comprises antigen expression cassettes integrated into the locations of chromosomal disruption, wherein each antigen expression cassette encodes the cell binding domain of *C. difficile* toxin A, a further disruption in the ssb locus, and which has an SSB-stabilized plasmid-based expression system. In a particular aspect, the antigen-encoding attenuated strain of *S. typhi* is the strain CVD 910-3Assb(pSEC10-CBD/B) which has disruptions of the guaBA locus, the htrA locus, and the rpoS locus, and which comprises antigen expression cassettes integrated into the locations of chromosomal disruption, wherein each antigen expression cassette encodes the cell binding domain of *C. difficile* toxin A, a further chromosomal deletion of the ssb locus, and an SSB-stabilized plasmid-based expression system encoding the cell binding domain of *C. difficile* toxin B.

In a fourth embodiment, the invention is directed to an antigen-encoding attenuated strain of *S. typhi*, wherein the strain comprises:

(a) disruptions of four chromosomal locations, wherein the chromosomal locations are selected from the group consisting of the guaBA locus, the htrA locus, the clyA locus, and the rpoS locus, (b) chromosomal-based expression systems integrated into the locations of the chromosomal disruptions, wherein each chromosomal-based expression system comprises an antigen expression cassette encoding an antigen of interest, and (c) a plasmid-based expression system, wherein the plasmid-based expression system encodes an antigen of interest.

The antigens of interest may be the same or different in a single strain, and a single copy or multiple copies of the same antigen can be expressed in a single strain. In one aspect of this embodiment, the antigens of interest are protective antigens of, for example, unrelated bacterial, viral or parasitic pathogens. In a particular aspect, the antigens of interest are one or more of the cell binding domain of *C. difficile* toxin A (CBD/A), the cell binding domain of *C. difficile* toxin B (CBD/B), the cell binding domain of *C. difficile* binary toxin (BT), the LcrV antigen of *Yersinia pestis* and the capsular F1 antigen of *Yersinia pestis*. In a further aspect, the attenuated strain of *S. typhi* expresses three different antigens of interest.

In another aspect of this embodiment, the antigen-encoding attenuated strain of *S. typhi* is the strain CVD 910-3A which has disruptions of the guaBA locus, the htrA locus, the rpoS locus and the clyA locus, and which comprises antigen expression cassettes integrated into the locations of chromosomal disruption, wherein at least one of the antigen expression cassettes encodes the cell binding domain of *C. difficile* toxin A (CBD/A), wherein at least one of the antigen expression cassettes encodes the binary toxin (BT) of *C. difficile*, which has a further disruption in the ssb locus, and which has an SSB-stabilized plasmid-based expression system expressing the cell binding domain of *C. difficile* toxin B (CBD/B). In a particular embodiment, three of the antigen expression cassettes encode the cell binding domain of *C. difficile* toxin A (CBD/A) and one of the antigen expression cassettes encodes the binary toxin (BT) of *C. difficile*. In a further particular embodiment, two of the antigen expression cassettes encode the cell binding domain of *C. difficile* toxin A (CBD/A) and two of the antigen expression cassettes encode the binary toxin (BT) of *C. difficile*.

In a particular aspect, the antigen-encoding attenuated strain of *S. typhi* is the strain CVD 910-3A-GB2ssb (pSEC10-CBD/B) which comprises (i) disruptions of the guaBA locus, the htrA locus, the rpoS locus and the clyA locus, and which comprises antigen expression cassettes integrated into the locations of chromosomal disruption, wherein antigen expression cassette located in guaBA chromosomal disruption encodes the binary toxin (BT) of *C. difficile*, wherein antigen expression cassettes located in htrA, rpoS and clyA chromosomal disruptions encode the cell binding domain of *C. difficile* toxin A (CBD/A), (ii) a disruption in the ssb locus, and (iii) an SSB-stabilized plasmid-based expression system encoding the cell binding domain of *C. difficile* toxin B (CBD/B.

In a fifth embodiment, the invention is directed to a live vector vaccine comprising an antigen-encoding attenuated strain of *S. typhi* as defined herein, and a pharmaceutically-acceptable carrier or diluent.

In a sixth embodiment, the invention is directed to methods of inducing an immune response to an antigen of interest in a subject, comprising administering to a subject an antigen-encoding live vector vaccine as defined herein that expresses an antigen of interest.

In a seventh embodiment, the invention is directed to methods of vaccinating a subject with a protective antigen, comprising administering to a subject an antigen-encoding live vector vaccine as defined herein that expresses a protective antigen.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of use, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 1. Schematic depiction of the strategy for chromosomal integration of the antigen expression cassette $P_{ompC}$- gfpuv, encoding the model fluorescent antigen GFPuv. An osmotically-controlled GFPuv-encoding cassette (tandem white circle and hatched thick arrow) was constructed and linked to an aph marker encoding resistance to kanamycin (shaded thick arrow), flanked by FRT recombination sites (black triangles). The incoming $P_{ompC}$-gfpuv-aph cassette was integrated into the live vector chromosome using the λ Red recombination system, followed by removal of the aph marker using FLP recombinase, to yield the final live vector strain bearing no genes encoding resistance to antibiotics. The bacterial chromosome is represented by 5'-proximal and 3'-terminal darkened rectangles, and the black circle labeled with a "P" represents the wild-type chromosomally-encoded promoter of the deleted target open reading frame (e.g., guaBA or htrA).

Figure 2:
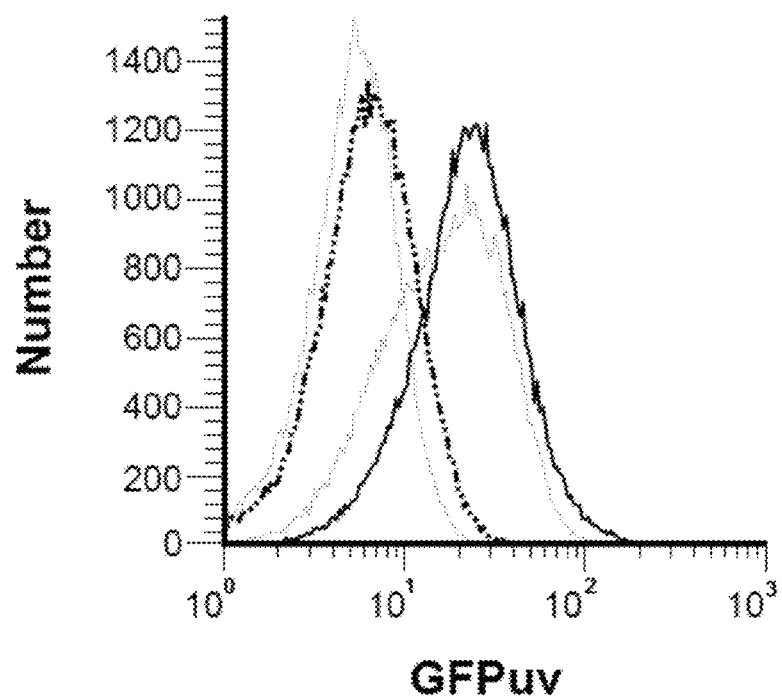

FIG. 2. Flow cytometry histograms of GFPuv-mediated fluorescence encoded by $P_{ompC}$-gfpuv gene cassettes integrated into either the guaBA (thick solid line), htrA (thin hatched line), or clyA (thick broken line) sites of the attenuated S. typhi live vector vaccine candidate CVD 910, compared to the vaccine strain alone (thin dotted line). Fluorescence intensities are measured for individual bacterial cells grown under inducing conditions of 200 mM NaCl in rich medium at 37° C./250 rpm for 16 hr.

Figure 3:
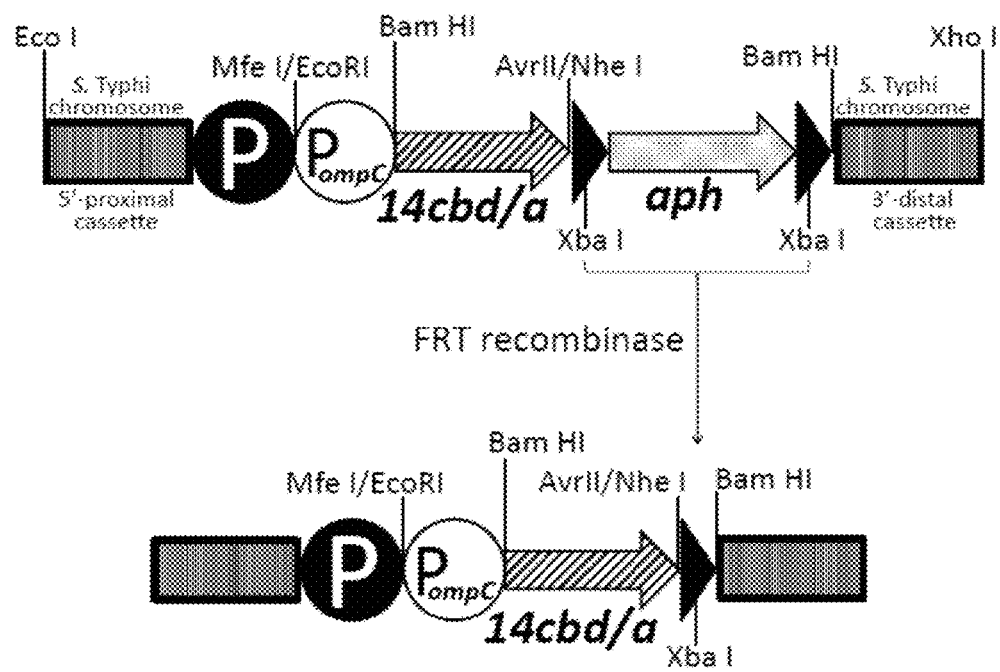

FIG. 3. Schematic depiction of the strategy for chromosomal integration of the cell binding domain from toxin A of C. difficile. A synthetic codon-optimized gene cassette encoding the cell binding domain from toxin A designated 14cbd/a was prepared where the osmotically regulated $P_{ompC}$ promoter was genetically fused to a promoterless 14cbd/a gene (tandem white circle and hatched thick arrow) and linked to an aph marker encoding resistance to kanamycin (shaded thick arrow), flanked by FRT recombination sites (black triangles). The incoming $P_{ompC}$-14cbd/a-aph cassette was integrated into the live vector chromosome using the λ Red recombination system, followed by removal of the aph marker using FLP recombinase, to yield the final live vector strain bearing no genes encoding resistance to antibiotics. The bacterial chromosome is represented by 5'-proximal and 3'-terminal darkened rectangles, and the black circle labeled with a "P" represents the wild-type chromosomally-encoded promoter of the deleted target open reading frame (e.g., guaBA, htrA or rpoS).

Figure 4:
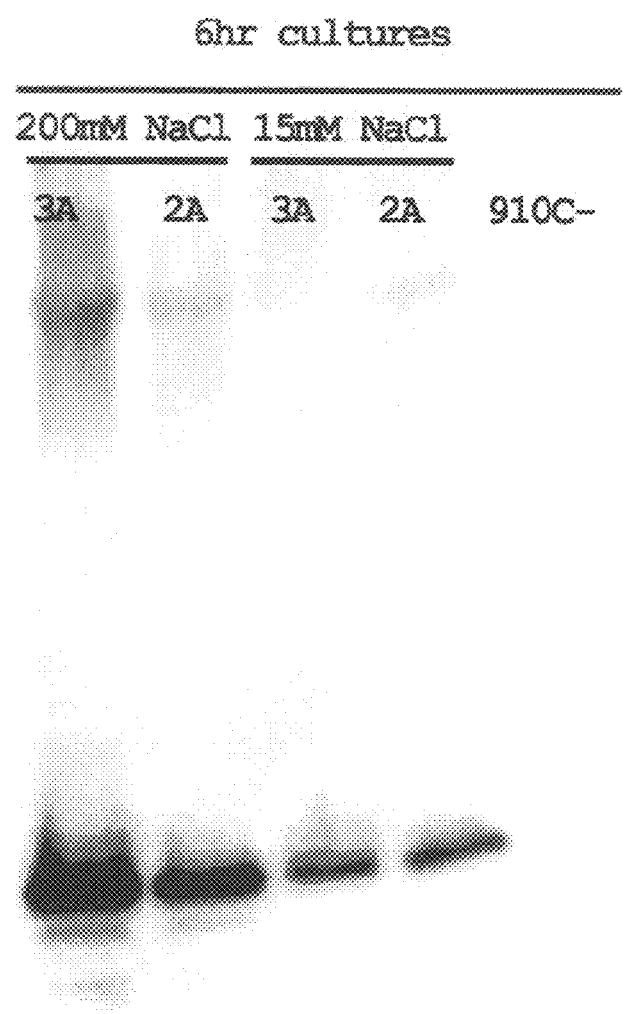

FIG. 4. Western immunoblot analysis. Six hour liquid broth cultures of CVD 910-2A ("2A") were compared to cultures of CVD 910-3A ("3A") under either inducing (200 mM NaCl to activate $P_{ompC}$) or non-inducing (15 mM NaCl) conditions.

Figure 5:
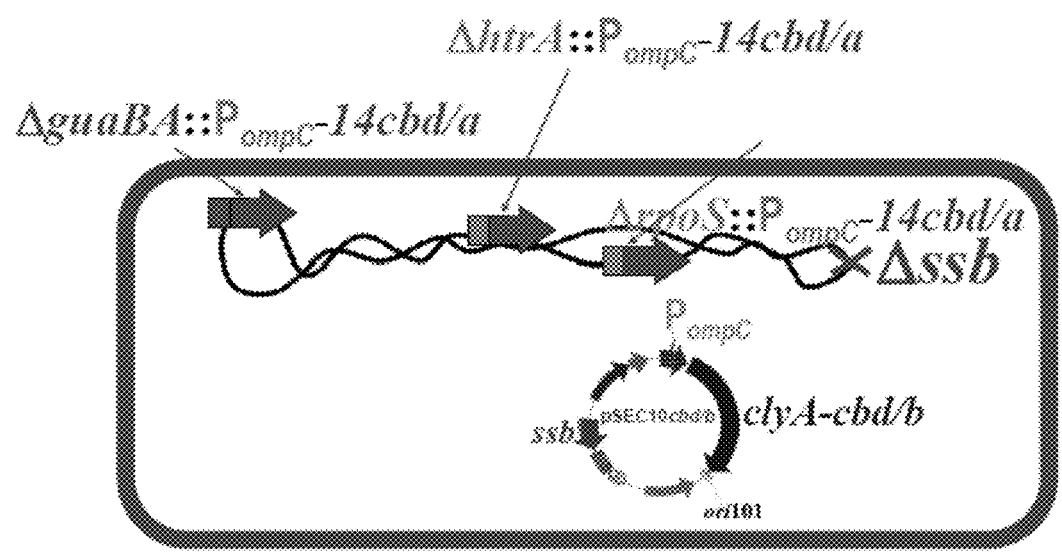

FIG. 5. Schematical depiction of live vaccine strain CVD 910-3Assb(pSEC10-CBD/B).

Figure 6:
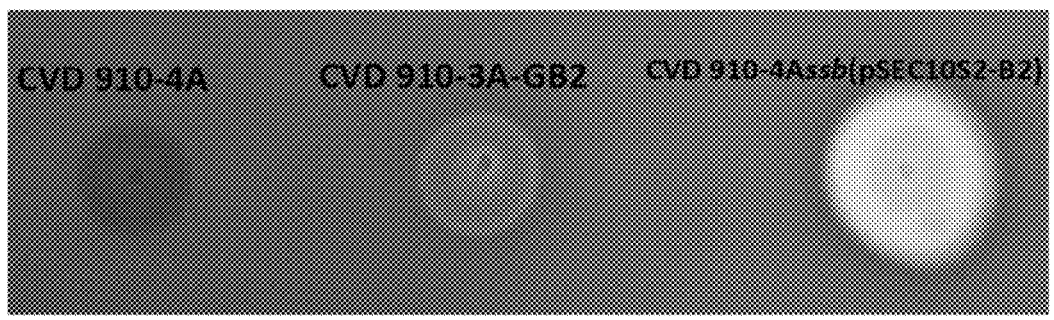

FIG. 6. Comparison of hemolytic activity of fusion proteins expressed in CVD 910-4A, CVD 910-3A-GB2 and CVD 910-4Assb(pSEC10S2-B2). The noted strains were grown on trypticase soy agar with 5% sheep red blood cells under conditions of incubation at 37° C. for 24 hours. The plates were then photographed without magnification.

Figure 7:
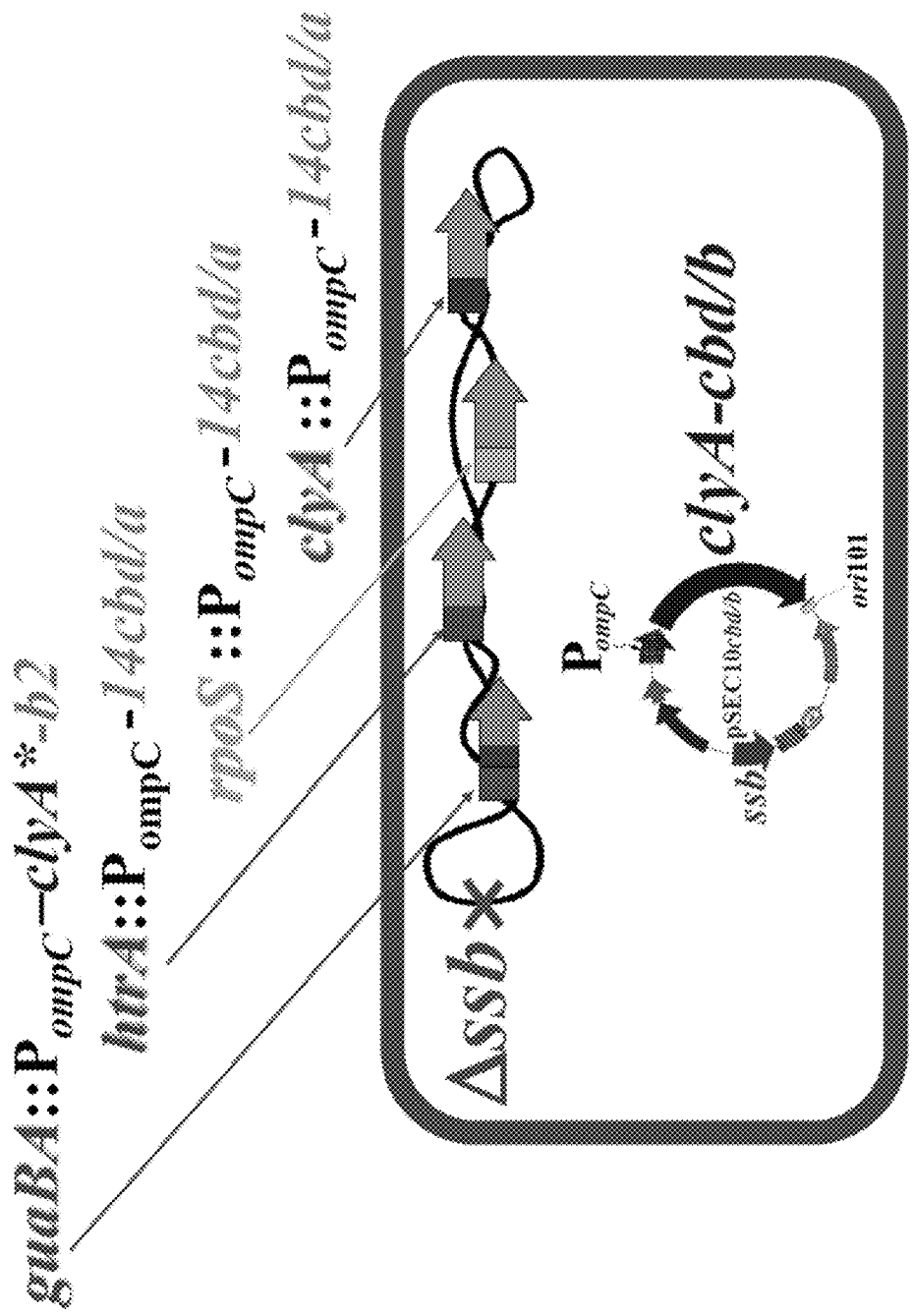

FIG. 7. Schematical depiction of live vaccine strain CVD 910-3A-GB2ssb (pSEC10-CBD/B) which contains insertions into the guaBA, htrA, rpoS and clyA loci and carries the plasmid pSEC10-CBD/B.

DETAILED DESCRIPTION OF THE INVENTION

I. Definitions

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Live vectors engineered for delivery of foreign antigens to the host immune system have performed well in experimental animal models, but have been only modestly successful in clinical trials.[20] Given the advances in the development of powerful plasmid-based expression technologies designed to deliver ample levels of foreign protein, it is unlikely that the lack of antigen-specific immunity observed in clinical trials is due to insufficient antigen synthesis following immunization. To the contrary, it is likely that inappropriate antigen synthesis occurring in vivo results in sufficient shock to the metabolism of the live vector to over-attenuate the strain and destroy immunogenicity. Although various attempts have been made to control the timing of foreign protein synthesis, using tightly regulated promoters to control transcription of genes in response to host environmental signals for example, improved immunogenicity in animals has not translated into improvements in clinical trials.[12,21,22]

A novel and elegant solution to this dilemma is presented here, wherein over-attenuation is circumvented by linking antigen synthesis to the growth rate of the live vector vaccine, such that synthesis is initially low after immunization, but steadily increases as the vaccine strain adjusts to prevailing environmental conditions and undergoes limited replication within the host. This expression strategy allows for efficient expression of one or even multiple foreign antigens within a single live vector vaccine strain. It can also be used in conjunction with plasmid-based methods by distributing the location of antigen expression cassettes between the chromosome and an expression plasmid. The approach presented herein thus offers the flexibility of independently adjusting the copy number of potentially toxic foreign genes by integrating a designated number of copies into the chromosome. By appropriate integration of foreign genes into chromosomal loci whose induction of expression is intimately associated with the physiology and growth rate of the vaccine strain, it becomes possible to "tune" foreign antigen synthesis to the metabolic state of the live vector.

The present invention is therefore based on the discovery that delivery of sufficiently immunogenic levels of chromosomally-encoded antigens to a subject can be accomplished through strategic integration of antigen expression cassettes into multiple locations within the live vector chromosome, thereby compensating for loss of copy number afforded by systems using stable low copy plasmids, while avoiding further attenuation of the vaccine strain. Integration of multiple cassettes also avoids the need for strong constitutive promoters to enhance antigen synthesis from a single gene copy, an approach which does not necessarily lead to adequate antigen synthesis or immune responses.[11,12]

The present invention is directed to several related embodiments, including (i) an attenuated strain of *S. typhi* having disruptions of two or more chromosomal locations selected from the group consisting of the guaBA locus, the htrA locus, the clyA locus, the rpoS locus, and the ssb locus, and (ii) antigen-expressing attenuated strains of *S. typhi* having a chromosomal-based expression system which comprises an antigen expression cassette integrated into two or more locations of chromosomal disruptions, (iii) antigen-expressing attenuated strains of *S. typhi* having a chromosomal-based expression system which comprises an antigen expression cassette integrated into two or more locations of chromosomal disruptions as well as a plasmid-based expression system, (iv) a live vector vaccine comprising an antigen-expressing attenuated strain of *S. typhi* as defined herein, and a pharmaceutically-acceptable carrier or diluent, (v) methods of inducing immune responses to an antigen of interest in a subject using the live vector vaccines as defined herein, and (vi) methods of vaccinating a subject using the live vector vaccines as defined herein.

Attenuated Strains of *S. typhi*

As suggested above, in one embodiment the present invention is directed to attenuated strains of *Salmonella enterica* serovar *typhi* having disruptions of two or more chromosomal locations. *S. typhi* is a well-tolerated live vector that can deliver multiple unrelated immunogenic antigens to the human immune system. *S. typhi* live vectors have been shown to elicit antibodies and a cellular immune response to an expressed antigen. *S. typhi* is characterized by enteric routes of infection, a quality which permits oral vaccine delivery. *S. typhi* also infects monocytes and macrophages and can therefore target antigens to professional APCs.

The genetic disruptions are sufficiently extensive to ensure that active forms of the protein(s) encoded by the locus harboring the disruption are not produced by the bacteria. While the skilled artisan will understand that the characteristics and scope of the disruptions can vary widely, in one non-limiting aspect the disruptions are sufficiently extensive to ensure that neither the protein(s) encoded by the locus, nor fragments thereof, can be detected in bacteria having the disruptions.

The skilled artisan will recognize that strains of bacteria having the disruptions can be readily produced via several techniques known in the art, including the λ Red-mediated site-directed mutagenesis method. [16] Other, less efficient, chromosomal deletion/integration technologies used in the past involve the use of suicide plasmids. These suicide plasmids exhibit replication which is exclusively dependent on the pir protein; successful deletions/integrations are dependent on recA-mediated homologous chromosomal crossovers, and counter-selection with sacB. [29]

The chromosomal locations having the two or more disruptions are the guaBA locus, the htrA locus, the clyA locus, the rpoS locus, and the ssb locus. The disruptions of these loci can be disruptions of the endogenous coding sequences, non-coding control sequence, promoter sequences, or a combination thereof. In the case of the guaBA locus, for example, the coding region can be disrupted without damaging the promoter sequence for the loci.

The chromosomal disruptions can include any combination of deletions or insertions of sequences comprising the disrupted loci.

The attenuated strains of *S. typhi* may have disruptions in any combination of two, three or four of the loci and sites, or even all five of the loci.

Specific examples of such attenuated strains of *S. typhi* including strain CVD 910, which contains disruptions in the guaBA locus and the htrA locus. Because the parent Ty2 strain used in the production of CVD 910 has the rpoS locus naturally inactivated, CVD 910 also contains a disruption of the rpoS locus. Thus, CVD 910 contains disruptions in three chromosomal locations: the guaBA locus, the htrA locus, and the rpoS locus.

Antigen-Encoding Attenuated Strains of *S. typhi*

As suggested above, in a related embodiment the invention is directed to antigen-encoding attenuated strains of *S. typhi* having a chromosomal-based expression system integrated into two or more of the disrupted chromosomal locations within the bacteria. Thus, the invention includes the attenuated strains of *S. typhi* as defined herein, including strain CVD 910, which have been engineered to have antigen expression cassettes integrated into the locations of chromosomal disruptions.

The chromosomal-based expression systems used in the antigen-encoding attenuated strains of *S. typhi* are simple in nature in that they comprises a genetic cassette (antigen expression cassette) comprising the coding sequence of an antigen of interest and, optionally, an exogenous promoter to direct transcription of the coding sequence. In some circumstances and depending on the identity of the coding sequence and/or promoter, additional 5' and/or 3' non-coding sequence associated with the coding sequence of the antigen of interest can be included in the cassette. Together, these sequences make up an antigen expression cassette that can be inserted into one or more disrupted bacterial chromosomes. Because the attenuated strains of *S. typhi* defined herein have at least two chromosomal disruptions, antigen expression cassettes encoding different antigens can be used in the same strain of bacteria. In those strains of *S. typhi* having three chromosomal disruptions, up to three different antigens may be expressed, with up to four different antigens in those strains of *S. typhi* having four chromosomal disruptions, and up to five different antigens in those strains of *S. typhi* having five chromosomal disruptions. The skilled artisan will also recognize that different combinations of antigens can be expressed in a given strain depending on the number of disruptions and the selected antigen expression cassettes. For example, where a strain has three disruptions, the same antigen expression cassette (encoding antigen A, for example) can be inserted into each of the three sites. Alternatively, an antigen expression cassette encoding antigen A could be inserted into two of the sites, while an antigen expression cassette encoding antigen B could be inserted into the third site. In a further alternative, an antigen expression cassette encoding antigen A could be inserted into one of the sites, an antigen expression cassette encoding antigen B could be inserted into the second site, and an antigen expression cassette encoding antigen C could be inserted into the third site. Thus, the identity of the antigen encoded by each antigen expression cassette is individually selected and any combination of antigens may be used. This expressly includes instances where a particular antigen is encoded by two or more cassettes as well as instances where a particular antigen is encoded by only one cassette.

Antigens

The antigen expression cassettes of the present invention preferably express an antigen for presentation to a host to elicit an immune response resulting in immunization and protection from disease. The antigens of interest that may be expressed in the attenuated strains of *S. typhi* of the present invention are unlimited in identity and include, but are not limited to, antigens from foreign bacteria (e.g., proteins not already expressed by *S. typhi*), viruses, and parasitic organisms. Exemplary antigens are protective antigens (i.e., an antigen that when bound by an antibody, result in the death of the organism expressing the antigen). Because the attenuated strains of *S. typhi* may be used as live vector vaccines, one practicing the invention will be motivated, in one aspect, to use antigens suspected of or known to induce a protective immune response in a subject. As another example, antigens suspected of or known to induce an active immune response in a subject to pre-existing infection may also be used.

Exemplary antigens that can be used to induce a protective immune response include detoxified versions of enterotoxin A (TcdA), enterotoxin B (TcdB), and binary toxin (transferase; Cdt) of *Clostridium difficile*, and fragments thereof, such as the cell-binding domains of TcdA and TcdB, and the binding domain of Cdt (CdtB). These antigens can be used to produce a mono-, bi- or multivalent live vector vaccine that in turn can be used to vaccinate a subject against infections caused by *C. difficile*. With the ability to impart immunity that recognizes both toxins and putative colonization factors, a subject can be vaccinated against disease that occurs at two critical stages of infection—colonization and toxin production.

Additional exemplary antigens include the LcrV antigen and the capsular F1 antigen of *Yersinia pestis*, which are required for secretion of virulence effectors proteins and are virulence factors themselves. Additional *Yersinia pestis* antigens include pH 6 antigen (Psa), a putative colonization factor, and Yop B/YopD, two essential proteins comprising the translocon region of the type 3 secretion (T3SS) needle.

Given the ease with which antigen expression cassettes can be produced, and the straightforwardness of inserting and removing the cassettes from locations of chromosomal disruptions in bacteria, it will be clear to the skilled artisan that a very wide range of different antigens can be expressed using the chromosomal-based expression systems of the attenuated strains of *S. typhi* defined herein. These same antigens can also be expressed in the bacteria using the plasmid-based expression systems discussed below.

Plasmid-Based Expression Systems

In a related embodiment, the invention is also directed to antigen-encoding attenuated strains of *S. typhi* having the chromosomal-based expression system discussed above, as well as a plasmid-based expression system. The inclusion of a plasmid-based expression system within the bacteria provides additional flexibility for expressing antigens of interest in the attenuated strains of *S. typhi* of the invention. The plasmid-based expression system allows expression of additional copies of an antigen expression cassette that is integrated into the bacterial chromosome or an antigen expression cassette encoding an antigen of different identity. Thus, as defined herein the antigen expression cassettes can be inserted to both the locations of chromosomal disruptions (in terms of the chromosomal-based expression systems) and expression plasmids (in terms of the plasmid-based expression systems).

SSB-Stabilized Plasmid-Based Expression System

Examples include the plasmid-based expression systems disclosed in U.S. Pat. Nos. 6,703,233, 6,969,513, 6,977,176, 7,141,408, 7,125,720 and 7,138,112, each of which is incorporated herein by reference in their entirety. The systems described in these patents are multicopy expression plasmids into which plasmid maintenance systems have been incorporated. Such multicopy expression plasmids produce a gene dosage effect which enhances the level of expression of the antigen of interest. In a specific example, a plasmid-based expression system has been developed in which a low copy expression plasmid has been engineered to encode an essential single-stranded binding protein (SSB) which has been deleted from the bacterial vaccine strain. Since SSB is essential for DNA replication, recombination, and repair, ssb-deleted bacteria must maintain the expression plasmid to enable survival. Therefore, if SSB-stabilized plasmids are used to encode one or more foreign antigens, then bacteria become committed to foreign antigen synthesis. If expression of foreign antigens in the cytoplasm of the bacteria becomes toxic, antigen export systems can be further introduced into these SSB-stabilized plasmids to export fusion proteins out of the cytoplasm and minimize metabolic disruption.

ClyA Fusion Protein Plasmid-Based Expression Systems

A further example of a suitable plasmid-based expression system is disclosed in WO 09/149083, incorporated herein by reference in its entirety, which makes use of the *S. typhi* HlyE family of export proteins, including the cryptic hemolysin (ClyA), encoded by the cytolysin A gene (clyA). ClyA from *S. typhi* was first described by Wallace et al. who also reported the crystal structure for the homologous hemolysin from *E. coli*. [26] This hemolysin has been described previously and variously referred to as ClyA, HlyE, or SheA.

The crystal structure of ClyA in *E. coli* has been resolved. [26] The unique structure can be roughly divided into several domains, a head domain, a body domain and a tail domain. The body domain consists of a bundle of helixes (A, B, C, D, F). The tail domain is a helix G which extends to half the length of the body. The head domain consists of a short β hairpin (β-tongue) and two small helices (D and E), each flanking the β-tongue. It was suggested that the β-tongue might be critical for pore formation and hence for the hemolytic activity. [26] Through site directed mutagenesis, it was found that many regions of ClyA were important for the hemolytic activity. [27]

The ClyA protein is exported from both *E. coli* and *S. typhi* and it is capable of exporting passenger proteins (and antigens of interest) that have been genetically fused to the 3'-terminus of the clyA open reading frame. It is demonstrated that the proper folding of these fusion proteins occurs such that the inherent biological activity of the domains involved is maintained.

The amino acid and nucleotide sequence for the isolated *S. typhi* clyA gene and ClyA protein (from *Salmonella* serovar *typhi* strain Ty2) are provided as SEQ ID NO:39 and SEQ ID NO:38, respectively. A synthetic codon-optimized version of the *S. typhi* clyA gene, as described and utilized herein, is provided in SEQ ID NO:40. Other HlyE family members that may be utilized as export proteins herein are also available and known to those of ordinary skill in the art. The family members include a second *S. typhi* cytolysin A (the clyA gene is set forth in SEQ ID NO:41 and it is available under GENBANK Accession No. AJ313034); *Salmonella paratyphi* cytolysin A (the clyA gene sequence for cytolysin A is set forth in SEQ ID NO:42 and it is available under GENBANK Accession No. AJ313033); *Shigella flexneri* truncated HlyE (the hlyE gene sequence is set forth in SEQ ID NO:43 and it is available under GENBANK Accession No. AF200955); *Escherichia coli* HlyE (the hlyE gene sequence is set forth in SEQ ID NO:44 and it is available under GENBANK Accession No. AJ001829).

As indicated above, the HlyE family of proteins typically causes cytolysis of target cells, including hemolysis of erythrocytes. Because cytolysins/hemolysins may be considered to be virulence factors, the present invention encompasses the use of variants of HlyE family members that have been mutated such that they lack, or have reduced, hemolytic activity. The ability of these variants to be exported from a bacterial cell producing them, alone or in the context of fusion to a protein of interest, has been maintained. Thus, the non-hemolytic variants of HlyE family members have reduced or no hemolytic activity, and yet are fully functional in the plasmid-based expression systems of the present invention. Such variants include the *S. typhi* cytolysin A (ClyA) protein of SEQ ID NO:38 having a single mutation selected from the group consisting of an S195N mutation, an I198N mutation, an A199D mutation, an E204K mutation, and a C285W mutation; an I198N, C285W double mutation; and an I198N, A199D, E204K triple mutation. The *S. typhi* cytolysin A (ClyA) protein may also have the amino acid sequence set forth in SEQ ID NO:38 and a C285W mutation, as well as one additional mutation selected from the group consisting of an I198N mutation, an A199D mutation, and an E204K mutation.

The plasmid-based expression systems comprising ClyA fusion proteins described herein can be used to express and export a wide variety of fusion proteins comprising an export protein and an antigen of interest. The export protein::antigen of interest fusion protein construct is present in an antigen expression cassette, which in turn is present in an expression plasmid to facilitate the recombinant production of the protein of interest. Typically the expression plasmid will comprise an origin of replication and other structural features that control and regulate the maintenance of the expression plasmid in the host cell. Exemplary expression plasmids are well known to the skilled artisan.[7,23,28] The key aspect of such expression plasmids is copy number, which can range from several hundred per chromosomal equivalent to one per chromosomal equivalent. Preferably the copy number of the expression plasmids is between 5 and 15 copies per chromosomal equivalent.

Live Vector Vaccines

As suggested above, and in a related embodiment, the invention is directed to a live vector vaccine comprising one or more of the antigen-encoding attenuated strains of *S. typhi* as defined herein, and a pharmaceutically-acceptable carrier or diluent.

It is contemplated that the live vector vaccines of the present invention will be administered as pharmaceutical formulations for use in vaccination of individuals, preferably humans. In addition to the strains of *S. typhi*, the vaccines will thus include pharmaceutically-acceptable carriers, and optionally, may include other therapeutic ingredients, such as various adjuvants known in the art.

The carrier or carriers must be pharmaceutically acceptable in the sense that they are compatible with the therapeutic ingredients and are not unduly deleterious to the recipient thereof. The therapeutic ingredient or ingredients are provided in an amount and frequency necessary to achieve the desired immunological effect.

The mode of administration and dosage forms will affect the therapeutic amounts of the compounds which are desirable and efficacious for the vaccination application. However, the live vector vaccines are delivered in an amount capable of eliciting an immune reaction in which it is effective to increase the subject's immune response to the antigen(s) of interest. An immunogenic amount is an amount which confers an increased ability to prevent, delay or reduce the severity of the onset of a disease, as compared to such abilities in the absence of such immunization. It will be readily apparent to one of skill in the art that this amount will vary based on factors such as the weight and health of the recipient, the type of antigen(s) being expressed, the type of infecting organism being combatted, and the mode of administration of the vaccines.

The vaccines may be formulated for any suitable means and/or methods for delivering the live vector vaccines to a corporeal locus of the subject where the live vector vaccines are intended to be effective in triggering an immune response, for example, for oral, sublingual, intranasal, intraocular, rectal, transdermal, mucosal, pulmonary, topical or parenteral administration. Parenteral modes of administration include without limitation, intradermal, subcutaneous (s.c., s.q., sub-Q, Hypo), and intramuscular (i.m.). Any known device useful for parenteral injection or infusion of vaccine formulations can be used to effect such administration. In preferred aspects of each of the embodiments on the invention, the vaccines are administered to a subject as an oral formulation, in particular, to the oral mucosa.

The dose rate and suitable dosage forms for the live vector vaccines of the present invention may be readily determined by those of ordinary skill in the art without undue experimentation, by use of conventional antibody titer determination techniques and conventional bioefficacy/biocompatibility protocols. Among other things, the dose rate and suitable dosage forms depend on the particular antigen employed, the desired therapeutic effect, and the desired time span of bioactivity.

Formulations of the vaccines can be presented, for example, as discrete units such as capsules, cachets, tablets or lozenges, each containing a predetermined amount of the vaccine; or as a suspension.

Depending on the means of administration, the vaccines may be administered all at once, such as with an oral formulation in a capsule or liquid, or slowly over a period of time, such as with an intramuscular or intravenous administration. The vaccines may also be administered to the subject more than once, as boosters, for example, where administration of separate doses of the vaccines may be separated in time by hours, days, weeks or months.

In each embodiment and aspect of the invention, the subject is a human, a non-human primate, bird, horse, cow, goat, sheep, a companion animal, such as a dog, cat or rodent, or other mammal.

Manners of Use

As indicated above, it is intended that the antigen-encoding attenuated strains of *S. typhi* defined herein will be grown under conditions that may induce expression of the antigens of interest prior to immunization, and formulated as a live vector vaccine for administration to a subject, whereupon an immune response to the antigens of interest, inter alia, will be induced in the subject.

The invention therefore includes methods of inducing an immune response to an antigen of interest in a subject, comprising administering to a subject a live vector vaccine as defined herein and that expresses an antigen of interest. The invention also includes methods of vaccinating a subject with a protective antigen, comprising administering to a subject a live vector vaccine as defined herein that expresses a protective antigen.

The methods contemplate and include administering the live vector vaccine to the subject only once, or more than once, such as 2, 3, 4, 5 or more times.

A non-limiting example of the manner in which the vaccines may be used includes use of the vaccine as a nosocomial oral vaccine, administered to patients seven days after antibiotic treatment for *Clostridium difficile* infection (CDI) to block recurrent disease by eliciting a vigorous and rapid anamnestic response in patients primed by the initial *C. difficile* infection.

IV. Examples

Materials and Methods

Bacterial Strains and Culture Conditions.

The attenuated *S. enterica* serovar *typhi* (*S. typhi*) live vector vaccine strain CVD 910 used in these studies is an auxotrophic derivative of wild-type strain Ty2, with deletions in guaBA and htrA. To improve the clinical acceptability of the live vector vaccine strains, all genetic and bacteriologic manipulations of the live vectors were performed using an animal product-free medium equivalent to Luria-Bertani medium, comprised of 10 g/liter of Soytone (Teknova; S9052), 5 g/liter Hy-Yest 412 (Sigma; Y1001), and 3 g/liter NaCl (American Bioanalytical; AB01915), supplemented with 0.002% guanine (Sigma; G6779).

Construction of Chromosomal Integrations.

Deletion cassettes were constructed for use with the λ Red-mediated site-directed mutagenesis method [16] to delete either guaBA, htrA, or clyA from wild-type *S. typhi* Ty2. Cassettes encoding upstream and downstream flanking chromosomal sequences were constructed using primer pairs listed in Table 1 and purified chromosomal DNA from Ty2 as the template DNA.

TABLE 1

Primers used in the construction and testing of live vector strains expressing chromosomally-encoded GFPuv.

| Primer (SEQ ID NO:) | Sequence[a] |
|---|---|
| 5guaBA-for SEQ ID NO: 1 | 5'-<u>GAATTC</u>TAGCTGCTCATACTTCTGCTGCA-3' |
| 5guaBA-rev SEQ ID NO: 2 | 5'-<u>GCTAGC</u>CAATTGGGGCAATATCTCACCTGG-3' |
| 3guaBA-for SEQ ID NO: 3 | 5'-<u>GGATCC</u>ACTAGTGTCGATAACCCTTCCTGT GT-3' |
| 3guaBA-rev SEQ ID NO: 4 | 5'-<u>CTCGAG</u>ACAGCACCTACAAGTCTGGCATG-3' |
| guaBA PCR-for SEQ ID NO: 5 | 5'-GCGCTGACCACCGGAATACGGCTG-3' |
| guaBA PCR-rev SEQ ID NO: 6 | 5'-CATGGCATGGATGAGGCAACCGCAAGC-3' |
| 5htrA-for SEQ ID NO: 7 | 5'-<u>GAATTC</u>GTACCTTCAATCAGGCGTTACTGGAA GATG-3' |
| 5htrA-rev SEQ ID NO: 8 | 5'-<u>GCTAGC</u>CAATTGCGATTAACAGGTAACGCAAAAT TGCTGTGTACGTCAG-3' |

TABLE 1-continued

Primers used in the construction and testing of live vector strains expressing chromosomally-encoded GFPuv.

| Primer (SEQ ID NO:) | Sequence[a] |
|---|---|
| 3htrA-for SEQ ID NO: 9 | 5'-<u>GGATCC</u>ACTAGTCTGCGTAAGATTCTCGACAGCA AGCCGTCGGT-3' |
| 3htrA-rev SEQ ID NO: 10 | 5'-<u>CTCGAG</u>CCAGCATCATTTCGGCAGTCATACACA CCAGTTCGC-3' |
| htrA PCR-for SEQ ID NO: 11 | 5'-GTGTCGCCGATCTTGAAGACGCGGTAGAG-3' |
| htrA PCR-rev SEQ ID NO: 12 | 5'-CTATCGACGCCAAGCTGGCCGCTGTCGAC-3' |
| 5clyA-for SEQ ID NO: 13 | 5'-TAGTAATGA<u>GAATTC</u>GCTGGTATTGATCGGCT CTCCGGTAGAGATTAGCGA-3' |
| 5clyA-rev SEQ ID NO: 14 | 5'-<u>GCTAGC</u>CAATTGTGCCTCTTTAAATATATAAA TTGCAATTAAGTACCTG-3' |
| 3clyA-for SEQ ID NO: 15 | 5'-<u>GGATCC</u>ACTAGTGATACATTTTCATTCGATCT GTGTACTTTTAACGCCCGATAGCG-3' |
| 3clyA-rev SEQ ID NO: 16 | 5'-TGATAGTAA<u>CTCGAG</u>ACAATCCATAAGAAAGGT CAGGCACACTGGGAAGGCGACATC-3' |
| clyA PCR-for SEQ ID NO: 17 | 5'-CATGATGGTATCCAGTATGGCACAAGC-3' |
| clyA PCR-rev SEQ ID NO: 18 | 5'-GTAATCGACAACATGCTACATCCATCG-3' |
| 5FRT-aph-for SEQ ID NO: 19 | 5'-<u>GAATTCGCTAGC</u>GCTGGAGCTGCTTCGAAGT TC-3' |
| 3FRT-aph-rev SEQ ID NO: 20 | 5'-<u>CTCGAGTTCCGGGGATCC</u>GTCGACCTGCAGT TC-3' |
| 5gfpuv SEQ ID NO: 21 | 5'-<u>CAATTG</u>TGTGGTAGCACAGAATAATGAAA GT-3' |
| 3gfpuv SEQ ID NO: 22 | 5'-<u>GCTAGC</u>TCATTATTTGTAGAGCTCATCCAT-3' |

[a]Relevant restriction sites are underlined.

Figure 1:
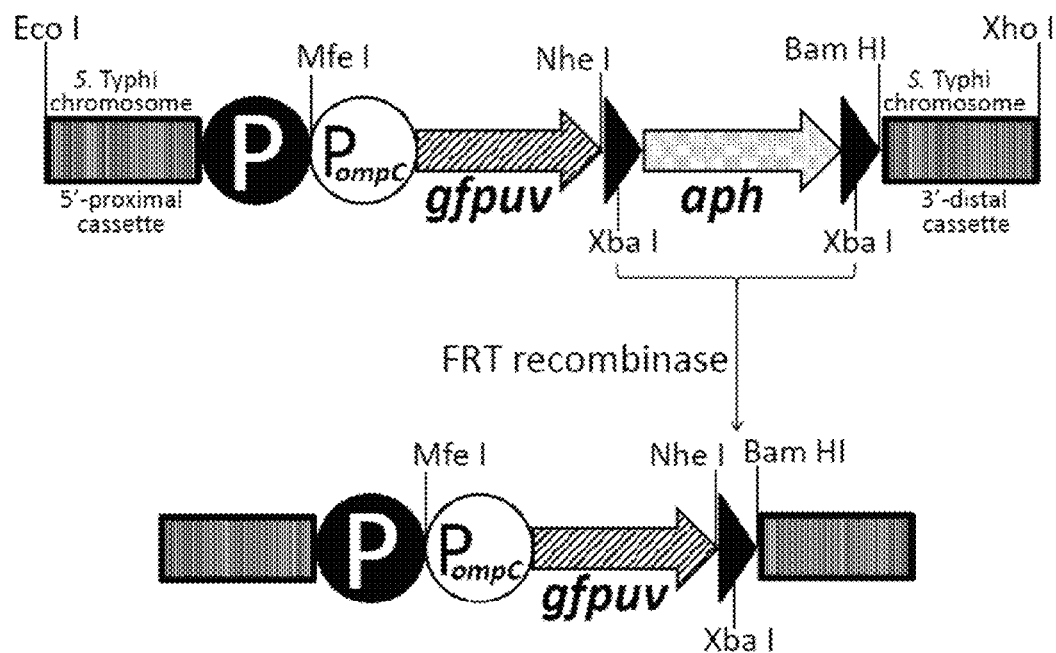

These cassettes were used to exchange chromosomal targets with a Tn5 neomycin phosphotransferase cassette (aph), encoding resistance to kanamycin, and recombined into the chromosome using the λ Red recombination system encoded by pKD46. Final removal of the kanamycin resistance cassette was accomplished using FLP recombinase encoded by pCP20. The integrity of the intended chromosomal deletion mutations was confirmed by DNA sequence analysis of the chromosomal locus from each strain using PCR primers listed in Table 3. For chromosomal expression of GFPuv, an antigen expression cassette in which an osmotically regulated ompC promoter ($P_{ompC}$ [23]) was linked to gfpuv was selected and inserted 5'-proximal to the aph resistance marker of chromosomal deletion cassettes. As shown in FIG. 1, care was taken to preserve the natural chromosomal promoters controlling transcription of chromosomally encoded targets, with the intent that synthesis of GFPuv would ultimately be controlled both by osmolarity (via $P_{ompC}$) as well as growth rate in the case of the guaBA locus,[15] heat shock/environmental stress in the case of the htrA locus,[18] or possibly low pH for clyA.[19]

Flow Cytometry.

GFPuv-expressing strains were grown overnight at 37° C. on rich solid medium supplemented with guanine. 2-3 fluorescing colonies were then inoculated into 20 ml of supplemented liquid medium and incubated with shaking at 250 rpm overnight at 37° C. Overnight starter cultures were then diluted 1:100 into fresh supplemented liquid medium and incubated at 37° C., 250 rpm. For growth curve studies, 5 ml volumes were periodically removed from incubating cultures, from which bacteria from 4 ml were pelleted, while the remaining 1 ml volume was used to measure the optical density at 600 nm ($OD_{600}$). Pelleted bacteria were resuspended in 1 ml of PBS, and cells then diluted 1:1,000 in PBS prior flow analysis. Quantitation of GFPuv fluorescence was analyzed using a MoFlo Legacy flow cytometer/cell sorter system (Beckman Coulter) with the argon laser exciting bacteria at 488 nm and emissions detected at 525 nm. Forward versus side light scatter, measured with logarithmic amplifiers, was used to gate on bacteria. A minimum of 50,000 events were acquired from each sample at a collection rate of approximately 3,500 events per second. The mean fluorescence intensity was determined using Summit software (Beckman Coulter). Background autofluorescence was determined using the negative control S. typhi vaccine strain CVD 910.

Results

Construction of CVD 910.

The attenuated vaccine candidate CVD 908-htrA, derived from Ty2 and carrying deletions in aroC, aroD, and htrA, was previously constructed and proved to be safe and highly immunogenic in Phase 2 clinical trials.[13] Here, a new vaccine strain, CVD 910, was constructed that carries deletions in guaBA and htrA. The ΔaroC ΔaroD was replaced with the single deletion ΔguaBA for two important reasons: 1) previous work by the inventors showed that ΔguaBA alone sufficiently attenuates Ty2, resulting in a live vector strain capable of eliciting impressive humoral immunity to a plasmid-encoded foreign antigen using the murine intranasal model of immunogenicity;[14] and 2) transcriptional control of the guaBA locus is controlled by growth rate, independent of guanine-mediated repression,[15] allowing expression of properly integrated antigen expression cassettes to be increased as the live vectors grow in the host. In order to reduce the risk of reversion to virulence by the unlikely acquisition of wild type guaBA genes, a secondary deletion of htrA which encodes a heat shock-induced serine protease was further engineered.

Deletion cassettes targeting guaBA and htrA were constructed for use with the λ Red-mediated site-directed mutagenesis method,[16] and each cassette was used to successfully delete either guaBA or htrA from wildtype S. typhi Ty2. Introduction of both deletion mutations into a single strain resulted in the creation of CVD 910. A preliminary assessment of attenuation of CVD 910 was carried out by comparing the minimum lethal dose causing death in 50% of a group of BALB/c mice (LD50) for CVD 910 versus CVD 908-htrA, using the hog gastric mucin intraperitoneal murine challenge model. For this model, the guidelines recommended in the Code of Federal Regulations for Food and Drugs, Title 21, Part 620.13 (c-d), 1986 for intraperitoneal challenge of mice with S. typhi were broadly followed. Using this method, the LD50 for both CVD 910 and CVD 908-htrA was determined to be approximately $5 \times 10^5$ CFU (data not shown), versus an LD50 of ~10 CFU for wild-type Ty2,[17] demonstrating construction of a novel live vaccine strain with a safety profile equivalent to that of CVD 908-htrA.

Chromosomal Integration of GFPuv Cassettes into CVD 910.

GFPuv was expressed from independently controlled cassettes in CVD 910 (containing the guaBA and htrA chromosomal gene deletions) in the following manner. The osmotically regulated $P_{ompC}$ promoter was genetically fused to a promoterless gfpuv gene. The resulting $P_{ompC}$-gfpuv cassette was integrated into either the guaBA or htrA loci such that only the open reading frame was replaced, but the original promoters for both chromosomal loci were preserved, as depicted schematically in FIG. 1. For example, integration of $P_{ompC}$-gfpuv into the guaBA locus to create CVD 910-GG resulted in transcription of gfpuv controlled both by osmolarity (via $P_{ompC}$) and growth rate (via $P_{guaBA}$). Similarly, integration of the same cassette into htrA to create CVD 910-HG resulted in synthesis of GFPuv controlled both by osmolarity ($P_{ompC}$) and heat shock/environmental stress ($P_{htrA}$).[18] In addition, a third chromosomal integration was prepared, CVD 910-CG, in which $P_{ompC}$-gfpuv replaced clyA, encoding a cryptic hemolysin from Ty2 whose transcription is normally controlled by low pH.[19] Interestingly, when the resulting strains were grown overnight at 37° C. in liquid cultures and analyzed for fluorescence by flow cytometry, observed fluorescence intensity was found to be strongly influenced by the site of integration, regardless of osmotic induction of $P_{ompC}$. As shown in the fluorescence histograms of FIG. 2, under inducing conditions of 200 mM NaCl, strains with $P_{ompC}$-gfpuv integrated into either guaBA or htrA displayed remarkably uniform bacterial populations with mean fluorescence intensities of 28.65 and 21.59 respectively, while integration into clyA resulted in a very low mean fluorescence intensity of 7.53, barely above the background autofluorescence of 5.94 detected for CVD 910 alone. Having established substantial expression of GFPuv from two independent chromosomal loci, the hypothesis that integration of $P_{ompC}$-gfpuv into both guaBA and htrA together would result in additive expression of fluorescence was then tested. Analysis of fluorescence from the resulting strain, CVD 910-2G, revealed an uninduced (50 mM NaCl) mean fluorescence intensity of 36.01, which increased to 48.21 after induction with 200 mM NaCl. In this experiment, uninduced fluorescence intensities for CVD 910-GG and CVD 910-HG were 25.35 and 15.85 respectively, while induced fluorescence levels were 32.46 and 24.03 respectively. It is immediately evident that for overnight liquid cultures, cumulative fluorescence observed with two copies of gfpuv integrated into CVD 910-2G is approximately equivalent to the combined fluorescence levels for individual copies of integrated gfpuv observed in CVD 910-GG and CVD 910-HG, under both uninduced and induced osmotic conditions.

Growth-Phase Regulated Expression of GFPuv in CVD 910-2G.

Regulated, but sustained, expression of foreign antigens delivered by live vectors is expected to reduce any metabolic burden associated with antigen synthesis, thereby allowing live vectors to persist longer in immunized hosts and prolong delivery of candidate vaccine antigens to the immune system.[20] However, and despite recent improvements, tightly regulated and appropriately timed antigen expression using plasmid-based expression technologies still remains elusive in many cases, with leaky expression potentially contributing to over-attenuation of live vector vaccine strains. Therefore, one of the goals of the current work was to investigate the feasibility of linking foreign antigen expression to the growth phase of the live vector, such that expression would be reduced when bacteria are adapting to a significant change in environmental conditions (i.e. lag phase), but would be strongly induced after bacteria have successfully adapted their metabolism to new energy sources and environmental conditions (i.e. exponential growth transitioning into stationary phase).

To meet this goal, chromosomally-encoded GFPuv expression in CVD 910-2G was first compared to a previously described live vector CVD 908-htrAssb(pGEN206)

[3], in which GFPuv was expressed independently of growth phase from a low copy (~5 copies per chromosomal equivalent) stabilized expression plasmid. Overnight starter cultures of CVD 910-2G and CVD 908-htrAssb(pGEN206) were grown at 37° C. for approximately 16 hrs and then diluted 1:100 into 100 ml of fresh medium in 250 ml baffle flasks. To reduce the influence of osmolarity on growth phase and more clearly establish any link between observed fluorescence and induction of $P_{guaBA}$ and $P_{htrA}$ during growth, all strains were grown under non-inducing conditions of 50 mM NaCl. Fresh cultures were incubated at 37° C./250 rpm, and 5 ml aliquots were removed every hour for 6 hours to measure both $OD_{600}$ and fluorescence intensities by flow cytometry. As expected, plasmid-based expression in CVD 908-htrAssb(pGEN206) significantly slowed the growth kinetics of the live vector when compared to either CVD 910 or CVD 910-2G, even under non-inducing conditions of 50 mM NaCl (Table 2). Initial fluorescence intensities in lag phase started out quite high at 1262.66, dipped during exponential phase to 686.27, and then rose again to 1131.59 in stationary phase. In sharp contrast, the kinetics of GFPuv expression in CVD 910-2G was closely linked to the growth phase of the culture, with a low mean fluorescence intensity of 81.19 measured in the lag phase, which gradually increased with cell density to a maximum fluorescence intensity of 200.06 as the culture reached stationary phase. The observed variation of fluorescence with growth phase, as quantitated by flow cytometry, is not an aggregate effect of increasing cell numbers, but instead reflects the level of GFPuv synthesis within individual bacteria in a growth-rate dependent manner. These data support the feasibility of chromosomal expression of a foreign antigen from multiple integration sites, and the possibility of antigen expression synchronized with growth-rate, a possibility not supported by plasmid-based expression in these experiments.

TABLE 2

Chromosomal versus plasmid-based expression of GFPuv in attenuated *Salmonella Typhi* live vectors.

| Time | CVD 910 | | CVD 910-2G (guaBA::gfpuv htrA::gfpuv) | | CVD 908htrAssb (pGEN206S2) | |
|---|---|---|---|---|---|---|
| (hr) | $OD_{600}{}^a$ | MFI$^b$ | $OD_{600}$ | MFI | $OD_{600}$ | MFI |
| 0 | 0.04 | ND$^c$ | 0.04 | ND | 0.04 | ND |
| 1 | 0.07 | ND | 0.08 | 81.19 | 0.06 | 1262.66 |
| 2 | 0.27 | ND | 0.3 | 96.77 | 0.14 | 1196.59 |
| 3 | 0.71 | ND | 0.71 | 105.59 | 0.38 | 721.34 |
| 4 | 1.36 | ND | 1.36 | 182.77 | 0.72 | 686.27 |
| 5 | 1.88 | ND | 1.86 | ND | 1.25 | ND |
| 6 | 2.18 | 6.34 | 2.18 | 169.87 | 1.67 | 891.53 |
| 7 | 2.29 | ND | 2.29 | 200.06 | 1.95 | 1131.59 |

$^a$Cultures grown under non-inducing conditions in 50 mM NaCl.
$^b$Mean Fluorescence Intensity.
$^c$Not Determined.

This experiment was repeated to compare GFPuv expression from double integrations in CVD 910-2G to single integration expression levels in CVD 910-GG and CVD 910-HG. As summarized in Table 3, growth phase-dependent expression of fluorescence intensity was again observed, increasing from an initial lag phase level of 32.90 to a high of 161.65 in stationary phase. Interestingly, fluorescence levels during the 3 hr lag phase for the double integration did not reflect the sum of fluorescence observed with single integrations during this period, but became additive as the cultures progressed into exponential and stationary phases. Fluorescence intensities from single integrations did not seem to reflect the same dependence on growth phase as observed for the double integration; intensities for the guaBA integration in CVD 910-GG progressed from 74.94 to 96.31 during growth while htrA-controlled fluorescence in CVD 910-HG progressed from 32.90 to 68.94. Despite this anomaly, the data reported here suggest that integration of antigen expression cassettes into multiple loci within a live vector chromosome can be accomplished without further attenuation of the vaccine strain, and that this multiple integration strategy results in superior expression levels of foreign antigens versus conventional integration into a single locus.

TABLE 3

Growth-phase regulated chromosomal expression of GFPuv in CVD 910 attenuated *Salmonella Typhi* live vectors.

| Time | CVD 910 | | CVD 910-GG (guaBA::gfpuv) | | CVD 910-HG (htrA::gfpuv) | | CVD 910-2G (guaBA::gfpuv htrA::gfpuv) | |
|---|---|---|---|---|---|---|---|---|
| (hr) | $OD_{600}{}^a$ | MFI$^b$ | $OD_{600}$ | MFI | $OD_{600}$ | MFI | $OD_{600}$ | MFI |
| 0 | 0.04 | ND$^c$ | 0.04 | ND | 0.03 | ND | 0.02 | ND |
| 1 | 0.09 | ND | 0.09 | 74.94 | 0.06 | 32.9 | 0.06 | 38.31 |
| 2 | 0.33 | ND | 0.3 | 71.03 | 0.24 | 49.08 | 0.24 | 72.53 |
| 3 | 0.81 | ND | 0.72 | 70.58 | 0.68 | 56.12 | 0.6 | 95.41 |
| 4 | 1.45 | ND | 1.31 | 75.26 | 1.29 | 60 | 1.36 | 121.95 |
| 5 | 1.96 | ND | 1.86 | 84.81 | 1.84 | 66.55 | 1.86 | 138.01 |
| 6 | 2.24 | 5.87 | 2.17 | 96.31 | 2.19 | 68.94 | 2.16 | 161.65 |

$^a$Cultures grown under non-inducing conditions in 50 mM NaCl.
$^b$Mean Fluorescence Intensity.
$^c$Not Determined.

Construction and Testing of CVD 910-3A.

An additional strain of CVD 910 was prepared that expresses the cell binding domains from toxin A (CBD/A) or from toxin B (CBD/B) of *C. difficile*. A synthetic codon-optimized gene cassette encoding the cell binding domain from toxin A designated 14cbd/a was prepared where the osmotically regulated $P_{ompC}$ promoter was genetically fused to a promoterless 14cbd/a gene. All $P_{ompC}$-controlled antigen cassettes encoding *C. difficile* antigens were constructed by inserting synthetic codon-optimized genes (encoding the cell binding domains of either 14CBD/A (SEQ ID NO:23) or CBD/B (SEQ ID NO:24)) as NheI-AvrII fragments into pSEC10 digested either with SpeI-NheI to generate the unfused $P_{ompC}$-14cbd/a encoding 14CBD/A, or pSEC10 cleaved only with NheI to generate the fused $P_{ompC}$-clyA::cbd/b encoding ClyA-CBD/B. In the case of $P_{ompC}$-14cbd/a, the resulting cassette was then excised from pSEC10 as an EcoRI-AvrII fragment and inserted into chromosomal integration cassettes in preparation for crossing into the chromosome using previously published λ Red integration technologies (see FIG. 3) [3,16]. All integration cassettes were integrated such that only the open reading frame of either guaBA or htrA was replaced, but the original promoters for both chromosomal loci were preserved, as depicted schematically in the chromosomal integration strategy of FIG. 3. For example, integration of $P_{ompC}$-14cbd/a into the guaBA locus resulted in transcription of 14CBD/A controlled both by osmolarity (via $P_{ompC}$) and growth rate (via $P_{guaBA}$). Similarly, integration of the same cassette into htrA resulted in synthesis of 14CBD/A antigen controlled both by osmolarity ($P_{ompC}$) and heat shock/environmental stress ($P_{htrA}$). [18]

In addition, advantage was taken of the fact that all strains derived from Ty2 are naturally inactivated at the rpoS locus [24] in order to integrate a third copy of $P_{ompC}$-14cbd/a into the chromosome of CVD 910 without further attenuation of the live vector vaccine. Integration of $P_{ompC}$-14cbd/a into rpoS resulted in expression of 14CBD/A antigen controlled by osmolarity ($P_{ompC}$) and entry of growing vaccine organisms into stationary phase ($P_{rpoS}$) [25]. Additional primers used to construct the rpoS-targeted integration cassettes are listed below in Table 4.

TABLE 4

Primers used in the construction and testing of live vector strains expressing chromosomally encoded 14CBD/A from the rpoS locus.

Primer
(SEQ ID NO:)  Sequence[a]

5rpoS-for      5'-<u>AAGCTT</u>GAATTCCGTATTCTGAGGGCTCAGGTGA
SEQ ID NO: 25  ACAAAGTGC-3'

5rpoS-rev      5'-<u>CCTAGG</u>CAATTGACCCGTGATCCCTTGACGGAA
SEQ ID NO: 26  CTAGCAAGTC-3'

3rpoS-for      5'-<u>GGATCC</u>GGTTCGGTATCGCGCCAGGTATACAGA
SEQ ID NO: 27  CAATGC-3'

3rpoS-rev      5'-<u>CTCGAG</u>CCGGAAGTGCAGGCGGTAAACGCTATG
SEQ ID NO: 28  TACAC-3' rpoS PCR-for   5'-ATGCAGCACAGCAAGGAGTTGTGACCA-3'
SEQ ID NO: 29 rpoS PCR-rev   5'-GGTGCGTATCGATAAGGTCTCTTACCACAGC-3'
SEQ ID NO: 30

[a] Relevant restriction sites are underlined.

Successful integration of $P_{ompC}$-14cbd/a into guaBA, htrA, and rpoS, creating the live vector strain CVD 910-3A, was verified by direct chromosomal sequencing and listed here as SEQ ID NO:31, SEQ ID NO:32, and SEQ ID NO:33; the protein amino acid sequence for 14CBD/A is listed as SEQ ID NO:34. In all chromosomal sequences presented, the location of the $P_{ompC}$ promoter region, sequences encoding 14CBD/A, and residual FRT chromosomal scar sequences (left behind after removal of the kanamycin resistance marker) shown in Table 5. The location of key restriction sites (BamHI: GGATCC and XbaI: TCTAGA) are also shown in the Table as points of reference to be related back to the chromosomal integration strategy shown in FIG. 3.

TABLE 5

|  | $P_{ompC}$ promoter region | Antigen coding region | residual FRT chromosomal scar sequences | BamHI: GGATCC site | XbaI: TCTAGA site | NheI: GCTAGC site |
|---|---|---|---|---|---|---|
| SEQ ID NO: 23 |  | 10-984 14CBD/A |  | 991-996 |  | 13-18 |
| SEQ ID NO: 24 |  | 10-1617 CBD/B |  | 1624-1629 |  | 13-18 |
| SEQ ID N0: 31 | 876-1361 | 1388-2362 14CBD/A | 2437-2470 | 1362-1367; 2486-2491 | 2152-2157 |  |
| SEQ ID NO: 32 | 830-1315 | 1342-2316 14CBD/A | 2391-2424 | 1316-1321; 2440-2445 | 2406-2411 |  |
| SEQ ID NO: 33 | 655-1140 | 1167-2141 14CBD/A | 2231-2264 | 1141-1146; 2280-2285 | 2246-2251 |  |
| SEQ ID NO: 34 |  | 1-325 14CBD/A |  |  |  |  |
| SEQ ID NO: 35 |  | 1431-3029 14CBD/A | 699-732 |  | 714-719 |  |
| SEQ ID NO: 36 | 1-489 | 1431-3029 14CBD/A | 516-1430 | 490-495; 3084-3089 |  | 1425-1430 |
| SEQ ID NO: 37 |  | 306-838 14CBD/A | 1-305 |  |  |  |

Copy number-dependent osmotically controlled expression of 14CBD/A was confirmed by western immunoblot analysis. As shown in FIG. 4, six hour liquid broth cultures of CVD 910-2A (carrying $P_{ompC}$-14cbd/a integrated into guaBA and htrA) were compared to cultures of CVD 910-3A (carrying $P_{ompC}$-14cbd/a integrated into guaBA, htrA, and rpoS). All cultures were grown at 37° C. under either inducing (200 mM NaCl to activate $P_{ompC}$) or non-inducing (15 mM NaCl) conditions. Induction of 14CBD/A synthesis is clearly observed, with maximum expression confirmed for CVD 910-3A induced with high osmolarity.

Construction of CVD 910-3Assb(pSEC10-CBD/B).

A chromosomal deletion of ssb was introduced into CVD 910-3A as previously described [3], accompanied by introduction of the non-antibiotic SSB-stabilized expression plasmid pSEC10 into which a synthetic codon-optimized gene cassette encoding the cell binding domain of *C. difficile* toxin B was inserted. The resulting live vaccine strain, designated CVD 910-3Assb(pSEC10-CBD/B) is depicted schematically in FIG. 5. Confirmation of the chromosomal deletion of ssb as intended was confirmed by direct chromosomal sequencing as listed in SEQ ID NO:35; the integrity of the plasmid-based $P_{ompC}$-clyA-cbd/b cassette was also confirmed by direct sequencing as listed in SEQ ID NO:36, with the predicted amino acid sequence of ClyA-CBD/B listed in SEQ ID NO:37. Here again, for SEQ ID NO:35, the location of the residual FRT chromosomal scar sequences (replacing the deleted ssb gene) is shown in Table 5 along with the location of the internal XbaI site (TCTAGA). For the SEQ ID NO:36 sequence encoding ClyA-CBD/B, the location of the $P_{ompC}$ promoter region is also shown in Table 5 along with the locations of the sequence encoding CBD/B and the key restriction sites (BamHI: GGATCC, NheI: GCTAGC, and AvrII: CCTAGG).

Proof-of-Principle Immunogenicity and Challenge Experiment Using a CVD 910 Bivalent Plague Vaccine.

The strategy for development of CVD 910-3Assb (pSEC10-CBD/B) was informed by a critical proof-of-principle experiment in which a bivalent live vector vaccine against pulmonary plague caused by *Yersinia pestis* was constructed and tested. Using the identical genetic engineering strategy used to create CVD 910-3Assb(pSEC10-CBD/B), a bivalent CVD 910-based plague vaccine was constructed that expressed the full-length LcrV antigen (required for secretion of virulence effectors proteins and a virulence factor by itself) from the three independent guaBA, htrA, and rpoS chromosomal sites, each containing an osmotically-regulated $P_{ompC}$-lcrV cassette. The protective anti-phagocytic capsular F1 antigen was expressed from the SSB-stabilized non-antibiotic low copy expression plasmid pSEC10, creating the plasmid pSL445. The F1 antigen of pSL445 was encoded by the natural *Y. pestis* caf1 operon but engineered to be transcriptionally controlled by the in vivo-inducible sifA promoter (an *S. typhi* promoter controlled by the *Salmonella* Pathogenicity Island 2 (SPI 2) regulon), after having determined that expression of caf1 using the $P_{ompC}$ promoter was toxic to CVD 910. For comparison, the bivalent plasmid pSL483 (again derived from pSEC10) was also constructed in which the expression of both the caf1 operon and lcrV were divergently transcribed from the $P_{sifA}$ and $P_{ompC}$ promoters respectively. SL483 was then introduced into CVD 908-htrAssb creating a bivalent plague candidate vaccine CVD 908-htrAssb (pSL483) in which foreign antigen expression was completely plasmid encoded, to be compared to CVD 910-3Lssb (pSL445) in which foreign antigen expression was balanced between the chromosome and a plasmid.

The immunogenicity of these live vector vaccine strains was evaluated using a heterologous prime-boost immunization strategy in which BALB/c mice were primed intranasally with $1 \times 10^9$ CFU of live vaccine on days 0 and 28, followed by a boost with a small amount (500 nanograms) of purified lcrV adsorbed to alum on day 56. All mice were challenged on day 84 (i.e., 28 days after the last immunization) with 177 LD50s of virulent *Y. pestis* strain CO92. Results are presented in Table 6.

TABLE 6

Immunogenicity of *S. Typhi* live vector candidate plague vaccines expressing LcrV and F1 and further tested for efficacy in a lethal pulmonary challenge model.

| Vaccine | Day 28 (before boost 1) | Day 42 | Day 56 (before boost 2) | Day 84 (4 weeks post boost 2) | Percent survival (14 days post challenge) |
|---|---|---|---|---|---|
| F1-specific serum IgG | | | | | |
| CVD 910 | 12.5 | 12.5 | 12.5 | 12.5 | 40% |
| CVD 910-3L | 212.5 | 12.5 | 12.5 | 12.5 | 70% |
| CVD 910-3Lssb(pSL445) | 2,268.3 | 33,810.9 | 16,613.2 | 21,778.3 | 100% |
| CVD 908-htrAssb(pSL483) | 445.2 | 11,056.1 | 1,706.5 | 3,684.7 | 100% |
| PBS prime-LcrV boost | 12.5 | 12.5 | 12.5 | 12.5 | 20% |
| PBS | 12.5 | 12.5 | 12.5 | 12.5 | 0% |
| LcrV-specific serum IgG | | | | | |
| CVD 910 | 49.4 | 125.0 | 12.5 | 78,994.1 | |
| CVD 910FL | 93.9 | 224.6 | 12.5 | 86,968.7 | |
| CVD 910-3Lssb(pSL445) | 25.0 | 75.4 | 12.5 | 228,230.1 | |
| CVD 908-htrAssb(pSL483) | 25.0 | 20,008.9 | 21,267.3 | 407,085.8 | |
| PBS prime-LcrV boost | 25.0 | 51.3 | 12.5 | 28,855.7 | |
| PBS | 25.0 | 25.0 | 12.5 | 12.5 | |
| Typhi LPS-specific serum IgG | | | | | |
| CVD 910 | 168.5 | 3,570.8 | Pending | 30,192.9 | |
| CVD 910-3L | 311.8 | 7,088.0 | 18,754.0 | 52,266.0 | |
| CVD 910-3Lssb(pSL445) | 171.5 | 1,366.9 | Pending | 18,917.4 | |
| CVD 908-htrAssb(pSL483) | 135.3 | 1,248.5 | Pending | 1,968.6 | |
| PBS prime-LcrV boost | 157.8 | 121.3 | 307.0 | 244.2 | |
| PBS | 150.9 | 116.5 | 297.6 | 188.7 | |

These results clearly show that when expression of foreign antigens is balanced between inducible multilocus chromosomal expression and inducible plasmid-based expression, serum antibody responses against both foreign antigens LcrV and F1 were equivalent to that observed when both antigens were expressed from a single stabilized expression plasmid. Perhaps more importantly, when examining live vector-specific LPS responses, serum IgG responses 10 fold higher were observed in mice immunized with CVD 910-3Lssb(pSL445) versus responses in mice immunized with CVD 908-htrAssb(pSL483) (day 84 GMT=18,917.4 versus 1,968.6 respectively). These results strongly support the hypothesis that the metabolic burden associated with expression of multiple foreign antigens in attenuated multivalent live vector vaccines can be reduced or even eliminated by engineering appropriately balanced levels of antigen expression, accomplished by strategic distribution of foreign genes between multiple chromosomal loci and genetically stabilized low copy plasmids.

Construction of a Multivalent CVD 910 Live Vector Vaccine Targeting Enterotoxins and a Putative Colonization Factor of C. difficile.

Enterotoxins A (TcdA) and B (TcdB) are the primary virulence factors of C. difficile. However, epidemic strains of C. difficile invariably carry an additional toxin affecting the actin cytoskeleton of intestinal cells called C. difficile transferase (Cdt); this toxin has also been called binary toxin (BT) because it is composed of a catalytic A subunit and a cell-binding B subunit (30, 31). The activity of BT causes rearrangement of the actin cytoskeleton of intestinal epithelial cells, disrupting tight junctions and potentially allowing better penetration of enterotoxins into gastrointestinal tissue (32), thereby enhancing the virulence of epidemic strains. It was recently discovered that BT also appears to enhance colonization of the intestinal tract by inducing microtubule-based protrusions which enhance the adherence of C. difficile (33). Based on available data, it was hypothesized that binary toxin acts to enhance the virulence of epidemic strains carrying all three toxins by promoting better colonization of C. difficile and possibly improving the penetration and binding of enterotoxins A and B. Recent animal studies suggest that immunization against enterotoxins alone does not prevent colonization of the gastrointestinal tract by C. difficile (34), and that strains producing only binary toxin are able to colonize susceptible animals (35). Therefore, live vector-mediated mucosal immunity against C. difficile disease will be targeted at three levels: 1] by blocking the binding of both enterotoxins through targeting of serum immunity to their cell-binding domains, 2] by inducing mucosal immunity to the cell binding domain of BT (designated here as CBD-BT) to reduce penetration of toxins A and B by maintaining the integrity of intestinal epithelial tissue, and 3] by targeting mucosal immunity against CBD-BT to reduce intestinal colonization, recurrent infection, and environmental transmission in a clinical setting.

Towards this goal of constructing a trivalent live vaccine against C. difficile infections in which mucosal immunity is targeted against enterotoxins A, B, and binary toxin, CVD 910-3A was first modified to express CBD/A from one further chromosomal locus, namely the clyA locus. This modification serves to avoid loss of expression of chromosomally encoded 14CBD/A from the three chromosomal loci of CVD 910-3A. Integration of $P_{ompC}$-14cbd/a into the clyA locus was completed using the method described above in the paragraph entitled "Construction and testing of CVD 910-3A"; this integration cassette was integrated such that only the open reading frame encoded by clyA was replaced, while preserving the original clyA promoter, as depicted schematically in the chromosomal integration strategy of FIG. 3.

The resulting monovalent vaccine strain, CVD 910-4A, was then further modified to contain and express CBD-BT fused to the carboxyl terminus of ClyA in the manner routinely used in low copy number SSB-stabilized expression plasmids; as with other expression cassettes constructed in these plasmids and later moved into chromosomal integration modules, this clyA::cbd-bt gene fusion was again transcriptionally controlled by the osmotically regulated promoter $P_{ompC}$. In order to take advantage of the previously constructed integration modules in which incoming expression cassettes encoding foreign antigens were inserted as EcoRI-AvrII fragments, it was necessary to create a new synthetic gene encoding ClyA in which the internal naturally occurring EcoRI site was removed; the resulting synthetic gene (designated clyA*) was then re-inserted into pSEC10 to create pSEC10S2 (SEQ ID NO:45). In addition to the EcoRI site (base 1034, T to C), other commonly used restriction sites in pSEC10S2 (SEQ ID NO:45) were removed, including BglII (base 590, T to C), two HindIII sites (base 686, A to G; base 1043, A to G), HpaI (base 978, T to C; base 980, A to G) and MfeI (base 1262, A to G).

A synthetic 2655 bp codon-optimized gene encoding the 878 residues of CBD-BT (SEQ ID NO:46) was then synthesized as a NheI-AvrII fragment (SEQ ID NO:47). However, insertion of this cassette into pSEC10S2 cleaved with NheI was unsuccessful. A smaller gene cassette encoding residues 212-878 of CBD-BT (designated B2; SEQ ID NO:46) was amplified using the forward primer 5'-AGATCTaaataaggaggaaaaaaaaATGGCTAGCCTGATGTCT-GATTGGGAAGATGAAG-3' (NheI site underlined; SEQ ID NO:51) and the reverse primer 5-AAGCTT CCTAGGTTATTAATCCACACTCAGAACCAGCAGT-TCG-3' (AvrII site underlined; SEQ ID NO:52); this decision was based on a report by Sundriyal et al. (36) demonstrating the biological activity of this truncated portion of CBD-BT which results naturally from proteolytic cleavage of the full-length 98.8 kDa CBD-BT, removing a 20 kDa N-terminal fragment, and resulting in a soluble 74.9 kDa protein. The resulting 2054 bp synthetic gene (SEQ ID NO:48) was then successfully inserted as a NheI-AvrII fragment into pSEC10S2 cleaved with NheI to create pSEC10S2-B2 encoding a 972 residue 108.6 kDa ClyA-CBD-BT fusion protein (SEQ ID NO:49). This plasmid was then introduced into CVD 910-4A to create the bivalent vaccine CVD 910-4Assb(pSEC10S2-B2).

The $P_{ompC}$-clyA*-b2 expression cassette was then excised from pSEC10S2-B2 as a 3491 bp EcoRI-AvrII fragment (SEQ ID NO:50), inserted into the guaBA integration module cleaved with MfeI-NheI, and then integrated into the guaBA locus of CVD 910-4A, replacing the previously integrated $P_{ompC}$-14cbd/a cassette to create the bivalent live vaccine CVD 910-3A-GB2 in which 14CBD/A is chromosomally expressed from the htrA, rpoS, and clyA loci, and CBD-BT is expressed from the guaBA locus. When export of the protein fusion was compared for hemolytic activity with plasmid-encoded fusion protein expressed in CVD 910-4Assb(pSEC10S2-B2), proper export of the fusion protein was observed in both strains, although plasmid-encoded export was much higher due to copy number (FIG. 6).

The SSB-stabilized plasmid encoding the cell binding domain of enterotoxin B, pSEC10-CBD/B, is introduced into CVD 910-3A-GB2 to create the trivalent live vaccine CVD 910-3A-GB2ssb(pSEC10-CBD/B) shown in FIG. 7 in which 14CBD/A is chromosomally expressed from the htrA, rpoS, and clyA loci, CBD-B2 is expressed from the guaBA locus, and CBD/B is expressed from pSEC10-CBD/B.

Alternatively, the SSB-stabilized plasmid encoding the cell binding domain of enterotoxin B, pSEC10-CBD/B, is introduced into CVD 910-2A-GRB2 to create the trivalent live vaccine CVD 910-2A-GRB2ssb(pSEC10-CBD/B) in which 14CBD/A is chromosomally expressed from the htrA and clyA loci, CBD-B2 is expressed from the guaBA locus and rpoS locus, and CBD/B is expressed from pSEC10-CBD/B.

To improve binary toxin-specific toxin neutralizing activity, a second copy of $P_{ompC}$-clyA*-b2 can be inserted into the rpoS locus of CVD 910-3A-GB2ssb(pSEC10-CBD/B).

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Wang S, Li Y, Shi H, Sun W, Roland K L, Curtiss R, III. Comparison of a regulated delayed antigen synthesis system with in vivo-inducible promoters for antigen delivery by live attenuated Salmonella vaccines. Infect Immun 2011; 79:937-949.
2. Galen J E, Levine M M. Can a 'flawless' live vector vaccine strain be engineered? Trends in Microbiology 2001; 9:372-376.
3. Galen J E, Wang J Y, Chinchilla M, Vindurampulle C, Vogel J E, Levy H, et al. A new generation of stable, nonantibiotic, low-copy-number plasmids improves immune responses to foreign antigens in Salmonella enterica serovar typhi live vectors. Infect Immun 2010; 78:337-347.
4. Cranenburgh R M, Lewis K S, Hanak J A. Effect of plasmid copy number and lac operator sequence on antibiotic-free plasmid selection by operator-repressor titration in Escherichia coli. J Mol Microbiol Biotechnol 2004; 7:197-203.
5. Nakayama K, Kelley S M, Curtiss III R. Construction of an Asd+expression-cloning vector: stable maintenance and high level expression of cloned genes in a Salmonella vaccine strain. Bio/Technology 1988; 6:693-697.
6. Galen J E, Zhao L, Chinchilla M, Wang J Y, Pasetti M F, Green J, et al. Adaptation of the endogenous Salmonella enterica serovar typhi clyA-encoded hemolysin for antigen export enhances the immunogenicity of anthrax protective antigen domain 4 expressed by the attenuated live-vector vaccine strain CVD 908-htrA. Infect Immun 2004; 72:7096-7106.
7. Galen J E, Chinchilla M, Pasetti M F, Wang J Y, Zhao L, rciniega-Martinez I, et al. Mucosal immunization with attenuated Salmonella enterica serovar typhi expressing protective antigen of anthrax toxin (PA83) primes monkeys for accelerated serum antibody responses to parenteral PA83 vaccine. J Infect Dis 2009; 199:326-335.
8. Gentschev I, Dietrich G, Goebel W. The E. coli alpha-hemolysin secretion system and its use in vaccine development. Trends Microbiol 2002; 10:39-45.
9. Kang H Y, Curtiss R, III. Immune responses dependent on antigen location in recombinant attenuated Salmonella typhimurium vaccines following oral immunization. FEMS Immunol Med Microbiol 2003; 37:99-104.
10. Smith M A, Bidochka M J. Bacterial fitness and plasmid loss: the importance of culture conditions and plasmid size. Can J Microbiol 1998; 44:351-355.
11. Gonzalez C, Hone D M, Noriega F, Tacket C O, Davis J R, Losonsky G, et al. Salmonella typhi vaccine strain CVD 908 expressing the circumsporozoite protein of Plasmodium falciparum: strain construction and safety and immunogenicity in humans. J Infect Dis 1994; 169:927-931.
12. Hohmann E L, Oletta C A, Loomis W P, Miller S I. Macrophage-inducible expression of a model antigen in Salmonella typhimurium enhances immunogenicity. Proc Natl Acad Sci USA 1995; 92:2904-2908.
13. Tacket C O, Sztein M, Wasserman S S, Losonsky G, Kotloff K, Wyant T L, et al. Phase 2 clinical trial of attenuated Salmonella enterica serovar typhi oral live vector vaccine CVD 908-htrA in U.S. volunteers. Infect Immun 2000; 68:1196-1201.
14. Wang J Y, Pasetti M F, Noriega F, Anderson R J, Wasserman S S, Galen J E, et al. Construction, genotypic and phenotypic characterization, and immunogenicity of attenuated ΔguaBA Salmonella enterica serovar typhi strain CVD 915. Infect Immun 2001; 69:4734-4741.
15. Husnain S I, Thomas M S. The UP element is necessary but not sufficient for growth rate-dependent control of the Escherichia coli guaB promoter. J Bacteriol 2008; 190:2450-2457.
16. Datsenko K A, Wanner B L. One-step inactivation of chromosomal genes in Escherichia coli K-12 using PCR products. Proc Natl Acad Sci USA 2000; 97:6640-6645.
17. Tacket C O, Hone D M, Curtiss III R, Kelly S M, Losonsky G, Guers L, et al. Comparison of the safety and immunogenicity of ΔaroCΔaroD and ΔcyaΔcrp Salmonella typhi strains in adult volunteers. Infect Immun 1992; 60:536-541.
18. Lewis C, Skovierova H, Rowley G, Rezuchova B, Homerova D, Stevenson A, et al. Salmonella enterica serovar Typhimurium HtrA: regulation of expression and role of the chaperone and protease activities during infection. Microbiology 2009; 155:873-881.
19. Fuentes J A, Jofre M R, Villagra N A, Mora G C. RpoS- and Crp-dependent transcriptional control of Salmonella typhi taiA and hlyE genes: role of environmental conditions. Res Microbiol 2009; 160:800-808.
20. Galen J E, Pasetti M F, Tennant S M, Olvera-Ruiz P, Sztein M B, Levine M M. Salmonella enterica serovar typhi Live Vector Vaccines Finally Come of Age. Immunol Cell Biol 2009; 87:400-412.
21. Xu X, Husseiny M I, Goldwich A, Hensel M. Efficacy of intracellular activated promoters for generation of Salmonella-based vaccines. Infect Immun 2010; 78:4828-4838.
22. Everest P, Frankel G, Li J, Lund P, Chatfield S, Dougan G. Expression of LacZ from the htrA, nirB, and groE promoters in a Salmonella vaccine strain: influence of growth in mammalian cells. FEMS Microbiol Lett 1995; 126:97-102.
23. Galen J E, Nair J, Wang J Y, Wasserman S S, Tanner M K, Sztein M, et al. Optimization of plasmid maintenance in the attenuated live vector vaccine strain Salmonella typhi CVD 908-htrA. Infect Immun 1999; 67:6424-6433.

24. Robbe-Saule V, Norel F. The rpoS mutant allele of *Salmonella typhi* Ty2 is identical to that of the live typhoid vaccine Ty21a. FEMS Microbiol Lett 1999 Jan. 1; 170(1):141-3.
25. Hirsch M, Elliott T. Fis regulates transcriptional induction of RpoS in *Salmonella enterica*. J Bacteriol 2005 March; 187(5):1568-80.
26. Wallace, A. J., T. J. Stillman, A. Atkins, S. J. Jamieson, P. A. Bullough, J. Green, and P. J. Artymiuk. 2000. *E. coli* hemolysin E (HlyE, ClyA, SheA): X-ray crystal structure of the toxin and observation of membrane pores by electron microscopy. Cell 100:265-276.
27. Oscarsson, J., Y. Mizunoe, L. Li, X. Lai, A. Wieslander, and B. E. Uhlin. 1999. Molecular analysis of the cytolytic protein ClyA (SheA) from *Escherichia coli*. Mol. Microbiol. 32:1226-1238.
28. Galen et al. *Immunol. Cell Biol.* May 5, 2009, pp 1-13.
29. Metcalf et al. Conditionally replicative and conjugative plasmids carrying lacZ alpha for cloning, mutagenesis, and allele replacement in bacteria. 1996. 35(1): 1-13.
30. Perelle S, Gibert M, Bourlioux P, Corthier G, Popoff M R. 1997. Production of a complete binary toxin (actin-specific ADP-ribosyltransferase) by *Clostridium difficile* CD196. Infect. Immun. 65:1402-1407.
31. Rupnik M, Grabnar M, Geric B. 2003. Binary toxin producing *Clostridium difficile* strains. Anaerobe. 9:289-294.
32. Carter G P, Rood J I, Lyras D. 2010. The role of toxin A and toxin B in *Clostridium difficile*-associated disease. Gut Microbes 1:58-64.
33. Schwan C, Stecher B, Tzivelekidis T, van HM, Rohde M, Hardt W D, Wehland J, Aktories K. 2009. *Clostridium difficile* toxin CDT induces formation of microtubule-based protrusions and increases adherence of bacteria. PLoS. Pathog. 5:e1000626.
34. Siddiqui F, O'Connor J R, Nagaro K, Cheknis A, Sambol S P, Vedantam G, Gerding D N, Johnson S. 2012. Vaccination with parenteral toxoid B protects hamsters against lethal challenge with toxin A-negative, toxin B-positive *Clostridium difficile* but does not prevent colonization. J. Infect. Dis. 205:128-133.
35. Geric B, Carman R J, Rupnik M, Genheimer C W, Sambol S P, Lyerly D M, Gerding D N, Johnson S. 2006. Binary toxin-producing, large clostridial toxin-negative *Clostridium difficile* strains are enterotoxic but do not cause disease in hamsters. J. Infect. Dis. 193:1143-1150.
36. Sundriyal A, Roberts A K, Ling R, McGlashan J, Shone C C, Acharya K R. 2010. Expression, purification and cell cytotoxicity of actin-modifying binary toxin from *Clostridium difficile*. Protein Expr. Purif. 74:42-48.

---

What is claimed is:

1. An attenuated strain of *Salmonella enterica* serovar *typhi* (*S. typhi*) having disruptions of three or more chromosomal locations, said locations selected from the group consisting of the guaBA locus, the htrA locus, the clyA locus, the rpoS locus, and the ssb locus.

2. The attenuated strain of claim 1, wherein the attenuated strain is the strain CVD 910 which has disruptions of the guaBA locus, the htrA locus, and the rpoS locus.

3. The attenuated strain of claim 1, wherein the attenuated strain further comprises a chromosomal-based expression system integrated into each location of chromosomal disruption, and wherein each chromosomal-based expression system comprises an expression cassette encoding an antigen.

4. The attenuated strain of claim 3, wherein each expression cassette individually encodes an antigen selected from the group consisting of the cell binding domain of *C. difficile* toxin A (CBD/A), the cell binding domain of *C. difficile* toxin B (CBD/B), and the cell binding domain of *C. difficile* binary toxin.

5. The attenuated strain of claim 3, wherein the attenuated strain has disruptions of the guaBA locus, the htrA locus, and the rpoS locus.

6. The attenuated strain of claim 3, wherein the attenuated strain is the strain CVD 910-3A which has disruptions of the guaBA locus, the htrA locus, and the rpoS locus, and wherein each expression cassette encodes the cell binding domain of *C. difficile* toxin A.

7. The attenuated strain of claim 3, wherein the attenuated strain further comprises (one or more plasmid-based expression systems, and wherein each plasmid-based expression system encodes an antigen.

8. The attenuated strain of claim 7, wherein each expression cassette individually encodes an antigen selected from the group consisting of the cell binding domain of *C. difficile* toxin A (CBD/A), the cell binding domain of *C. difficile* toxin B (CBD/B), and the cell binding domain of *C. difficile* binary toxin.

9. The attenuated strain of claim 7, wherein one of the locations of chromosomal disruption is the ssb locus and the plasmid-based expression system is an SSB-stabilized plasmid-based expression system.

10. The attenuated strain of claim 7, wherein the attenuated strain is the strain CVD 910-3Assb which has disruptions of the guaBA locus, the htrA locus, the rpoS locus and the ssb locus, wherein each expression cassette encodes the cell binding domain of *C. difficile* toxin A, and wherein the plasmid-based expression system is an SSB-stabilized plasmid-based expression system.

11. The attenuated strain of claim 7, wherein the attenuated strain is the strain CVD 910-3Assb(pSEC10-CBD/B) which has disruptions of the guaBA locus, the htrA locus, the rpoS locus and the ssb locus, wherein each expression cassette encodes the cell binding domain of *C. difficile* toxin A, and wherein the plasmid-based expression system is an SSB-stabilized plasmid-based expression system encoding the cell binding domain of *C. difficile* toxin B.

12. The attenuated strain of claim 7, wherein the attenuated strain comprises (disruptions of the guaBA locus, the htrA locus, the clyA locus, and the rpoS locus,
wherein the chromosomal-based expression system integrated into the guaBA chromosomal disruption comprises an expression cassette encoding the binary toxin (BT) of *C. difficile*,
wherein the chromosomal-based expression systems integrated into each of the htrA, clyA and rpoS chromosomal disruptions comprise expression cassettes encoding the cell binding domain of *C. difficile* toxin A (CBD/A), and
wherein the plasmid-based expression system encodes the cell binding domain of *C. difficile* toxin B (CBD/B).

13. The attenuated strain of claim 12, wherein the attenuated strain further comprises a disruption of the ssb locus and the plasmid-based expression system is a SSB-stabilized plasmid-based expression system.

14. The attenuated strain of claim 13, wherein the attenuated strain is CVD 910-3A-GB2ssb(pSEC10-CBD/B).

15. The attenuated strain of claim 12 formulated as a pharmaceutical composition comprising a pharmaceutically-acceptable carrier or diluent.

16. A method of inducing an immune response to an antigen in a subject, comprising administering to a subject the pharmaceutical composition according to claim 15.

* * * * *

SEQUENCE LISTING

```
<160> NUMBER OF SEQ ID NOS: 52

<210> SEQ ID NO 1
<211> LENGTH: 29
<212> TYPE: DNA
<213> ORGANISM: Artificial Sequence
<220> FEATURE:
<223> OTHER INFORMATION: Primer 5guaBA-for

<400> SEQUENCE: 1
gaattctagc tgctcatact tctgctgca                                           29

<210> SEQ ID NO 2
<211> LENGTH: 30
<212> TYPE: DNA
<213> ORGANISM: Artificial Sequence
<220> FEATURE:
<223> OTHER INFORMATION: Primer 5guaBA-rev

<400> SEQUENCE: 2
gctagccaat tggggcaata tctcacctgg                                          30

<210> SEQ ID NO 3
<211> LENGTH: 32
<212> TYPE: DNA
<213> ORGANISM: Artificial Sequence
<220> FEATURE:
<223> OTHER INFORMATION: Primer 3guaBA-for

<400> SEQUENCE: 3
ggatccacta gtgtcgataa cccttcctgt gt                                       32

<210> SEQ ID NO 4
<211> LENGTH: 29
<212> TYPE: DNA
<213> ORGANISM: Artificial Sequence
<220> FEATURE:
<223> OTHER INFORMATION: Primer 3guaBA-rev
```

```
<400> SEQUENCE: 4
ctcgagacag cacctacaag tctggcatg                                    29

<210> SEQ ID NO 5
<211> LENGTH: 24
<212> TYPE: DNA
<213> ORGANISM: Artificial Sequence
<220> FEATURE:
<223> OTHER INFORMATION: Primer guaBA PCR-for

<400> SEQUENCE: 5
gcgctgacca ccggaatacg gctg                                         24

<210> SEQ ID NO 6
<211> LENGTH: 28
<212> TYPE: DNA
<213> ORGANISM: Artificial Sequence
<220> FEATURE:
<223> OTHER INFORMATION: Primer guaBA PCR-rev

<400> SEQUENCE: 6
catggcatgg atgaggcaac cgcgaagc                                     28

<210> SEQ ID NO 7
<211> LENGTH: 36
<212> TYPE: DNA
<213> ORGANISM: Artificial Sequence
<220> FEATURE:
<223> OTHER INFORMATION: Primer 5htrA-for

<400> SEQUENCE: 7
gaattcgtac cttcaatcag gcgttactgg aagatg                            36

<210> SEQ ID NO 8
<211> LENGTH: 49
<212> TYPE: DNA
<213> ORGANISM: Artificial Sequence
<220> FEATURE:
<223> OTHER INFORMATION: Primer 5htrA-rev

<400> SEQUENCE: 8
gctagccaat tgcgattaac aggtaacgca aaattgctgt gtacgtcag              49

<210> SEQ ID NO 9
<211> LENGTH: 44
<212> TYPE: DNA
<213> ORGANISM: Artificial Sequence
<220> FEATURE:
<223> OTHER INFORMATION: Primer 3htrA-for

<400> SEQUENCE: 9
ggatccacta gtctgcgtaa gattctcgac agcaagccgt cggt                   44

<210> SEQ ID NO 10
<211> LENGTH: 42
<212> TYPE: DNA
<213> ORGANISM: Artificial Sequence
<220> FEATURE:
<223> OTHER INFORMATION: Primer 3htrA-rev

<400> SEQUENCE: 10
ctcgagccag catcatttcg gcagtcatac acaccagttc gc                     42
```

<210> SEQ ID NO 11
<211> LENGTH: 29
<212> TYPE: DNA
<213> ORGANISM: Artificial Sequence
<220> FEATURE:
<223> OTHER INFORMATION: Primer htrA PCR-for

<400> SEQUENCE: 11
gtgtcgccga tcttgaagac gcggtagag                                    29

<210> SEQ ID NO 12
<211> LENGTH: 29
<212> TYPE: DNA
<213> ORGANISM: Artificial Sequence
<220> FEATURE:
<223> OTHER INFORMATION: Primer htrA PCR-rev

<400> SEQUENCE: 12
ctatcgacgc caagctggcc gctgtcgac                                    29

<210> SEQ ID NO 13
<211> LENGTH: 51
<212> TYPE: DNA
<213> ORGANISM: Artificial Sequence
<220> FEATURE:
<223> OTHER INFORMATION: Primer 5clyA-for

<400> SEQUENCE: 13
tagtaatgag aattcgctgg tattgatcgg ctctccggta gagattagcg a           51

<210> SEQ ID NO 14
<211> LENGTH: 49
<212> TYPE: DNA
<213> ORGANISM: Artificial Sequence
<220> FEATURE:
<223> OTHER INFORMATION: Primer 5clyA-rev

<400> SEQUENCE: 14
gctagccaat tgtgcctctt taaatatata aattgcaatt aagtacctg              49

<210> SEQ ID NO 15
<211> LENGTH: 56
<212> TYPE: DNA
<213> ORGANISM: Artificial Sequence
<220> FEATURE:
<223> OTHER INFORMATION: Primer 3clyA-for

<400> SEQUENCE: 15
ggatccacta gtgatacatt ttcattcgat ctgtgtactt ttaacgcccg atagcg      56

<210> SEQ ID NO 16
<211> LENGTH: 57
<212> TYPE: DNA
<213> ORGANISM: Artificial Sequence
<220> FEATURE:
<223> OTHER INFORMATION: Primer 3clyA-rev

<400> SEQUENCE: 16
tgatagtaac tcgagacaat ccataagaaa ggtcaggcac actgggaagg cgacatc     57

<210> SEQ ID NO 17
<211> LENGTH: 27
<212> TYPE: DNA
<213> ORGANISM: Artificial Sequence
<220> FEATURE:
<223> OTHER INFORMATION: Primer clyA PCR-for

<400> SEQUENCE: 17
catgatggta tccagtatgg cacaagc                                          27

<210> SEQ ID NO 18
<211> LENGTH: 27
<212> TYPE: DNA
<213> ORGANISM: Artificial Sequence
<220> FEATURE:
<223> OTHER INFORMATION: Primer clyA PCR-rev

<400> SEQUENCE: 18
gtaatcgaca acatgctaca tccatcg                                          27

<210> SEQ ID NO 19
<211> LENGTH: 33
<212> TYPE: DNA
<213> ORGANISM: Artificial Sequence
<220> FEATURE:
<223> OTHER INFORMATION: Primer 5FRT-aph-for

<400> SEQUENCE: 19
gaattcgcta gcgctggagc tgcttcgaag ttc                                   33

<210> SEQ ID NO 20
<211> LENGTH: 33
<212> TYPE: DNA
<213> ORGANISM: Artificial Sequence
<220> FEATURE:
<223> OTHER INFORMATION: Primer 3FRT-aph-rev

<400> SEQUENCE: 20
ctcgagttcc ggggatccgt cgacctgcag ttc                                   33

<210> SEQ ID NO 21
<211> LENGTH: 32
<212> TYPE: DNA
<213> ORGANISM: Artificial Sequence
<220> FEATURE:
<223> OTHER INFORMATION: Primer 5gfpuv

<400> SEQUENCE: 21
caattgtgtg gtagcacaga ataatgaaaa gt                                    32

<210> SEQ ID NO 22
<211> LENGTH: 30
<212> TYPE: DNA
<213> ORGANISM: Artificial Sequence
<220> FEATURE:
<223> OTHER INFORMATION: Primer 3gfpuv

<400> SEQUENCE: 22
gctagctcat tatttgtaga gctcatccat                                       30

<210> SEQ ID NO 23
<211> LENGTH: 996
<212> TYPE: DNA
<213> ORGANISM: Artificial Sequence
<220> FEATURE:
<223> OTHER INFORMATION: codon-optimized gene cassette tcdA-14CBD/A

<400> SEQUENCE: 23
tagtaatgaa tggctagcac cggctatacg agcatcaacg ggaagcattt ttatttcaat 60
accgacggca ttatgcagat cggggtgttc aaagggccca acggtttcga atactttgcg 120
ccggccaaca cggatgcgaa taacatcgaa ggtcaagcca tcctctacca gaacaaattc 180

-continued

```
ctgaccctca atggcaagaa atattacttc gggtccgaca gcaaggctgt cacgggtctg    240
cgcacgattg atgggaaaaa gtattacttc aacaccaata ctgccgtggc ggtcaccgga    300
tggcaaacga tcaacggcaa gaaatactac ttcaatacca acacgtccat tgcctcgacc    360
gggtatacga tcatttccgg caaacacttc tacttcaaca ccgacgggat catgcaaatc    420
ggtgtgttta aagggcccga tggcttcgag tactttgccc cggcgaatac ggacgccaat    480
aacattgaag gtcaggcaat tcggtatcag aatcgttttc tctatctgca tgacaacatc    540
tactatttcg gtaataacag caaggcggcc accgggtggg tcacgattga tggcaaccgg    600
tattacttcg agcccaatac ggcgatgggg gcgaatggtt ataaaacgat cgacaacaag    660
aatttctact ttcgcaacgg gctcccgcag attggcgtgt tcaaagggtc caacggcttt    720
gagtacttcg cccccgcgaa tacggatgcc aacaatatcg agggccaagc gattcggtat    780
caaaaccgct tcctccacct gctcgggaaa atctattact tcggcaataa ctcgaaagcc    840
gtcacgggtt ggcaaacgat taatggcaaa gtgtattact tcatgccgga tactgcaatg    900
gcagccgctg gtggattatt cgaaattgac ggcgtcatct atttctttgg cgtggatggg    960
gtcaaagccc cggggatcta tggctaatga cctagg                              996
```

```
<210> SEQ ID NO 24
<211> LENGTH: 1629
<212> TYPE: DNA
<213> ORGANISM: Artificial Sequence
<220> FEATURE:
<223> OTHER INFORMATION: codon-optimized gene cassette TcdB CBD/B

<400> SEQUENCE: 24
tagtaatgaa tggctagcgg cctgatctat attaacgatt cactgtacta tttcaagccg     60
cccgtcaata acctcatcac cgggtttgtg acggtcggcg acgataaata ctacttcaat    120
ccgatcaacg gcggagccgc gagcattggg gagaccatca ttgatgacaa gaattattac    180
ttcaaccaga gtggcgtgct gcagacgggg gtcttcagta ccgaggacgg ctttaaatac    240
ttcgcccccg cgaatacgct cgatgagaac ctggaagggg aggcgattga ctttaccggc    300
aagctgatca ttgacgagaa catctactat ttcgatgaca attaccgcgg ggccgtggaa    360
tggaaggagc tcgatggcga gatgcactat tttagcccgg agacggggaa agctttcaaa    420
ggcctgaatc aaattgggga ctacaagtat tacttcaact ctgacggtgt gatgcagaag    480
gggttcgtga gtatcaatga caacaagcat tatttcgacg attctggcgt catgaaagtg    540
gggtacaccg agatcgatgg caagcacttc tactttgccg agaatggtga gatgcaaatc    600
ggcgtgttca atacggaaga cgggtttaag tatttcgcgc atcataacga ggatctcggc    660
aatgaagagg gcgaagagat ctcatattcc ggaatcctca acttcaataa caagatttac    720
tactttgatg actcatttac cgccgtggtc ggctggaagg acctcgagga tgggtcaaag    780
tactatttcg acgaggatac ggcggaggcc tacatcggcc tgtcattaat caacgacggc    840
cagtattact ttaatgatga cggcatcatg caggtcgggt ttgtcaccat caacgataaa    900
gtcttctact tctctgactc tggcattatc gagagcgggg tgcagaacat cgacgataac    960
tatttctaca tcgatgacaa tggcattgtc cagatcggcg tgttcgatac gtcagacggt   1020
tataagtatt ttgcgcccgc caacaccgtc aacgataata tctacggtca agctgttgaa   1080
tatagtggtt tggtccgtgt cggtgaagac gtgtactatt tcggcgagac gtacacaatt   1140
gagacgggct ggatctatga tatggagaac gagagtgaca agtactattt caatcctgag   1200
accaagaaag catgcaaggg gatcaacctg atcgatgaca tcaagtacta tttcgacgag   1260
```

```
aagggcatta tgcgcacggg gcttatctca tttgagaata acaattatta cttcaatgag    1320 aacgggaaa tgcagtttgg gtacatcaat attgaggaca agatgttcta ttttggcgag     1380
gatggcgtca tgcagatcgg ggtgttcaac accccagatg gtttcaagta tttcgcgcat    1440
cagaatacgc tggatgagaa cttcgagggc gaatcaatca actataccgg gtggctggac    1500
ctcgatgaga agcgctacta tttcacggac gaatacattg cggccaccgg ctcagtcatc    1560
attgatggcg aggaatacta tttcgaccct gatacggcgc agctggtgat cagtgagtaa    1620
tgacctagg                                                            1629
```

<210> SEQ ID NO 25
<211> LENGTH: 43
<212> TYPE: DNA
<213> ORGANISM: Artificial Sequence
<220> FEATURE:
<223> OTHER INFORMATION: Primer 5rpoS-for

<400> SEQUENCE: 25

```
aagcttgaat tccgtattct gagggctcag gtgaacaaag tgc                      43
```

<210> SEQ ID NO 26
<211> LENGTH: 43
<212> TYPE: DNA
<213> ORGANISM: Artificial Sequence
<220> FEATURE:
<223> OTHER INFORMATION: Primer 5rpoS-rev

<400> SEQUENCE: 26

```
cctaggcaat tgacccgtga tcccttgacg gaactagcaa gtc                      43
```

<210> SEQ ID NO 27
<211> LENGTH: 39
<212> TYPE: DNA
<213> ORGANISM: Artificial Sequence
<220> FEATURE:
<223> OTHER INFORMATION: Primer 3rpoS-for

<400> SEQUENCE: 27

```
ggatccggtt cggtatcgcg ccaggtatac agacaatgc                           39
```

<210> SEQ ID NO 28
<211> LENGTH: 38
<212> TYPE: DNA
<213> ORGANISM: Artificial Sequence
<220> FEATURE:
<223> OTHER INFORMATION: Primer 3rpoS-rev

<400> SEQUENCE: 28

```
ctcgagccgg aagtgcaggc ggtaaacgct atgtacac                            38
```

<210> SEQ ID NO 29
<211> LENGTH: 27
<212> TYPE: DNA
<213> ORGANISM: Artificial Sequence
<220> FEATURE:
<223> OTHER INFORMATION: Primer rpoS PCR-for

<400> SEQUENCE: 29

```
atgcagcaca gcaaggagtt gtgacca                                        27
```

<210> SEQ ID NO 30
<211> LENGTH: 31
<212> TYPE: DNA
<213> ORGANISM: Artificial Sequence

```
<220> FEATURE:
<223> OTHER INFORMATION: Primer rpoS PCR-rev

<400> SEQUENCE: 30
ggtgcgtatc gataaggtct cttaccacag c                                31

<210> SEQ ID NO 31
<211> LENGTH: 3290
<212> TYPE: DNA
<213> ORGANISM: Artificial Sequence
<220> FEATURE:
<223> OTHER INFORMATION: 5guaB-PompC-14CBDA-FRT-3guaA gene cassette

<400> SEQUENCE: 31
gcgctgacca ccggaatacg gctggcaaaa atagcccgcg ccacgcgttc gtcgttaaaa      60
ctccacaaat cttccagcga accgccgccg cgtccgacga tcagcacgtc gcactcgccg     120
cgcgtgtttg ccagttcgat agcacgaacg atctgccccg gcgcatcgtc gccctgtacc     180
gcggttggat agataataac gggcaggat  gggtcacgac gcttcaacac gtggaggata     240
tcgtgcagcg ccgcgccggt tttcgaggtg atcaccccaa cgcagtgggc cggggagggc     300
aacggctgtt tatgctgctg atcgaacaag ccttcggcat ggagtttggc ttttagctgc     360
tcatacttct gctgcaacaa gccttcgcca gccggctgca tactttcggc gatgatttga     420
taatcgccgc gcggctcgta cagcgtaatg ttggcgcgta ccagcacctg ctgcccgtgc     480
tgcgggcgga acgtcacccg gcggttgctg ttgcggaaca tcgcacagcg cacctgagcg     540
gtatcgtctt tgagcgtaaa gtaccagtgg cccgacgcag gctgcgtgaa attagaaatc     600
tcgccgctga tccatacctg tcccatctcc tgttctaaca gcagacgaac cgtctggtta     660
aggcggctta cggtaaaaat tgaggaagtt tgagaggata acatgtgagc gggatcaaat     720
tctaaatcag caggttattc aatcgatagt aacctgctca cggggatcg caagcactat      780 ttgcaaaaaa atgtagatgc aaccgattac gttctgtata atgccgcggc aatatttatt     840
aacctcccag gtgagatatt gccccaattc gtcaattctg tggtagcaca gaataatgaa     900
aagtgtgtaa agaagggtaa aaaaaaccga atgcgaggca tccggttgaa atagggggtaa    960 acagacattc agaaatgaat gacgtaata  aataaagtta atgatgatag cgggagttat    1020
tctagttgcg agtgaaggtt ttgttttgac attcagtgct gtcaaatact taagaataag   1080
ttattgattt taaccttgaa ttattattgc ttgatgttag gtgcttattt cgccattccg   1140
caataatctt aaaaagttcc cttgcattta cattttgaaa catctatagc gataaatgaa   1200
acatcttaaa agttttagta tcatattcgt gttggattat tctgcatttt tggggagaat   1260
ggacttgccg actgattaat gagggttaat cagtatgcag tggcataaaa aagcaaataa   1320
aggcatataa cagatcgatc ttaaacatcc acaggaggat gggatccaaa ataaggagga   1380
aaaaaaaatg actagcaccg gctatacgag catcaacggg aagcatttt  atttcaatac    1440 cgacggcatt atgcagatcg gggtgttcaa agggcccaac ggtttcgaat actttgcgcc   1500
ggccaacacg gatgcgaata acatcgaagg tcaagccatc ctctaccaga acaaattcct   1560
gaccctcaat ggcaagaaat attacttcgg gtccgacagc aaggctgtca cgggtctgcg   1620
cacgattgat gggaaaaagt attacttcaa caccaatact gccgtggcgg tcaccggatg   1680
gcaaacgatc aacggcaaga atatactactt caataccaac acgtccattg cctcgaccgg   1740
gtatacgatc atttccggca aacacttcta cttcaacacc gacggatca  tgcaaatcgg    1800 tgtgtttaaa gggcccgatg gcttcgagta ctttgccccg gcgaatacgg acgccaataa   1860
```

```
cattgaaggt caggcaattc ggtatcagaa tcgtttctc tatctgcatg acaacatcta    1920
ctatttcggt aataacagca aggcggccac cgggtgggtc acgattgatg caaccggta    1980 ttacttcgag cccaatacgg cgatgggggc gaatggttat aaaacgatcg acaacaagaa    2040
tttctacttt cgcaacgggc tcccgcagat tggcgtgttc aaagggtcca acggctttga    2100
gtacttcgcc cccgcgaata cggatgccaa caatatcgag ggccaagcga ttcggtatca    2160
aaaccgcttc ctccacctgc tcgggaaaat ctattacttc ggcaataact cgaaagccgt    2220
cacgggttgg caaacgatta atggcaaagt gtattacttc atgccggata ctgcaatggc    2280
agccgctggt ggattattcg aaattgacgg cgtcatctat ttctttggcg tggatggggt    2340
caaagccccg gggatctatg gctaatgacc tagctgataa cctagcccgc ctaatgagcg    2400 ggctttttt tctcggccta cgctggagc tgcttcgaag ttcctatact ttctagagaa    2460
taggaacttc gaactgcagg tcgacggatc cactagtgtc gataaccctt cctgtgtttt    2520
catgaacagg taaaagtgaa tttaaccctc tgttttttgca gagggttttt atttatgtgc    2580
atagatgcat tttctgtgta gtgcacagct tctggcggca aagcactgca tcgacacaat    2640
agtgggtttc actggcagca cacaatcaaa tctgacagtc ggcttcgagc gaggtgcgga    2700
cattggtagc ttcaacaaca tgactggcat tgaggtgtat taatcaacgg gaagcaggtc    2760
agtttactcc gccagcccga cttttacgaa agggctacca tgactacgcg attttttgat    2820
tagcttgcca acgtataatc ctctgatttc tggtgatgcg attcgtccaa caaattctga    2880
acggttggtt tcgggggggg gatgaccaat tcccgggtaa agtattgctg agagcctgcc    2940
ttcaaccagc actgtatctc gtaaacttcc atcaccaaac cgccgtaggt ggcgtatgca    3000
aattgtaggt tttcatcttt tggtactttt gcccagacgc cacgcgtagc ttcatataat    3060
gcaagtgcac tcatgccaga cttgtaggtg ctgtttagca aaaagcgag cccggcatgt    3120 tcaggtgcga tttccgtctc ttgcttaaga agaagatgat tgagctcatc cagcgtgatt    3180
cgccccataa gggagctgct tcctcgtact ttgttggtca gttctccaac acccaagaga    3240
tcaatacatg ttgcttcaac aagcttcgcg gttgcctcat ccatgccatg               3290

<210> SEQ ID NO 32
<211> LENGTH: 3229
<212> TYPE: DNA
<213> ORGANISM: Artificial Sequence
<220> FEATURE:
<223> OTHER INFORMATION: 5htrA-PompC-14CBDA-FRT-3htrA gene cassette

<400> SEQUENCE: 32
gtgtcgccga tcttgaagac gcggtagaga aagaatctt tagcgttgag cagctttatc      60
accatttata tcacgcgtgg ggccaccatg agaaggattc gctgtttgag ctggtggtag    120
gaaatgcgtg ggaaaaatca cgcgccaata cattaagccg cagtaccgaa gatcagtttt    180
ttatgtattt acgggtaaat acattaaata aactggtgcc ctatgccgct cagcgttta    240 ttgataattt gccgcagatt tttgccggta ccttcaatca ggcgttactg gaagatgcca    300
gcggttttag ccgcctgctt gaactctata agaatgtggc ggttgaacat gtgtttagcc    360
atccggatgt agaacagctt gaactacagg gataccgggt gatcagcggg ttattagata    420
tctatcagcc gctattaagc ttgtcgctta acgactttcg cgagctggtg aaaaagaac    480 ggttgaaacg cttccctata gaatcgcgct tatttcagaa actttctacg cgccatcgtt    540
tggcctacgt ggaagtcgtc agtaaattac ccacggattc ggcggagtac ccggtactgg    600
aatattatta tcgctgtcgg ttgattcagg attatatcag cgggatgact gacctttacg    660
```

-continued

| | |
|---|---|
| catgggatga atatcggcgt tgatggcgg tcgaacagta aatggacttt tgtaaagatg | 720 |
| gacaataaat ttttactttt tccagaaact ttattccgga acttcgcgtt ataaaatgaa | 780 |
| tctgacgtac acagcaattt tgcgttacct gttaatcgca attcgtcaat tctgtggtag | 840 |
| cacagaataa tgaaagtgt gtaaagaagg gtaaaaaaaa ccgaatgcga ggcatccggt | 900 |
| tgaaataggg gtaaacagac attcagaaat gaatgacggt aataaataaa gttaatgatg | 960 |
| atagcgggag ttattctagt tgcgagtgaa ggttttgttt tgacattcag tgctgtcaaa | 1020 |
| tacttaagaa taagttattg attttaacct tgaattatta ttgcttgatg ttaggtgctt | 1080 |
| atttcgccat tccgcaataa tcttaaaaag ttcccttgca tttacatttt gaaacatcta | 1140 |
| tagcgataaa tgaaacatct aaaagttttt agtatcatat tcgtgttgga ttattctgca | 1200 |
| tttttgggga gaatggactt gccgactgat taatgagggt taatcagtat gcagtggcat | 1260 |
| aaaaaagcaa ataaaggcat ataacagatc gatcttaaac atccacagga ggatgggatc | 1320 |
| caaaataagg aggaaaaaaa aatgactagc accggctata cgagcatcaa cgggaagcat | 1380 |
| ttttatttca ataccgacgg cattatgcag atcgggtgt tcaaagggcc caacggtttc | 1440 |
| gaatactttg cgccggccaa cacggatgcg aataacatcg aaggtcaagc catcctctac | 1500 |
| cagaacaaat tcctgaccct caatggcaag aaatattact tcgggtccga cagcaaggct | 1560 |
| gtcacgggtc tgcgcacgat tgatgggaaa aagtattact tcaacaccaa tactgccgtg | 1620 |
| gcggtcaccg gatggcaaac gatcaacggc aagaaatact acttcaatac caacacgtcc | 1680 |
| attgcctcga ccgggtatac gatcatttcc ggcaaacact tctacttcaa caccgacggg | 1740 |
| atcatgcaaa tcggtgtgtt taaagggccc gatggcttcg agtactttgc cccggcgaat | 1800 |
| acggacgcca ataacattga aggtcaggca attcggtatc agaatcgttt tctctatctg | 1860 |
| catgacaaca tctactattt cggtaataac agcaaggcgg ccaccgggtg ggtcacgatt | 1920 |
| gatggcaacc ggtattactt cgagcccaat acggcgatgg gggcgaatgg ttataaaacg | 1980 |
| atcgacaaca agaatttcta ctttcgcaac gggctcccgc agattggcgt gttcaaaggg | 2040 |
| tccaacggct ttgagtactt cgcccccgcg aatacggatg ccaacaatat cgagggccaa | 2100 |
| gcgattcggt atcaaaaccg cttcctccac ctgctcggga aaatctatta cttcggcaat | 2160 |
| aactcgaaag ccgtcacggg ttggcaaacg attaatggca aagtgtatta cttcatgccg | 2220 |
| gatactgcaa tggcagccgc tgtggatta ttcgaaattg acggcgtcat ctatttctt | 2280 |
| ggcgtggatg gggtcaaagc cccggggatc tatggctaat gacctagctg ataacctagc | 2340 |
| ccgcctaatg agcgggcttt ttttttctcgg cctagcgctg gagctgcttc gaagttccta | 2400 |
| tactttctag agaataggaa cttcgaactg caggtcgacg gatccactag tctgcgtaag | 2460 |
| attctcgaca gcaagccgtc ggtgctggcg ctgaatattc agcgtggtga tagttctatt | 2520 |
| tatttgctga tgcagtaatc acctttgtcc cccttccacc acggaagggg gcaacacttt | 2580 |
| tctgtgaaac tccccacaac tccatacttc tttgcaccgt tttgtgcatt tgcacaatgt | 2640 |
| cgaggcctgt catcttcctt atgcttgtgc tctgctcaca ggaggattt atggctggct | 2700 |
| ggcatcttga taccaaaatg gcgcaggata tcgtggcgcg cactatgcgc atcatcgata | 2760 |
| ccaatatcaa cgtaatggat gcccgcggc gtattatcgg cagcggcgat cgggaacgta | 2820 |
| ttggtgaatt gcacgaaggc gcgttgttag tgctgtcaca gggccgggtt gtggatatcg | 2880 |
| acaacgccgt ggcgcgacac ctgcacgggg tgcgtcaggg gattaatctt cccttacgcc | 2940 |
| ttgagggcga aattgttggc gtgatcgtc tcaccggcga accagagcat ctgcgtaaat | 3000 |
| atggcgaact ggtgtgtatg actgccgaaa tgatgctgga acagtcgcgg ttaatgcacc | 3060 |

```
ttttggcgca ggatagccgt tgcgtgaag agctggtgat gaacctgatt caggccgaag      3120
aaaatacgcc ggcgctggtg aatgggcac agcgtttagg gatcgatttg aaccagccgc      3180
gtgtggcggc ggtggtggaa gtcgacagcg gccagcttgg cgtcgatag                 3229

<210> SEQ ID NO 33
<211> LENGTH: 2982
<212> TYPE: DNA
<213> ORGANISM: Artificial Sequence
<220> FEATURE:
<223> OTHER INFORMATION: 5rpoS-PompC-14CBDA-FRT-3rpoS gene cassette

<400> SEQUENCE: 33
atgcagcaca gcaaggagtt gtgaccaggt ctgcacaaaa ttccaccgtt gcagttgcgt        60
ctcaaccaac aattacgtat tctgagggct caggtgaaca agtgctaac aaaatgttgc       120 caaacaacaa gcctgctggg acggttgtca cagcgcctgt aacggcacca acggtaagca       180
cgaccgaacc aaatgcaagc agtacgtcaa ccagcgcgcc gatttccgca tggcgctggc       240
cgacggatgg caaagtgatc gaaaactttg gcgcttccga agggggcaat aaagggatcg       300
acattgcagg cagtaaggga caggctatcg tcgcaaccgc tgatgggcgc gtcgtatatg       360
ccggtaacgc actgcgtggt tacgtaatc ttattatcat caaacataac gatgattacc       420
tgagtgccta cgcccataat gatacgatgc tggtccggga acaacaggaa gttaaggcgg       480
ggcaaaaaat cgctactatg ggtagcaccg gcaccagctc tacacgcttg cattttgaaa       540
ttcgttacaa ggggaaatcc gtaaacccgc tgcgttattt accgcagcga taaagcggcg       600
gaaccaggct ttgacttgct agttccgtca agggatcacg ggtcaattcg tcaattctgt       660
ggtagcacag aataatgaaa agtgtgtaaa gaagggtaaa aaaaaccgaa tgcgaggcat       720
ccggttgaaa taggggtaaa cagacattca gaaatgaatg acgtaataa ataaagttaa       780 tgatgatagc gggagttatt ctagttgcga gtgaaggttt tgttttgaca ttcagtgctg       840
tcaaatactt aagaataagt tattgatttt aaccttgaat tattattgct tgatgttagg       900
tgcttatttc gccattccgc aataatctta aaaagttccc ttgcatttac attttgaaac       960
atctatagcg ataaatgaaa catcttaaaa gttttagtat catattcgtg ttggattatt      1020
ctgcattttt ggggagaatg gacttgccga ctgattaatg agggttaatc agtatgcagt      1080
ggcataaaaa agcaaataaa ggcatataac agatcgatct taaacatcca caggaggatg      1140
ggatccaaaa taaggaggaa aaaaaatga ctagcaccgg ctatacgagc atcaacggga      1200 agcatttta tttcaatacc gacggcatta tgcagatcgg ggtgttcaaa gggcccaacg      1260
gtttcgaata ctttgcgccg ccaacacgg atgcgaataa catcgaaggt caagccatcc      1320
tctaccagaa caaattcctg accctcaatg caagaaata ttacttcggg tccgacagca      1380
aggctgtcac gggtctgcgc acgattgatg ggaaaaagta ttacttcaac accaatactg      1440
ccgtggcggt caccggatgg caaacgatca acggcaagaa atactacttc aataccaaca      1500
cgtccattgc ctcgaccggg tatacgatca tttccggcaa acacttctac ttcaacaccg      1560 acggatcat gcaaatcggt gtgtttaaag ggcccgatgg cttcgagtac tttgccccgg      1620
cgaatacgga cgccaataac attgaaggtc aggcaattcg gtatcagaat cgttttctct      1680
atctgcatga caacatctac tatttcggta ataacagcaa ggcggccacc gggtgggtca      1740
cgattgatgg caaccggtat tacttcgagc ccaatacggc gatggggcg aatggttata      1800 aaacgatcga caacaagaat ttctactttc gcaacgggct cccgcagatt ggcgtgttca      1860
aagggtccaa cggctttgag tacttcgccc ccgcgaatac ggatgccaac aatatcgagg      1920
```

```
gccaagcgat tcggtatcaa aaccgcttcc tccacctgct cgggaaaatc tattacttcg   1980
gcaataactc gaaagccgtc acgggttggc aaacgattaa tggcaaagtg tattacttca   2040
tgccggatac tgcaatggca gccgctggtg gattattcga aattgacggc gtcatctatt   2100
tctttggcgt ggatggggtc aaagccccgg ggatctatgg ctaatgacct agctgataac   2160
ctagcccgcc taatgagcgg gctttttttt ctcggcctag cgacgaattg cctagcgctg   2220
gagctgcttc gaagttccta tactttctag agaataggaa cttcgaactg caggtcgacg   2280
gatccggttc ggtatcgcgc caggtataca gacaatgctg acactgatat accgtccaga   2340
ctccttttac cggcgaagtc gccatgagtt caatatgtgc atcggcacag cgtggacaaa   2400
tcatcggtta ctccttattt acggttggcc agcatggcgg tcagcttttc agcccaggct   2460
ttagtttccg gtaaatccac aaccggctgg ctatagtgac cacggttatc tggcgcaacc   2520
ggcgtggtag cgtcaatgat cagtttgtcg gtaatccccg ccgggcttga acccgggtcc   2580
agttccagga cggacatatt cggtagctgt accagatcgc ctgccggatt cactttcgac   2640
gacaacgccc acatcacctg tggcagatta aatggatcga catcttcatc aaccatgatc   2700
accatcttca catatcccag accgtgcggc gtcgtcatcg cgcgcaggcc caccgcacgg   2760
gcaaagccgc cgtagcgttt tttggtcgag atgatggcca gcaagccgtg ggtgtacata   2820
gcgtttaccg cctgcacttc cggaaattcg ctttcagct gttgatacag tggcacacag   2880
gtcgccggcc ccatcaggta gtcgatttcc gtccacggca tccccaaata gagcgattca   2940
aaaatgggtt tgctgtggta agagaccta tcgatacgca cc                      2982
```

<210> SEQ ID NO 34
<211> LENGTH: 325
<212> TYPE: PRT
<213> ORGANISM: Clostridium difficile

<400> SEQUENCE: 34

Met Thr Ser Thr Gly Tyr Thr Ser Ile Asn Gly Lys His Phe Tyr Phe
1               5                   10                  15

Asn Thr Asp Gly Ile Met Gln Ile Gly Val Phe Lys Gly Pro Asn Gly
            20                  25                  30

Phe Glu Tyr Phe Ala Pro Ala Asn Thr Asp Ala Asn Asn Ile Glu Gly
        35                  40                  45

Gln Ala Ile Leu Tyr Gln Asn Lys Phe Leu Thr Leu Asn Gly Lys Lys
    50                  55                  60

Tyr Tyr Phe Gly Ser Asp Ser Lys Ala Val Thr Gly Leu Arg Thr Ile
65                  70                  75                  80

Asp Gly Lys Lys Tyr Tyr Phe Asn Thr Asn Thr Ala Val Ala Val Thr
                85                  90                  95

Gly Trp Gln Thr Ile Asn Gly Lys Lys Tyr Tyr Phe Asn Thr Asn Thr
            100                 105                 110

Ser Ile Ala Ser Thr Gly Tyr Thr Ile Ile Ser Gly Lys His Phe Tyr
        115                 120                 125

Phe Asn Thr Asp Gly Ile Met Gln Ile Gly Val Phe Lys Gly Pro Asp
    130                 135                 140

Gly Phe Glu Tyr Phe Ala Pro Ala Asn Thr Asp Ala Asn Asn Ile Glu
145                 150                 155                 160

Gly Gln Ala Ile Arg Tyr Gln Asn Arg Phe Leu Tyr Leu His Asp Asn
                165                 170                 175

Ile Tyr Tyr Phe Gly Asn Asn Ser Lys Ala Ala Thr Gly Trp Val Thr
            180                 185                 190

```
Ile Asp Gly Asn Arg Tyr Tyr Phe Glu Pro Asn Thr Ala Met Gly Ala
            195                 200                 205

Asn Gly Tyr Lys Thr Ile Asp Asn Lys Asn Phe Tyr Phe Arg Asn Gly
    210                 215                 220

Leu Pro Gln Ile Gly Val Phe Lys Gly Ser Asn Gly Phe Glu Tyr Phe
225                 230                 235                 240

Ala Pro Ala Asn Thr Asp Ala Asn Asn Ile Glu Gly Gln Ala Ile Arg
                245                 250                 255

Tyr Gln Asn Arg Phe Leu His Leu Leu Gly Lys Ile Tyr Tyr Phe Gly
            260                 265                 270

Asn Asn Ser Lys Ala Val Thr Gly Trp Gln Thr Ile Asn Gly Lys Val
    275                 280                 285

Tyr Tyr Phe Met Pro Asp Thr Ala Met Ala Ala Gly Gly Leu Phe
290                 295                 300

Glu Ile Asp Gly Val Ile Tyr Phe Phe Gly Val Asp Gly Val Lys Ala
305                 310                 315                 320

Pro Gly Ile Tyr Gly
            325

<210> SEQ ID NO 35
<211> LENGTH: 1542
<212> TYPE: DNA
<213> ORGANISM: Artificial Sequence
<220> FEATURE:
<223> OTHER INFORMATION: ssb region of chromosomal deletion

<400> SEQUENCE: 35
ttcggcggat cggagagatc gcagacttcg ccgtcaatac gggcgcgaat gtaaccctgg      60
cttgccagat tttccagcgt tttggtgtgt tcgcctttac gctctttaat aatcggcgcc     120
agcagcatca ggcgtttgcc ttccggctgc gacagcacgt tatcgaccat ctggctaacg     180
gtttgcgccg ccagcggcac gtcatggtcc ggacaacgcg gctcgcccac gcgggcaaac     240
agcaggcgca ggtagtcgtg gatctcggta atagtaccca ccgtagagcg cgggttgtgc     300
gatgtcgatt tctgttcaat tgagatcgcg ggcgatagcc cctcaatatg gtcgacatcc     360
ggtttttcca tgagcgacaa aaactgccgc gcgtaagcgg agagcgattc aacgtaacga     420
cgctgccctt cggcatacag agtgtcgaaa gccagtgagg atttgcctga acccgaaagc     480
ccggtcacga caatcagttt gtcgcggggg atgacgaggt taatattttt gagattatgg     540
gtgcgggcgc cccgaacttc gatcttatcc attcaccttt cccggtagag actcggatgc     600
ctggtttgtt tgaaggacaa acggcagaaa cggctaatta tgacacaatt taacctgttt     660
gaatatacag tagctagcgt gtaggctgga gctgcttcga agttcctata ctttctagag     720
aataggaact tcggaatagg aactaaggag gatattcata tgcattttcg ctatagttct     780
cgtctgctga atgcctggt gtaaaccagg catttatta cctggtatta ttgtcttagt      840 atcccttca aaaagagaa gcgcatatct cacggaatga cttacggaaa aatgtcgctt      900
atcgcctctg gccgactcgc ctcggcacat cattatccag ccgaagttca taaatgtact     960
gcaataaccc ggattgtctt aaatatgaaa gagaaatctc atctgcaaaa tatataattt    1020
atagccattt tttgacaaca aaaagatatt ataaataac ggtagagaat ggtcggtatt     1080
atcaatagtt aattaaatgc ttgctttagc ttgtgatgag ctcaaatatg atatgtgtat    1140
cttgctttat tttaattgc tgaagataaa attgttactt atagctggct ttatataaaa     1200
aatggtttta tttgtgtatt tttttacaca attctgattt tttactcccc acttattata    1260
```

```
ttttcaatga tttaagttat attgaagtcc ctatgaccct atgttttaat tgtgaaaatt    1320
cattttatcc tctggaggca aatttattaa atacgtatgg ttataacgcg tattaaaaag    1380
aaatatgtcc ttaaaatgat ttagagtttc aatgattagc taacaaatct atttatcggc    1440
gggtggtttt aatttgctga tgactatttt ttatttatga gctgagagct tatgcgatac    1500
ctattattgg ggaagatata gttagtgcaa taattgatgt ct                       1542
```

<210> SEQ ID NO 36
<211> LENGTH: 8045
<212> TYPE: DNA
<213> ORGANISM: Artificial Sequence
<220> FEATURE:
<223> OTHER INFORMATION: PompC-clyA-cbd/b cassette

<400> SEQUENCE: 36

```
gaattctgtg gtagcacaga ataatgaaaa gtgtgtaaag aagggtaaaa aaaaccgaat      60
gcgaggcatc cggttgaaat aggggtaaac agacattcag aaatgaatga cggtaataaa     120
taaagttaat gatgatagcg ggagttattc tagttgcgag tgaaggtttt gttttgacat     180
tcagtgctgt caaatactta agaataagtt attgatttta accttgaatt attattgctt     240
gatgttaggt gcttatttcg ccattccgca ataatcttaa aaagttccct tgcatttaca     300
ttttgaaaca tctatagcga taaatgaaac atcttaaaag ttttagtatc atattcgtgt     360
tggattattc tgcattttg gggagaatgg acttgccgac tgattaatga gggttaatca     420
gtatgcagtg gcataaaaaa gcaaataaag gcatataaca gatcgatctt aaacatccac     480
aggaggatgg gatccaaaat aaggaggaaa aaaaatgac tagtatttt gcagaacaaa      540 ctgtagaggt agttaaaagc gcgatcgaaa ccgcagatgg ggcattagat ctttataaca     600
aatacctcga ccaggtcatc ccctggaaga cctttgatga aaccataaaa gagttaagcc     660
gttttaaaca ggagtactcg caggaagctt ctgttttagt tggtgatatt aaagttttgc     720
ttatggacag ccaggacaag tattttgaag cgacacaaac tgtttatgaa tggtgtggtg     780
tcgtgacgca attactctca gcgtatattt tactatttga tgaatataat gagaaaaaag     840
catcagccca gaaagacatt ctcattagga tattagatga tggtgtcaag aaactgaatg     900
aagcgcaaaa atctctcctg acaagttcac aaagtttcaa caacgcttcc ggaaaactgc     960
tggcattaga tagccagtta actaatgatt tttcggaaaa aagtagttat ttccagtcac    1020
aggtggatag aattcgtaag gaagcttatg ccggtgctgc agccggcata gtcgccggtc    1080
cgtttggatt aattatttcc tattctattg ctgcgggcgt gattgaaggg aaattgattc    1140
cagaattgaa taacaggcta aaaacagtgc aaaatttctt tactagctta tcagctacag    1200
tgaaacaagc gaataaagat atcgatgcgg caaaattgaa attagccact gaaatagcag    1260
caattgggga gataaaaacg gaaaccgaaa caaccagatt ctacgttgat tatgatgatt    1320
taatgctttc tttattaaaa ggagctgcaa agaaaatgat taacacctgt aatgaatacc    1380
aacaacgtca tggtaagaag acgcttttcg aggttcctga cgtcgctagc ggcctgatct    1440
atattaacga ttcactgtac tatttcaagc cgcccgtcaa taacctcatc accgggtttg    1500
tgacggtcgg cgacgataaa tactacttca atccgatcaa cggcgagcc gcgagcattg     1560 gggagaccat cattgatgac aagaattatt acttcaacca gagtggcgtg ctgcagacgg    1620
gggtcttcag taccgaggac ggctttaaat acttcgcccc cgcgaatacg ctcgatgaga    1680
acctggaagg ggaggcgatt gactttaccg gcaagctgat cattgacgag aacatctact    1740
atttcgatga caattaccgc ggggccgtgg aatggaagga gctcgatggc gagatgcact    1800
```

```
attttagccc ggagacgggg aaagctttca aaggcctgaa tcaaattggg gactacaagt    1860
attacttcaa ctctgacggt gtgatgcaga aggggttcgt gagtatcaat gacaacaagc    1920
attatttcga cgattctggc gtcatgaaag tggggtacac cgagatcgat ggcaagcact    1980
tctactttgc cgagaatggt gagatgcaaa tcggcgtgtt caatacggaa gacgggttta    2040
agtatttcgc gcatcataac gaggatctcg gcaatgaaga gggcgaagag atctcatatt    2100
ccggaatcct caacttcaat aacaagattt actactttga tgactcattt accgccgtgg    2160
tcggctggaa ggacctcgag gatgggtcaa agtactattt cgacgaggat acggcggagg    2220
cctacatcgg cctgtcatta atcaacgacg gccagtatta ctttaatgat gacggcatca    2280
tgcaggtcgg gtttgtcacc atcaacgata aagtcttcta cttctctgac tctggcatta    2340
tcgagagcgg ggtgcagaac atcgacgata actatttcta catcgatgac aatggcattg    2400
tccagatcgg cgtgttcgat acgtcagacg gttataagta ttttgcgccc gccaacaccg    2460
tcaacgataa tatctacggt caagctgttg aatatagtgg tttggtccgt gtcggtgaag    2520
acgtgtacta tttcggcgag acgtacacaa ttgagacggg ctggatctat gatatggaga    2580
acgagagtga caagtactat ttcaatcctg agaccaagaa agcatgcaag gggatcaacc    2640
tgatcgatga catcaagtac tatttcgacg agaagggcat tatgcgcacg gggcttatct    2700
catttgagaa taacaattat tacttcaatg agaacgggga aatgcagttt gggtacatca    2760
atattgagga caagatgttc tattttggcg aggatgcgt catgcagatc ggggtgttca    2820
acaccccaga tggtttcaag tatttcgcgc atcagaatac gctggatgag aacttcgagg    2880
gcgaatcaat caactatacc gggtggctgg acctcgatga gaagcgctac tatttcacgg    2940
acgaatacat tgcggccacc ggctcagtca tcattgatgg cgaggaatac tatttcgacc    3000
ctgatacggc gcagctggtg atcagtgagt aatgacctag ctgataacct agcccgccta    3060
atgagcgggc ttttttttct cggcctaggt ttcacctgtt ctattaggtg ttacatgctg    3120
ttcatctgtt acattgtcga tctgttcatg gtgaacagct ttaaatgcac caaaaactcg    3180
taaaagctct gatgtatcta tctttttttac accgttttca tctgtgcata tggacagttt    3240
tccctttgat atctaacggt gaacagttgt tctacttttg tttgttagtc ttgatgcttc    3300
actgatagat acaagagcca taagaacctc agatccttcc gtatttagcc agtatgttct    3360
ctagtgtggt tcgttgtttt tgcgtgagcc atgagaacga accattgaga tcatgcttac    3420
tttgcatgtc actcaaaaat tttgcctcaa aactggtgag ctgaattttt gcagttaaag    3480
catcgtgtag tgttttctt agtccgttac gtaggtagga atctgatgta atggttgttg    3540 gtatttgtc accattcatt tttatctggt tgttctcaag ttcggttacg agatccattt    3600
gtctatctag ttcaacttgg aaaatcaacg tatcagtcgg gcggcctcgc ttatcaacca    3660
ccaatttcat attgctgtaa gtgtttaaat ctttacttat tggtttcaaa acccattggt    3720
taagcctttt aaactcatgg tagttatttt caagcattaa catgaactta aattcatcaa    3780
ggctaatctc tatatttgcc ttgtgagttt tcttttgtgt tagttctttt aataaccact    3840
cataaatcct catagagtat ttgttttcaa aagacttaac atgttccaga ttatatttta    3900 tgaattttt taactggaaa agataaggca atatctcttc actaaaaact aattctaatt    3960
tttcgcttga gaacttggca tagtttgtcc actggaaaat ctcaaagcct ttaaccaaag    4020
gattcctgat ttccacagtt ctcgtcatca gctctctggt tgctttagct aatacaccat    4080
aagcattttc cctactgatg ttcatcatct gagcgtattg gttataagtg aacgataccg    4140
tccgttcttt ccttgtaggg ttttcaatcg tgggggttgag tagtgccaca cagcataaaa    4200
```

```
ttagcttggt ttcatgctcc gttaagtcat agcgactaat cgctagttca tttgctttga    4260
aaacaactaa ttcagacata catctcaatt ggtctaggtg attttaatca ctataccaat    4320
tgagatgggc tagtcaatga taattactag ctagtccttt tcctttgagt tgtgggtatc    4380
tgtaaattct gctagacctt tgctggaaaa cttgtaaatt ctgctagacc ctctgtaaat    4440
tccgctagac ctttgtgtgt ttttttttgtt tatattcaag tggttataat ttatagaata    4500
aagaaagaat aaaaaaagat aaaaagaata gatcccagcc ctgtgtataa ctcactactt    4560
tagtcagttc cgcagtatta caaaaggatg tcgcaaacgc tgtttgctcc tctacaaaac    4620
agaccttaaa accctaaagg cttaagtagc accctcgcaa gctcgggcaa atcgctgaat    4680
attccttttg tctccgacca tcaggcacct gagtcgctgt cttttttcgtg acattcagtt    4740
cgctgcgctc acggctctgg cagtgaatgg gggtaaatgg cactacaggc gccttttatg    4800
gattcatgca aggaaactac ccataataca agaaaagccc gtcacgggct tctcagggcg    4860
ttttatggcg ggtctgctat gtggtgctat ctgacttttt gctgttcagc agttcctgcc    4920
ctctgatttt ccagtctgac cacttcggat tatcccgtga caggtcattc agactggcta    4980
atgcacccag taaggcagcg gtatcatcaa caggcttacc cgtcttactg tcaaccggat    5040
ctaaaacact aggcccaaga gtttgtagaa acgcaaaaag gccatccgtc aggatggcct    5100
tctgcttaat ttgatgcctg gcagtttatg gcgggcgtcc tgcccgccac cctccgggcc    5160
gttgcttcgc aacgttcaaa tccgctcccg gcggatttgt cctactcagg agagcgttca    5220
ccgacaaaca acagataaaa cgaaaggccc agtctttcga ctgagccttt cgttttattt    5280
gatgcctggc agttccctac tctcgcatgg ggagaccca cactaccatc ggcgctacgg    5340
cgtttcactt ctgagttcgg catggggtca ggtgggacca ccgcgctact gccgccaggc    5400
aaattctgtt ttatcagacc gcttctgcgt tctgatttaa tctgtatcag gctgaaaatc    5460
ttctctcatc cgccaaaaca gccaagctgg atctaaaaca ctagctctag ctattgtttt    5520
aatgacaaat cagaacggaa tgtcatcatc aaagtccatc ggcggctcgt tagacgcgc    5580
tgccggagcg gactgctgcg ggcgagactg cgcgccgccg ctgaactgat tgccaccctg    5640
cggctgctga ggctgacccc aaccgccctg cggctgacca ccaccgatat tgccacctgc    5700
cggagcgcca ccaccctgac gaccacccag catctgcatg gtgccgccaa cgttcaccac    5760
gacttctgtg gtgtagcgat cctgaccgga ttgatcggtc catttacggg tacgcagctg    5820
accttcgata taaacctgag aacctttacg cagatattcg ctcgccactt ctgccagttt    5880
gccgaacagc acaacgcggt gccattcagt ctgttctttc atctcgccgg tcgctttatc    5940
acgccaggat tcggaagtag ccagcgtaat gttggcaact gcgccaccat ttggcatgta    6000
gcgtacttcc gggtcctgac ccagattacc aacgagaata accttgttta cgcctctgct    6060
ggccatgttc gtgtctcctg aaaaaaatcg ttctgaataa gtgtaaacgc gcgattgtac    6120
cattaccaat agcgctttta ctatgttgtg acctcggttc cgggaaacaa acctggccag    6180
acattgttac acaacactcc ggataatgca ttccaatact gtatattcat tcaggtcaat    6240
catatgaagg gcgaattctg cagatatcca tcacactggc ggccgccagt gtgatggata    6300
tctgcagaat tcgcccttga aagttcctat tctatatat agtataggaa cttctctaga    6360
acttttgtta cccgccaaac aaaacccaaa acaaccccat acccaaccca ataaaacacc    6420
aaaacaagac aaataatcat tgattgatgg ttgaaatggg gtaaacttga caaacaaacc    6480
cacttaaaac ccaaaacata cccaaacaca caccaaaaaa acaccataag gagttttata    6540
aatgttggta ttcattgatg acggttcaac aaacatcaaa ctacagtggc aggaaagcga    6600
```

-continued

```
cggaacaatt aaacagcaca ttagcccgaa cagcttcaaa cgcgagtggg cagtctcttt    6660
tggtgataaa aaggtcttta actacacact gaacggcgaa cagtattcat ttgatccaat    6720
cagcccggat gctgtagtca caaccaatat cgcatggcaa tacagcgacg ttaatgtcgt    6780
tgcagtgcat cacgccttac tgaccagtgg tctgccggta agcgaagtgg atattgtttg    6840
cacacttcct ctgacagagt attacgacag aaataaccaa cccaatacgg aaaatattga    6900
gcgtaagaaa gcaaacttcc ggaaaaaaat tacattaaat ggcggggata cattcacaat    6960
aaaagatgta aaagtcatgc ctgaatctat accggcaggt tatgaagttc tacaagaact    7020
ggatgagtta gattctttat taattataga tctcgggggc accacattag atatttctca    7080
ggtaatgggg aaattatcgg ggatcagtaa aatatacgga gactcatctc ttggtgtctc    7140
tctggttaca tctgcagtaa aagatgccct ttctcttgcg agaacaaaag gaagtagcta    7200
tcttgctgac gatataatca ttcacagaaa agataataac tatctgaagc aacgaattaa    7260
tgatgagaac aaaatatcaa tagtcaccga agcaatgaat gaagcacttc gtaaacttga    7320
gcaacgtgta ttaaatacgc tcaatgaatt ttctggttat actcatgtta tggttatagg    7380
cggtggcgca gaattaatat gcgatgcagt aaaaaaacac acacagattc gtgatgaacg    7440
ttttttcaaa accaataact ctcaatatga tttagttaac ggtatgtatc tcataggtaa    7500
ttaatgatgg acaagcgcag aaccattgcc ttcaaactaa atccagatgt aaatcaaaca    7560
gataaaattg tttgtgatac actggacagt atcccgcaag gggaacgaag ccgccttaac    7620
cgggccgcac tgacggcagg tctggcctta tacagacaag atccccggac ccctttcctt    7680
ttatgtgagc tgctgacgaa agaaaccaca ttttcagata tcgtgaatat attgagatcg    7740
ctatttccaa aagagatggc cgattttaat tcttcaatag tcactcaatc ctcttcacaa    7800
caagagcaaa aaagtgatga agagaccaaa aaaaatgcga tgaagctaat aaattaattc    7860
aattattatt gagttccctt tatccactat caggctggat aaagggaact caatcaagtt    7920
attttcttac cagtcattac ataatcgtta ttatgaaata atcgtttgca ctgtctctgt    7980
tattcaggca atttcaataa aggcacttgc tcacgctctg tcattttctg aaactcttca    8040
tgctg                                                                8045
```

<210> SEQ ID NO 37
<211> LENGTH: 838
<212> TYPE: PRT
<213> ORGANISM: Artificial Sequence
<220> FEATURE:
<223> OTHER INFORMATION: Amino acid sequence of ClyA-CBD/B

<400> SEQUENCE: 37

```
Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95
```

```
Tyr Ile Leu Leu Phe Asp Glu Tyr Asn Glu Lys Lys Ala Ser Ala Gln
            100                 105                 110

Lys Asp Ile Leu Ile Arg Ile Leu Asp Asp Gly Val Lys Lys Leu Asn
    115                 120                 125

Glu Ala Gln Lys Ser Leu Leu Thr Ser Ser Gln Ser Phe Asn Asn Ala
130                 135                 140

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
                165                 170                 175

Ala Tyr Ala Gly Ala Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
            195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
            260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val Ala
    290                 295                 300

Ser Gly Leu Ile Tyr Ile Asn Asp Ser Leu Tyr Tyr Phe Lys Pro Pro
305                 310                 315                 320

Val Asn Asn Leu Ile Thr Gly Phe Val Thr Val Gly Asp Asp Lys Tyr
                325                 330                 335

Tyr Phe Asn Pro Ile Asn Gly Gly Ala Ala Ser Ile Gly Glu Thr Ile
            340                 345                 350

Ile Asp Asp Lys Asn Tyr Tyr Phe Asn Gln Ser Gly Val Leu Gln Thr
        355                 360                 365

Gly Val Phe Ser Thr Glu Asp Gly Phe Lys Tyr Phe Ala Pro Ala Asn
    370                 375                 380

Thr Leu Asp Glu Asn Leu Glu Gly Glu Ala Ile Asp Phe Thr Gly Lys
385                 390                 395                 400

Leu Ile Ile Asp Glu Asn Ile Tyr Tyr Phe Asp Asp Asn Tyr Arg Gly
                405                 410                 415

Ala Val Glu Trp Lys Glu Leu Asp Gly Glu Met His Tyr Phe Ser Pro
            420                 425                 430

Glu Thr Gly Lys Ala Phe Lys Gly Leu Asn Gln Ile Gly Asp Tyr Lys
        435                 440                 445

Tyr Tyr Phe Asn Ser Asp Gly Val Met Gln Lys Gly Phe Val Ser Ile
    450                 455                 460

Asn Asp Asn Lys His Tyr Phe Asp Asp Ser Gly Val Met Lys Val Gly
465                 470                 475                 480

Tyr Thr Glu Ile Asp Gly Lys His Phe Tyr Phe Ala Glu Asn Gly Glu
                485                 490                 495

Met Gln Ile Gly Val Phe Asn Thr Glu Asp Gly Phe Lys Tyr Phe Ala
            500                 505                 510
```

His His Asn Glu Asp Leu Gly Asn Glu Glu Gly Glu Ile Ser Tyr
            515                 520                 525

Ser Gly Ile Leu Asn Phe Asn Lys Ile Tyr Tyr Phe Asp Ser
        530                 535                 540

Phe Thr Ala Val Val Gly Trp Lys Asp Leu Glu Asp Gly Ser Lys Tyr
545                 550                 555                 560

Tyr Phe Asp Glu Asp Thr Ala Glu Ala Tyr Ile Gly Leu Ser Leu Ile
                565                 570                 575

Asn Asp Gly Gln Tyr Tyr Phe Asn Asp Gly Ile Met Gln Val Gly
            580                 585                 590

Phe Val Thr Ile Asn Asp Lys Val Phe Tyr Phe Ser Asp Ser Gly Ile
            595                 600                 605

Ile Glu Ser Gly Val Gln Asn Ile Asp Asp Asn Tyr Phe Tyr Ile Asp
            610                 615                 620

Asp Asn Gly Ile Val Gln Ile Gly Val Phe Asp Thr Ser Asp Gly Tyr
625                 630                 635                 640

Lys Tyr Phe Ala Pro Ala Asn Thr Val Asn Asp Asn Ile Tyr Gly Gln
                645                 650                 655

Ala Val Glu Tyr Ser Gly Leu Val Arg Val Gly Glu Asp Val Tyr Tyr
            660                 665                 670

Phe Gly Glu Thr Tyr Thr Ile Glu Thr Gly Trp Ile Tyr Asp Met Glu
            675                 680                 685

Asn Glu Ser Asp Lys Tyr Tyr Phe Asn Pro Glu Thr Lys Lys Ala Cys
            690                 695                 700

Lys Gly Ile Asn Leu Ile Asp Asp Ile Lys Tyr Tyr Phe Asp Glu Lys
705                 710                 715                 720

Gly Ile Met Arg Thr Gly Leu Ile Ser Phe Glu Asn Asn Tyr Tyr
            725                 730                 735

Phe Asn Glu Asn Gly Glu Met Gln Phe Gly Tyr Ile Asn Ile Glu Asp
            740                 745                 750

Lys Met Phe Tyr Phe Gly Glu Asp Gly Val Met Gln Ile Gly Val Phe
            755                 760                 765

Asn Thr Pro Asp Gly Phe Lys Tyr Phe Ala His Gln Asn Thr Leu Asp
            770                 775                 780

Glu Asn Phe Glu Gly Glu Ser Ile Asn Tyr Thr Gly Trp Leu Asp Leu
785                 790                 795                 800

Asp Glu Lys Arg Tyr Tyr Phe Thr Asp Glu Tyr Ile Ala Ala Thr Gly
                805                 810                 815

Ser Val Ile Ile Asp Gly Glu Glu Tyr Tyr Phe Asp Pro Asp Thr Ala
            820                 825                 830

Gln Leu Val Ile Ser Glu
        835

<210> SEQ ID NO 38
<211> LENGTH: 305
<212> TYPE: PRT
<213> ORGANISM: Salmonella typhi

<400> SEQUENCE: 38

Met Thr Ser Ile Phe Ala Glu Gln Thr Val Glu Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

```
Arg Phe Lys Gln Glu Tyr Ser Gln Glu Ala Ser Val Leu Val Gly Asp
 50                  55                  60
Ile Lys Val Leu Leu Met Asp Ser Gln Asp Lys Tyr Phe Glu Ala Thr
 65                  70                  75                  80
Gln Thr Val Tyr Glu Trp Cys Gly Val Val Thr Gln Leu Leu Ser Ala
                 85                  90                  95
Tyr Ile Leu Leu Phe Asp Glu Tyr Asn Glu Lys Lys Ala Ser Ala Gln
                100                 105                 110
Lys Asp Ile Leu Ile Arg Ile Leu Asp Asp Gly Val Lys Lys Leu Asn
                115                 120                 125
Glu Ala Gln Lys Ser Leu Leu Thr Ser Ser Gln Ser Phe Asn Asn Ala
130                 135                 140
Ser Gly Lys Leu Leu Ala Leu Asp Ser Gln Leu Thr Asn Asp Phe Ser
145                 150                 155                 160
Glu Lys Ser Ser Tyr Phe Gln Ser Gln Val Asp Arg Ile Arg Lys Glu
                165                 170                 175
Ala Tyr Ala Gly Ala Ala Ala Gly Ile Val Ala Gly Pro Phe Gly Leu
                180                 185                 190
Ile Ile Ser Tyr Ser Ile Ala Ala Gly Val Ile Glu Gly Lys Leu Ile
                195                 200                 205
Pro Glu Leu Asn Asn Arg Leu Lys Thr Val Gln Asn Phe Phe Thr Ser
210                 215                 220
Leu Ser Ala Thr Val Lys Gln Ala Asn Lys Asp Ile Asp Ala Ala Lys
225                 230                 235                 240
Leu Lys Leu Ala Thr Glu Ile Ala Ile Gly Glu Ile Lys Thr Glu
                245                 250                 255
Thr Glu Thr Thr Arg Phe Tyr Val Asp Tyr Asp Asp Leu Met Leu Ser
                260                 265                 270
Leu Leu Lys Gly Ala Ala Lys Lys Met Ile Asn Thr Cys Asn Glu Tyr
                275                 280                 285
Gln Gln Arg His Gly Lys Lys Thr Leu Phe Glu Val Pro Asp Val Ala
            290                 295                 300
Ser
305

<210> SEQ ID NO 39
<211> LENGTH: 921
<212> TYPE: DNA
<213> ORGANISM: Salmonella typhi

<400> SEQUENCE: 39
atgactagta ttttgcaga acaaactgta gaggtagtta aaagcgcgat cgaaaccgca    60 gatgggcat tagatcttta taacaaatac ctcgaccagg tcatcccctg gaagaccttt   120
gatgaaacca taaagagtt aagccgtttt aacaggagt actcgcagga agcttctgtt   180
ttagttggtg atattaaagt tttgcttatg acagccagg acaagtattt tgaagcgaca   240
caaactgttt atgaatggtg tggtgtcgtg acgcaattac tctcagcgta tattttacta   300
tttgatgaat ataatgagaa aaaagcatca gcccagaaag acattctcat taggatatta   360
gatgatggtg tcaagaaact gaatgaagcg caaaaatctc tcctgacaag ttcacaaagt   420
ttcaacaacg cttccggaaa actgctggca ttagatagcc agttaactaa tgattttcg   480 gaaaaaagta gttatttcca gtcacaggtg gatagaattc gtaaggaagc ttatgccggt   540
gctgcagccg gcatagtcgc cggtccgttt ggattaatta tttcctattc tattgctgcg   600
```

-continued ggcgtgattg aagggaaatt gattccagaa ttgaataaca ggctaaaaac agtgcaaaat 660
ttctttacta gcttatcagc tacagtgaaa caagcgaata aagatatcga tgcggcaaaa 720
ttgaaattag ccactgaaat agcagcaatt ggggagataa aaacggaaac cgaaacaacc 780
agattctacg ttgattatga tgatttaatg ctttctttat taaaaggagc tgcaaagaaa 840
atgattaaca cctgtaatga ataccaacaa cgtcatggta agaagacgct tttcgaggtt 900
cctgacgtcg ctagctgata a 921

<210> SEQ ID NO 40
<211> LENGTH: 909
<212> TYPE: DNA
<213> ORGANISM: Artificial Sequence
<220> FEATURE:
<223> OTHER INFORMATION: chemically-synthesized codon-optimized S. Typhi clyA polynucleotide sequence

<400> SEQUENCE: 40
atgactagta tttttgcgga acagaccgtg gaagtggtta aaagcgcgat cgaaaccgcg 60
gatggcgcgt tagatcttta taacaaatat ctggatcagg tgattccgtg gaaaaccttt 120
gatgaaacca ttaaagaact gagccgtttt aaacaggaat atagccagga agcgagcgtg 180
ctggtgggcg atattaaagt gctgctgatg gatagccagg ataaatattt tgaagcgacc 240
cagaccgtgt atgaatggtg cggcgtggtt acccagctgc tgagcgcgta tatcctgctg 300
tttgatgaat ataacgaaaa gaaagcgagc gctcagaaag atattctgat tcgtattctg 360
gatgacggcg tgaaaaaact gaacgaagcg cagaaaagcc tgctgaccag cagccagagc 420
tttaacaatg cgtccggaaa actgctggcg ctggatagcc agctgaccaa cgattttagc 480
gaaaaaagca gctattttca gagccaggtg gatagaattc gtaaagaagc ctatgccggc 540
gctgcagccg gcattgtggc tggtccgttt ggcctgatta tcagctatag cattgccgcg 600
ggcgttattg aaggcaaact gattccggaa ctgaataacc gtctgaaaac cgttcagaat 660
ttctttacaa gcttaagcgc gaccgtgaaa caggcgaaca aagatatcga tgcggcaaaa 720
ctgaaactgg cgaccgaaat tgcggctatt ggcgaaatta aaaccgaaac cgaaaccacc 780
cgtttttatg tggattatga tgacctgatg ctgagcctgc tgaaaggcgc ggcaaagaaa 840
atgattaaca cctgcaacga atatcagcag cgtcatggca agaaaaccct gtttgaagtg 900
ccggatgtg 909

<210> SEQ ID NO 41
<211> LENGTH: 1102
<212> TYPE: DNA
<213> ORGANISM: Salmonella typhi

<400> SEQUENCE: 41
ggaggtaata ggtaagaata ctttataaaa caggtactta attgcaattt atatatttaa 60
agaggcaaat gattatgacc ggaatatttg cagaacaaac tgtagaggta gttaaaagcg 120
cgatcgaaac cgcagatggg gcattagatc tttataacaa atacctcgac caggtcatcc 180
cctggaagac ctttgatgaa accataaaag agttaagccg ttttaaacag gagtactcgc 240
aggaagcttc tgttttagtt ggtgatatta aagttttgct tatggacagc caggacaagt 300
attttgaagc gacacaaact gtttatgaat ggtgtggtgt cgtgacgcaa ttactctcag 360
cgtatatttt actatttgat gaatataatg agaaaaaagc atcagcccag aaagacattc 420
tcattaggat attagatgat ggtgtcaaga aactgaatga agcgcaaaaa tctctcctga 480

```
caagttcaca aagtttcaac aacgcttccg gaaaactgct ggcattagat agccagttaa      540
ctaatgattt ttcggaaaaa agtagttatt tccagtcaca ggtggataga attcgtaagg      600
aagcttatgc cggtgctgca gccggcatag tcgccggtcc gtttggatta attatttcct      660
attctattgc tgcgggcgtg attgaaggga aattgattcc agaattgaat acaggctaa      720 aaacagtgca aaatttcttt actagcttat cagctacagt gaaacaagcg aataaagata      780
tcgatgcggc aaaattgaaa ttagccactg aaatagcagc aattggggag ataaaaacgg      840
aaaccgaaac aaccagattc tacgttgatt atgatgattt aatgctttct ttattaaaag      900
gagctgcaaa gaaaatgatt aacacctgta atgaatacca acaaagacac ggtaagaaga      960
cgcttttcga ggttcctgac gtctgataca ttttcattcg atctgtgtac ttttaacgcc     1020
cgatagcgta aagaaaatga gagacggaga aaaagcgata ttcaacagcc cgataaacaa     1080
gagtcgttac cgggctgacg ag                                              1102

<210> SEQ ID NO 42
<211> LENGTH: 1102
<212> TYPE: DNA
<213> ORGANISM: Salmonella paratyphi

<400> SEQUENCE: 42
ggaggcaata ggtaggaata agttataaaa caatagctta attgcaattt atatatttaa       60
agaggcaaat gattatgact ggaatatttg cagaacaaac tgtagaggta gttaaaagcg      120
cgatcgaaac cgcagatggg gcattagatt tttataacaa ataccttgac caggttatcc      180
cctggaagac ctttgatgaa accataaaag agttaagccg ttttaaacag gagtactcgc      240
aggaagcttc tgttttagtt ggtgatatta agttttgct tatggacagc caggataagt      300 atttgaagc gacacaaact gtttatgaat ggtgtggtgt cgtgacgcaa ttactctcag      360
cgtatatttt actatttgat gaatataatg agaaaaaagc atcagcgcag aaagacattc      420
tcatcaggat attagatgat ggcgtcaata aactgaatga agcgcaaaaa tctctcctgg      480
gaagttcaca aagtttcaac aacgcttcag gaaaactgct ggcattagat agccagttaa      540
ctaatgattt ctcggaaaaa agtagttatt tccagtcaca ggtggataga attcgtaagg      600
aagcttatgc cggtgctgca gcaggcatag tcgccggtcc gtttggatta attatttcct      660
attctattgc tgcgggcgtg attgaaggga aattgattcc agaattgaat gacaggctaa      720
aagcagtgca aaatttcttt actagcttat cagtcacagt gaaacaagcg aataaagata      780
tcgatgcggc aaaattgaaa ttagccactg aaatagcagc aattggggag ataaaaacgg      840
aaaccgaaac aaccagattc tacgttgatt atgatgattt aatgctttct ttactaaaag      900
gagctgcaaa gaaaatgatt aacacctgta atgaatacca acaaaggcac ggtaagaaga      960
cgcttctcga ggttcctgac atctgataca ttttcattcg ctctgtttac ttttaacgcc     1020
cgatagcgtg aagaaaatga gagacggaga aaaagcgata ttcaacagcc cgataaacaa     1080
gagtcgttac cgggctggcg ag                                              1102

<210> SEQ ID NO 43
<211> LENGTH: 904
<212> TYPE: DNA
<213> ORGANISM: Shigella flexneri

<400> SEQUENCE: 43
atgactgaaa tcgttgcaga taaaacggta gaagtagtta aaaacgcaat cgaaaccgca       60
gatggagcat tagatcttta taataaatat ctcgatcagg tcatcccctg gcagaccttt      120
```

```
gatgaaacca taaaagagtt aagtcgcttt aaacaggagt attcacaggc agcctccgtt    180
ttagtcggcg atattaaaac cttacttatg gatagccagg ataagtattt tgaagcaacc    240
caaacagtgt atgaatggtg tggtgttgcg acgcaattgc tcgcagcgta tattttgcta    300
tttgatgagt acaatgagaa gaaagcatcc gcccctcatt aaggtactgg atgacggcat    360
cacgaagctg aatgaagcgc aaaattccct gctggtaagc tcacaaagtt caacaacgc     420 ttccgggaaa ctgctggcgt tagatagcca gttaaccaat gattttcag aaaaaagcag     480 ctatttccag tcacaggtag ataaaatcag gaaggaagcg tatgccggtg ccgcagccgg    540
tgtcgtcgcc ggtccatttg gtttaatcat ttcctattct attgctgcgg gcgtagttga    600
agggaaactg attccagaat tgaagaacaa gttaaaatct gtgcagagtt tctttaccac    660
cctgtctaac acggttaaac aagcgaataa agatatcgat gccgccaaat tgaaattaac    720
caccgaaata gccgccatcg gggagataaa acggaaact gaaaccacca gattctatgt     780
tgattatgat gatttaatgc tttctttgct aaaagcagcg gccaaaaaaa tgattaacac    840
ctgtaatgag tatcagaaaa gacacggtaa aaagacactc tttgaggtac ctgaagtctg    900
ataa                                                                904

<210> SEQ ID NO 44
<211> LENGTH: 1080
<212> TYPE: DNA
<213> ORGANISM: Escherichia coli

<400> SEQUENCE: 44
agaaataaag acattgacgc atcccgcccg gctaactatg aattagatga agtaaaattt     60
attaatagtt gtaaaacagg agtttcatta caatttatat atttaaagag gcgaatgatt    120
atgactgaaa tcgttgcaga taaaacggta gaagtagtta aaaacgcaat cgaaaccgca    180
gatggagcat tagatcttta taataaatat ctcgatcagg tcatcccctg gcagaccttt    240
gatgaaacca taaaagagtt aagtcgcttt aaacaggagt attcacaggc agcctccgtt    300
ttagtcggcg atattaaaac cttacttatg gatagccagg ataagtattt tgaagcaacc    360
caaacagtgt atgaatggtg tggtgttgcg acgcaattgc tcgcagcgta tattttgcta    420
tttgatgagt acaatgagaa gaaagcatcc gcccagaaag acattctcat taaggtactg    480
gatgacggca tcacgaagct gaatgaagcg caaaaatccc tgctggtaag ctcacaaagt    540 tcaacaacg cttccgggaa actgctggcg ttagatagcc agttaaccaa tgattttca     600 gaaaaagca gctatttcca gtcacaggta gataaaatca ggaaggaagc atatgccggt    660
gccgcagccg gtgtcgtcgc cggtccattt ggattaatca tttcctattc tattgctgcg    720
ggcgtagttg aaggaaaact gattccagaa ttgaagaaca agttaaaatc tgtgcagaat    780
ttctttacca ccctgtctaa cacggttaaa caagcgaata agatatcga tgccgccaaa    840 ttgaaattaa ccaccgaaat agccgccatc ggtgagataa aacgaaaac tgaaacaacc    900 agattctacg ttgattatga tgatttaatg ctttctttgc taaagaagc ggccaaaaaa    960 atgattaaca cctgtaatga gtatcagaaa agacacggta aaagacact ctttgaggta    1020 cctgaagtct gataagcgat tattctctcc atgtactcaa ggtataaggt ttatcacatt   1080

<210> SEQ ID NO 45
<211> LENGTH: 7200
<212> TYPE: DNA
<213> ORGANISM: Artificial Sequence
<220> FEATURE:
<223> OTHER INFORMATION: pSEC10S2 expression plasmid
```

<400> SEQUENCE: 45

```
gaattctgtg gtagcacaga ataatgaaaa gtgtgtaaag aagggtaaaa aaaaccgaat      60
gcgaggcatc cggttgaaat agggggtaaac agacattcag aaatgaatga cggtaataaa     120
taaagttaat gatgatagcg ggagttattc tagttgcgag tgaaggtttt gttttgacat     180
tcagtgctgt caaatactta agaataagtt attgatttta accttgaatt attattgctt     240
gatgttaggt gcttatttcg ccattccgca ataatcttaa aaagttccct tgcatttaca     300
ttttgaaaca tctatagcga taaatgaaac atcttaaaag ttttagtatc atattcgtgt     360
tggattattc tgcattttg gggagaatgg acttgccgac tgattaatga gggttaatca      420
gtatgcagtg gcataaaaaa gcaaataaag gcatataaca gatcgatctt aaacatccac     480
aggaggatgg gatccaaaat aaggaggaaa aaaaaatgac tagtattttt gcagaacaaa     540
ctgtagaggt agttaaaagc gcgatcgaaa ccgcagatgg ggcattagac ctttataaca     600
aatacctcga ccaggtcatc ccctggaaga ccttttgatga aaccataaaa gagttaagcc     660
gttttaaaca ggagtactcg caggaggctt ctgttttagt tggtgatatt aaagttttgc     720
ttatggacag ccaggacaag tattttgaag cgacacaaac tgtttatgaa tggtgtggtg     780
tcgtgacgca attactctca gcgtatattt tactatttga tgaatataat gagaaaaaag     840
catcagccca gaaagacatt ctcattagga tattagatga tggtgtcaag aaactgaatg     900
aagcgcaaaa atctctcctg acaagttcac aaagtttcaa caacgcttcc ggaaaactgc     960
tggcattaga tagccagctg actaatgatt tttcggaaaa aagtagttat tccagtcac    1020
aggtggatag aatccgtaag gaggcttatg ccggtgctgc agccggcata gtcgccggtc    1080
cgtttggatt aattatttcc tattctattg ctgcgggcgt gattgaaggg aaattgattc    1140
cagaattgaa taacaggcta aaaacagtgc aaaatttctt tactagctta tcagctacag    1200
tgaaacaagc gaataaagat atcgatgcgg caaaattgaa attagccact gaaatagcag    1260
cgattgggga gataaaaacg gaaaccgaaa caaccagatt ctacgttgat tatgatgatt    1320
taatgctttc tttattaaaa ggagctgcaa agaaaatgat taacacctgt aatgaatacc    1380
aacaacgtca tggtaagaag acgcttttcg aggttcctga cgtcgctagc tgataaccta    1440
gcccgcctaa tgagcgggct tttttttctc ggcctaggtt tcacctgttc tattaggtgt    1500
tacatgctgt tcatctgtta cattgtcgat ctgttcatgg tgaacagctt aaatgcacc    1560
aaaaactcgt aaaagctctg atgtatctat ctttttttaca ccgttttcat ctgtgcatat    1620
ggacagtttt cccttttgata tctaacggtg aacagttgtt ctactttttgt ttgttagtct    1680
tgatgcttca ctgatagata caagagccat aagaacctca gatccttccg tatttagcca    1740
gtatgttctc tagtgtggtt cgttgttttt gcgtgagcca tgagaacgaa ccattgagat    1800
catgcttact ttgcatgtca ctcaaaaatt ttgcctcaaa actggtgagc tgaatttttg    1860
cagttaaagc atcgtgtagt gttttttctta gtccgttacg taggtaggaa tctgatgtaa    1920
tggttgttgg tattttgtca ccattcattt ttatctggtt gttctcaagt tcggttacga    1980
gatccatttg tctatctagt tcaacttgga aaatcaacgt atcagtcggg cggcctcgct    2040
tatcaaccac caatttcata ttgctgtaag tgtttaaatc tttacttatt ggtttcaaaa    2100
cccattggtt aagccttta aactcatggt agttattttc aagcattaac atgaacttaa     2160
attcatcaag gctaatctct atatttgcct tgtgagtttt cttttgtgtt agttcttta     2220
ataaccactc ataaatcctc atagagtatt tgttttcaaa agacttaaca tgttccagat    2280
tatatttta gaattttttt aactggaaaa gataaggcaa tatctcttca ctaaaaacta    2340
```

```
attctaattt ttcgcttgag aacttggcat agtttgtcca ctggaaaatc tcaaagcctt    2400
taaccaaagg attcctgatt tccacagttc tcgtcatcag ctctctggtt gctttagcta    2460
atacaccata agcattttcc ctactgatgt tcatcatctg agcgtattgg ttataagtga    2520
acgataccgt ccgttctttc cttgtagggt tttcaatcgt ggggttgagt agtgccacac    2580
agcataaaat tagcttggtt tcatgctccg ttaagtcata gcgactaatc gctagttcat    2640
ttgctttgaa acaactaat tcagacatac atctcaattg gtctaggtga ttttaatcac    2700
tataccaatt gagatgggct agtcaatgat aattactagt cctttccctt tgagttgtgg    2760
gtatctgtaa attctgctag acctttgctg gaaaacttgt aaattctgct agaccctctg    2820
taaattccgc tagacctttg tgtgtttttt ttgtttatat tcaagtggtt ataatttata    2880
gaataaagaa agaataaaaa aagataaaaa gaatagatcc cagccctgtg tataactcac    2940
tactttagtc agttccgcag tattacaaaa ggatgtcgca aacgctgttt gctcctctac    3000
aaaacagacc ttaaacccct aaaggcttaa gtagcaccct cgcaagctcg gcaaatcgc    3060 tgaatattcc ttttgtctcc gaccatcagg cacctgagtc gctgtctttt tcgtgacatt    3120
cagttcgctg cgctcacggc tctggcagtg aatgggggta aatggcacta caggcgcctt    3180
ttatggattc atgcaaggaa actacccata atacaagaaa agcccgtcac gggcttctca    3240
gggcgtttta tggcgggtct gctatgtggt gctatctgac ttttgctgt tcagcagttc     3300 ctgccctctg attttccagt ctgaccactt cggattatcc cgtgacaggt cattcagact    3360
ggctaatgca cccagtaagg cagcggtatc atcaacaggc ttaccgtct tactgtcaac     3420 cggatctaaa acactaggcc caagagtttg tagaaacgca aaaaggccat ccgtcaggat    3480
ggccttctgc ttaatttgat gcctggcagt ttatggcggg cgtcctgccc gccaccctcc    3540
gggccgttgc ttcgcaacgt tcaaatccgc tcccggcgga tttgtcctac tcaggagagc    3600
gttcaccgac aaacaacaga taaaacgaaa ggcccagtct ttcgactgag cctttcgttt    3660
tatttgatgc ctggcagttc cctactctcg catggggaga ccccacacta ccatcggcgc    3720
tacggcgttt cacttctgag ttcggcatgg ggtcaggtgg gaccaccgcg ctactgccgc    3780
caggcaaatt ctgttttatc agaccgcttc tgcgttctga tttaatctgt atcaggctga    3840
aaatcttctc tcatccgcca aaacagccaa gctggatcta aaacactagc ccaacctttc    3900
atagaaggcg gcggtggaat cgaaatctcg tgatggcagg ttgggcgtcg cttggtcggt    3960
catttcgaac cccagagtcc cgctcagaag aactcgtcaa gaaggcgata gaaggcgatg    4020
cgctgcgaat cgggagcggc gataccgtaa agcacgagga gcggtcagc ccattcgccg     4080 ccaagctctt cagcaatatc acgggtagcc aacgctatgt cctgatagcg gtccgccaca    4140
cccagccggc cacagtcgat gaatccagaa agcggccat tttccaccat gatattcggc     4200
aagcaggcat cgccatgggt cacgacgaga tcctcgccgt cgggcatgcg cgccttgagc    4260
ctggcgaaca gttcggctgg cgcgagcccc tgatgctctt cgtccagatc atcctgatcg    4320
acaagaccgg cttccatccg agtacgtgct cgctcgatgc gatgtttcgc ttggtggtcg    4380
aatgggcagg tagccggatc aagcgtatgc agccgccgca ttgcatcagc catgatggat    4440
actttctcgg caggagcaag gtgagatgac aggagatcct gccccggcac ttcgcccaat    4500
agcagccagt cccttcccgc ttcagtgaca acgtcgagca cagctgcgca aggaacgccc    4560
gtcgtggcca gccacgatag ccgcgctgcc tcgtcctgca gttcattcag ggcaccggac    4620
aggtcggtct tgacaaaaag aaccgggcgc ccctgcgctg acagccggaa cacggcggca    4680
tcagagcagc cgattgtctg ttgtgcccag tcatagccga atagcctctc cacccaagcg    4740
```

```
gccggagaac ctgcgtgcaa tccatcttgt tcaatcatgc gaaacgatcc tcatcctgtc    4800
tcttgatcag atcttgatcc cctgcgccat cagatccttg gcggcaagaa agccatccag    4860
tttactttgc agggcttccc aaccttacca gagggcgccc cagccgtggc aattccggtt    4920
cgctgctaga caacatcagc aaggagaaag gggctaccgg cgaaccagca gcccctttat    4980
aaaggcgctt cagtagtcag accagcatca gtcctgaaaa ggcgggcctg cgcccgcctc    5040
caggttgcta cttaccggat tcgtaagcca tgaaagccgc cacctccctg tgtccgtctc    5100
tgtaacgaat ctcgcacagc gattttcgtg tcagataagt gaatatcaac agtgtgagac    5160
acacgatcaa cacacaccag acaagggaac ttcgtggtag tttcatggcc ttcttctcct    5220
tgcgcaaagc gcggtaagag gctatcctga tgtggactag acatagggat gcctcgtggt    5280
ggttaatgaa aattaactta ctacggggct atcttctttc tgccacacaa cacggcaaca    5340
aaccaccttc acgtcatgag gcagaaagcc tcaagcgccg ggcacatcat agcccatata    5400
cctgcacgct gaccacactc actttccctg aaaataatcc gctcattcag accgttcacg    5460
ggaaatccgt gtgattgttg ccgcatcacg ctgcctcccg gagtttgtct cgagcacttt    5520
tgttacccgc caaacaaaac ccaaaaacaa cccatcccca acccaataaa acaccaaaac    5580
aagacaaata atcattgatt gatggttgaa atggggtaaa cttgacaaac aaacccactt    5640 aaacccaaa acatacccaa acacacacca aaaaacacc ataaggagtt ttataaatgt    5700
tggtattcat tgatgacggt tcaacaaaca tcaaactaca gtggcaggaa agcgacggaa    5760
caattaaaca gcacattagc ccgaacagct tcaaacgcga gtgggcagtc tcttttggtg    5820
ataaaaaggt cttttaactac acactgaacg gcgaacagta ttcatttgat ccaatcagcc    5880
cggatgctgt agtcacaacc aatatcgcat ggcaatacag cgacgttaat gtcgttgcag    5940
tgcatcacgc cttactgacc agtggtctgc cggtaagcga agtggatatt gtttgcacac    6000
ttcctctgac agagtattac gacagaaata accaacccaa tacggaaaat attgagcgta    6060
agaaagcaaa cttccggaaa aaaattacat taaatggcgg ggatacattc acaataaaag    6120
atgtaaaagt catgcctgaa tctataccgg caggttatga agttctacaa gaactggatg    6180
agttagattc tttattaatt atagatctcg ggggcaccac attagatatt tctcaggtaa    6240
tggggaaatt atcggggatc agtaaaatat acggagactc atctcttggt gtctctctgg    6300
ttacatctgc agtaaaagat gccctttctc ttgcgagaac aaaaggaagt agctatcttg    6360
ctgacgatat aatcattcac agaaaagata ataactatct gaagcaacga attaatgatg    6420
agaacaaaat atcaatagtc accgaagcaa tgaatgaagc acttcgtaaa cttgagcaac    6480
gtgtattaaa tacgctcaat gaattttctg gttatactca tgttatggtt ataggcggtg    6540
gcgcagaatt aatatgcgat gcagtaaaaa aacacacaca gattcgtgat gaacgttttt    6600
tcaaaaccaa taactctcaa tatgatttag ttaacggtat gtatctcata ggtaattaat    6660
gatggacaag cgcagaacca ttgccttcaa actaaatcca gatgtaaatc aaacagataa    6720
aattgtttgt gatacactgg acagtatccc gcaaggggaa cgaagccgcc ttaaccgggc    6780
cgcactgacg gcaggtctgg ccttatacag acaagatccc cggaccccctt tccttttatg    6840 tgagctgctg acgaaagaaa ccacatttc agatatcgtg aatatattga gatcgctatt    6900
tccaaaagag atggccgatt ttaattcttc aatagtcact caatcctctt cacaacaaga    6960
gcaaaaaagt gatgaagaga ccaaaaaaaa tgcgatgaag ctaataaatt aattcaatta    7020
ttattgagtt ccccttttcc actatcaggc tggataaagg gaactcaatc aagttatttt    7080
```

```
cttaccagtc attacataat cgttattatg aaataatcgt ttgcactgtc tctgttattc    7140
aggcaatttc aataaaggca cttgctcacg ctctgtcatt ttctgaaact cttcatgctg    7200
```

<210> SEQ ID NO 46
<211> LENGTH: 878
<212> TYPE: PRT
<213> ORGANISM: Clostridium difficile

<400> SEQUENCE: 46

```
Met Ala Ser Lys Ile Gln Met Arg Asn Lys Lys Val Leu Ser Phe Leu
1               5                   10                  15

Thr Leu Thr Ala Ile Val Ser Gln Ala Leu Val Tyr Pro Val Tyr Ala
            20                  25                  30

Gln Thr Ser Thr Ser Asn His Ser Asn Lys Lys Lys Glu Ile Val Asn
        35                  40                  45

Glu Asp Ile Leu Pro Asn Asn Gly Leu Met Gly Tyr Tyr Phe Thr Asp
    50                  55                  60

Glu His Phe Lys Asp Leu Lys Leu Met Ala Pro Ile Lys Asp Gly Asn
65                  70                  75                  80

Leu Lys Phe Glu Glu Lys Lys Val Asp Lys Leu Leu Asp Lys Asp Lys
                85                  90                  95

Ser Asp Val Lys Ser Ile Arg Trp Thr Gly Arg Ile Ile Pro Ser Lys
            100                 105                 110

Asp Gly Glu Tyr Thr Leu Ser Thr Asp Arg Asp Val Leu Met Gln
        115                 120                 125

Val Asn Thr Glu Ser Thr Ile Ser Asn Thr Leu Lys Val Asn Met Lys
    130                 135                 140

Lys Gly Lys Glu Tyr Lys Val Arg Ile Glu Leu Gln Asp Lys Asn Leu
145                 150                 155                 160

Gly Ser Ile Asp Asn Leu Ser Ser Pro Asn Leu Tyr Trp Glu Leu Asp
                165                 170                 175

Gly Met Lys Lys Ile Ile Pro Glu Glu Asn Leu Phe Leu Arg Asp Tyr
            180                 185                 190

Ser Asn Ile Glu Lys Asp Asp Pro Phe Ile Pro Asn Asn Phe Phe
        195                 200                 205

Asp Pro Lys Leu Met Ser Asp Trp Glu Asp Glu Asp Leu Asp Thr Asp
    210                 215                 220

Asn Asp Asn Ile Pro Asp Ser Tyr Glu Arg Asn Gly Tyr Thr Ile Lys
225                 230                 235                 240

Asp Leu Ile Ala Val Lys Trp Glu Asp Ser Phe Ala Glu Gln Gly Tyr
                245                 250                 255

Lys Lys Tyr Val Ser Asn Tyr Leu Glu Ser Asn Thr Ala Gly Asp Pro
            260                 265                 270

Tyr Thr Asp Tyr Glu Lys Ala Ser Gly Ser Phe Asp Lys Ala Ile Lys
        275                 280                 285

Thr Glu Ala Arg Asp Pro Leu Val Ala Ala Tyr Pro Ile Val Gly Val
    290                 295                 300

Gly Met Glu Lys Leu Ile Ile Ser Thr Asn Glu His Ala Ser Thr Asp
305                 310                 315                 320

Gln Gly Lys Thr Val Ser Arg Ala Thr Thr Asn Ser Lys Thr Glu Ser
                325                 330                 335

Asn Thr Ala Gly Val Ser Val Asn Val Gly Tyr Gln Asn Gly Phe Thr
            340                 345                 350
```

-continued

```
Ala Asn Val Thr Thr Asn Tyr Ser His Thr Thr Asp Asn Ser Thr Ala
            355                 360                 365

Val Gln Asp Ser Asn Gly Glu Ser Trp Asn Thr Gly Leu Ser Ile Asn
    370                 375                 380

Lys Gly Glu Ser Ala Tyr Ile Asn Ala Asn Val Arg Tyr Tyr Asn Thr
385                 390                 395                 400

Gly Thr Ala Pro Met Tyr Lys Val Thr Pro Thr Thr Asn Leu Val Leu
                405                 410                 415

Asp Gly Asp Thr Leu Ser Thr Ile Lys Ala Gln Glu Asn Gln Ile Gly
            420                 425                 430

Asn Asn Leu Ser Pro Gly Asp Thr Tyr Pro Lys Lys Gly Leu Ser Pro
        435                 440                 445

Leu Ala Leu Asn Thr Met Asp Gln Phe Ser Ser Arg Leu Ile Pro Ile
    450                 455                 460

Asn Tyr Asp Gln Leu Lys Lys Leu Asp Ala Gly Lys Gln Ile Lys Leu
465                 470                 475                 480

Glu Thr Thr Gln Val Ser Gly Asn Phe Gly Thr Lys Asn Ser Ser Gly
                485                 490                 495

Gln Ile Val Thr Glu Gly Asn Ser Trp Ser Asp Tyr Ile Ser Gln Ile
            500                 505                 510

Asp Ser Ile Ser Ala Ser Ile Ile Leu Asp Thr Glu Asn Glu Ser Tyr
        515                 520                 525

Glu Arg Arg Val Thr Ala Lys Asn Leu Gln Asp Pro Glu Asp Lys Thr
    530                 535                 540

Pro Glu Leu Thr Ile Gly Glu Ala Ile Glu Lys Ala Phe Gly Ala Thr
545                 550                 555                 560

Lys Lys Asp Gly Leu Leu Tyr Phe Asn Asp Ile Pro Ile Asp Glu Ser
                565                 570                 575

Cys Val Glu Leu Ile Phe Asp Asp Asn Thr Ala Asn Lys Ile Lys Asp
            580                 585                 590

Ser Leu Lys Thr Leu Ser Asp Lys Lys Ile Tyr Asn Val Lys Leu Glu
        595                 600                 605

Arg Gly Met Asn Ile Leu Ile Lys Thr Pro Thr Tyr Phe Thr Asn Phe
    610                 615                 620

Asp Asp Tyr Asn Asn Tyr Pro Ser Thr Trp Ser Asn Val Asn Thr Thr
625                 630                 635                 640

Asn Gln Asp Gly Leu Gln Gly Ser Ala Asn Lys Leu Asn Gly Glu Thr
                645                 650                 655

Lys Ile Lys Ile Pro Met Ser Glu Leu Lys Pro Tyr Lys Arg Tyr Val
            660                 665                 670

Phe Ser Gly Tyr Ser Lys Asp Pro Leu Thr Ser Asn Ser Ile Ile Val
        675                 680                 685

Lys Ile Lys Ala Lys Glu Glu Lys Thr Asp Tyr Leu Val Pro Glu Gln
    690                 695                 700

Gly Tyr Thr Lys Phe Ser Tyr Glu Phe Glu Thr Thr Glu Lys Asp Ser
705                 710                 715                 720

Ser Asn Ile Glu Ile Thr Leu Ile Gly Ser Gly Thr Thr Tyr Leu Asp
                725                 730                 735

Asn Leu Ser Ile Thr Glu Leu Asn Ser Thr Pro Glu Ile Leu Asp Glu
            740                 745                 750

Pro Glu Val Lys Ile Pro Thr Asp Gln Glu Ile Met Asp Ala His Lys
        755                 760                 765
```

-continued

```
Ile Tyr Phe Ala Asp Leu Asn Phe Asn Pro Ser Thr Gly Asn Thr Tyr
    770                 775                 780

Ile Asn Gly Met Tyr Phe Ala Pro Thr Gln Thr Asn Lys Glu Ala Leu
785                 790                 795                 800

Asp Tyr Ile Gln Lys Tyr Arg Val Glu Ala Thr Leu Gln Tyr Ser Gly
                805                 810                 815

Phe Lys Asp Ile Gly Thr Lys Asp Lys Glu Met Arg Asn Tyr Leu Gly
            820                 825                 830

Asp Pro Asn Gln Pro Lys Thr Asn Tyr Val Asn Leu Arg Ser Tyr Phe
        835                 840                 845

Thr Gly Gly Glu Asn Ile Met Thr Tyr Lys Lys Leu Arg Ile Tyr Ala
    850                 855                 860

Ile Thr Pro Asp Asp Arg Glu Leu Leu Val Leu Ser Val Asp
865                 870                 875
```

<210> SEQ ID NO 47
<211> LENGTH: 2054
<212> TYPE: DNA
<213> ORGANISM: Artificial Sequence
<220> FEATURE:
<223> OTHER INFORMATION: Synthetic CBD-BT gene

<400> SEQUENCE: 47

```
agatctaaaa taaggaggaa aaaaaaatgg ctagcctgat gtctgattgg gaagatgaag     60
acctggatac cgataatgat aacattccgg atagttatga acgcaatggt tacaccatca    120
aagacctgat tgcggttaaa tgggaagata gctttgccga acagggctac aaaaaatacg    180
tgagcaacta cctggaatct aacaccgccg gtgatccgta tacggattac gaaaaagcaa    240
gcggctcttt cgataaagca attaaaaccg aagcgcgtga tccgctggtt gcggcctatc    300
cgatcgtggg cgttggtatg gaaaaactga ttatctctac caacgaacat gcgagtaccg    360
atcagggtaa aaccgtgagt cgcgccacca cgaatagtaa aaccgaaagc aacacggcag    420
gcgtgagcgt taatgtgggc tatcagaacg gttttaccgc gaatgttacc acgaactaca    480
gccacaccac ggataattct accgccgtgc aggattctaa tggcgaaagt tggaacacgg    540
gtctgagtat taacaaaggc gaaagcgcct acatcaacgc aaacgttcgt tactacaaca    600
ccggtacggc cccgatgtac aaagttaccc cgaccacgaa cctggtgctg gatggcgata    660
ccctgagcac gattaaagca caggaaaacc agatcggtaa taacctgtct ccgggcgata    720
cctatccgaa aaaaggtctg agtccgctgg cgctgaatac catggatcag tttagtagcc    780
gcctgattcc gatcaactac gatcagctga aaaaactgga tgccggcaaa cagattaaac    840
tggaaaccac gcaagttagc ggcaatttcg gtaccaaaaa ctctagtggt cagatcgtga    900
cggaaggcaa tagttggagc gattatatta gccagatcga ttctattagt gcaagcatta    960
tcctggatac cgaaaatgaa tcttacgaac gtcgcgtgac ggcgaaaaac ctgcaagatc   1020
cggaagataa aaccccggaa ctgacgatcg gtgaagccat tgaaaaagca tttggtgcga   1080
ccaaaaaaga tggcctgctg tatttcaacg atattccgat cgatgaaagc tgcgttgaac   1140
tgatcttcga tgataacacc gcaaacaaaa tcaaagatag tctgaaaacg ctgagcgata   1200
agaaaattta taacgtgaaa ctggaacgtg gcatgaacat tctgatcaaa accccgacgt   1260
acttcaccaa cttcgatgat tacaacaact acccgagtac gtggagcaat gttaacacca   1320
cgaaccagga tggcctgcag ggtagcgcca acaaactgaa cggtgaaacc aaaatcaaaa   1380
tcccgatgtc tgaactgaaa ccgtataaac gctacgtgtt ttctggctat agtaaagatc   1440
```

| | |
|---|---|
| cgctgacctc taatagtatc atcgttaaaa tcaaagcgaa agaagaaaaa accgattacc | 1500 |
| tggtgccgga acagggttac acgaaattca gttacgaatt tgaaaccacg gaaaaagata | 1560 |
| gctctaacat tgaaatcacc ctgattggca gcggtaccac gtatctggat aatctgtcta | 1620 |
| ttaccgaact gaacagtacg ccggaaatcc tggatgaacc ggaagtgaaa atcccgaccg | 1680 |
| atcaggaaat catggatgcc cataaaatct atttcgcgga tctgaacttc aacccgagca | 1740 |
| ccggtaatac gtatattaac ggcatgtact ttgcaccgac ccagacgaat aaagaagcgc | 1800 |
| tggattatat tcagaaatac cgtgttgaag ccaccctgca gtatagcggc ttcaaagata | 1860 |
| tcggtacgaa agataaagaa atgcgtaatt acctgggcga tccgaaccag ccgaaaacca | 1920 |
| attatgtgaa cctgcgctct tactttaccg gcggtgaaaa catcatgacg tacaaaaaac | 1980 |
| tgcgtatcta cgcgattacc ccggatgatc gcgaactgct ggttctgagt gtggattaat | 2040 |
| aacctaggaa gctt | 2054 |

<210> SEQ ID NO 48
<211> LENGTH: 2655
<212> TYPE: DNA
<213> ORGANISM: Artificial Sequence
<220> FEATURE:
<223> OTHER INFORMATION: Synthetic CDTB-GS gene

<400> SEQUENCE: 48

| | |
|---|---|
| tagtaatgaa tggctagcaa aatccagatg cgtaacaaaa aagttctgag ttttctgacc | 60 |
| ctgacggcga tcgtgagcca ggccctggtt tatccggtgt acgcgcagac ctctacgagt | 120 |
| aaccatagca acaagaaaaa agaaatcgtg aacgaagata tcctgccgaa caatggcctg | 180 |
| atgggttatt actttaccga tgaacacttc aaagacctga actgatggc gccgattaaa | 240 |
| gatggcaacc tgaaattcga agagaaaaaa gttgataaac tgctggataa agataaaagc | 300 |
| gatgtgaaat ctatccgttg gaccggtcgc attatcccga gcaaagatgg cgaatatacc | 360 |
| ctgtctacgg atcgtgatga tgttctgatg caagtgaata ccgaaagcac gatctctaac | 420 |
| accctgaaag ttaacatgaa aaagggtaaa gaatacaaag tgcgcatcga actgcaggat | 480 |
| aaaaacctgg gctctatcga taatctgagc tctccgaacc tgtattggga actggatggt | 540 |
| atgaagaaaa ttatcccgga gaaaatctg tttctgcgtg attacagcaa cattgaaaaa | 600 |
| gatgatccgt tcatcccgaa caataacttt ttcgatccga aactgatgtc tgattgggaa | 660 |
| gatgaagacc tggataccga taatgataac attccggata gttatgaacg caatggttac | 720 |
| accatcaaag acctgattgc ggttaaatgg aagatagct ttgccgaaca gggctacaaa | 780 |
| aaatacgtga gcaactacct ggaatctaac accgccggtg atccgtatac ggattacgaa | 840 |
| aaagcaagcg gctcttttcga taaagcaatt aaaaccgaag cgcgtgatcc gctggttgcg | 900 |
| gcctatccga tcgtgggcgt tggtatggaa aaactgatta tctctaccaa cgaacatgcg | 960 |
| agtaccgatc agggtaaaac cgtgagtcgc gccaccacga atagtaaaac cgaaagcaac | 1020 |
| acggcaggcg tgagcgttaa tgtgggctat cagaacggtt ttaccgcgaa tgttaccacg | 1080 |
| aactacagcc acaccacgga taattctacc gccgtgcagg attctaatgg cgaaagttgg | 1140 |
| aacacgggtc tgagtattaa caaggcgaa agcgcctaca tcaacgcaaa cgttcgttac | 1200 |
| tacaacaccg gtacggcccc gatgtacaaa gttaccccga ccacgaacct ggtgctggat | 1260 |
| ggcgataccc tgagcacgat taaagcacag gaaaaccaga tcggtaataa cctgtctccg | 1320 |
| ggcgataccct atccgaaaaa aggtctgagt ccgctggcgc tgaataccat ggatcagttt | 1380 |
| agtagccgcc tgattccgat caactacgat cagctgaaaa aactggatgc cggcaaacag | 1440 |

```
attaaactgg aaaccacgca agttagcggc aatttcggta ccaaaaactc tagtggtcag   1500
atcgtgacgg aaggcaatag ttggagcgat tatattagcc agatcgattc tattagtgca   1560
agcattatcc tggataccga aaatgaatct tacgaacgtc gcgtgacggc gaaaaacctg   1620
caagatccgg aagataaaac cccggaactg acgatcggtg aagccattga aaaagcattt   1680
ggtgcgacca aaaagatgg cctgctgtat ttcaacgata ttccgatcga tgaaagctgc   1740
gttgaactga tcttcgatga taacaccgca acaaaatca agatagtct gaaaacgctg   1800 agcgataaga aaatttataa cgtgaaactg aacgtggca tgaacattct gatcaaaacc   1860
ccgacgtact tcaccaactt cgatgattac aacaactacc cgagtacgtg agcaatgtt   1920 aacaccacga accaggatgg cctgcagggt agcgccaaca aactgaacgg tgaaaccaaa   1980
atcaaaatcc cgatgtctga actgaaaccg tataaacgct acgtgttttc tggctatagt   2040
aaagatccgc tgacctctaa tagtatcatc gttaaaatca aagcgaaaga agaaaaaacc   2100
gattacctgg tgccggaaca gggttacacg aaattcagtt acgaatttga aaccacggaa   2160
aaagatagct ctaacattga aatcaccctg attggcagcg gtaccacgta tctggataat   2220
ctgtctatta ccgaactgaa cagtacgccg gaaatcctgg atgaaccgga agtgaaaatc   2280
ccgaccgatc aggaaatcat ggatgcccat aaaatctatt cgcggatct gaacttcaac   2340 ccgagcaccg gtaatacgta tattaacggc atgtactttg caccgaccca gacgaataaa   2400
gaagcgctgg attatattca gaataccgt gttgaagcca ccctgcagta tagcggcttc   2460
aaagatatcg gtacgaaaga taaagaaatg cgtaattacc tgggcgatcc gaaccagccg   2520
aaaaccaatt atgtgaacct gcgctcttac tttaccggcg gtgaaaacat catgacgtac   2580
aaaaaactgc gtatctacgc gattacccc gatgatcgcg aactgctggt tctgagtgtg   2640
gattaataac ctagg                                                   2655
```

<210> SEQ ID NO 49
<211> LENGTH: 972
<212> TYPE: PRT
<213> ORGANISM: Artificial Sequence
<220> FEATURE:
<223> OTHER INFORMATION: ClyA-CBD-BT fusion protein

<400> SEQUENCE: 49

```
Met Thr Ser Ile Phe Ala Glu Gln Thr Val Glu Val Val Lys Ser Ala
1               5                   10                  15

Ile Glu Thr Ala Asp Gly Ala Leu Asp Leu Tyr Asn Lys Tyr Leu Asp
            20                  25                  30

Gln Val Ile Pro Trp Lys Thr Phe Asp Glu Thr Ile Lys Glu Leu Ser
        35                  40                  45

Arg Phe Lys Gln Glu Tyr Ser Gln Glu Ala Ser Val Leu Val Gly Asp
    50                  55                  60

Ile Lys Val Leu Leu Met Asp Ser Gln Asp Lys Tyr Phe Glu Ala Thr
65                  70                  75                  80

Gln Thr Val Tyr Glu Trp Cys Gly Val Val Thr Gln Leu Leu Ser Ala
                85                  90                  95

Tyr Ile Leu Leu Phe Asp Glu Tyr Asn Glu Lys Ala Ser Ala Gln
            100                 105                 110

Lys Asp Ile Leu Ile Arg Ile Leu Asp Asp Gly Val Lys Lys Leu Asn
        115                 120                 125

Glu Ala Gln Lys Ser Leu Leu Thr Ser Ser Gln Ser Phe Asn Asn Ala
    130                 135                 140
```

-continued

Ser Gly Lys Leu Leu Ala Leu Asp Ser Gln Leu Thr Asn Asp Phe Ser
145                 150                 155                 160

Glu Lys Ser Ser Tyr Phe Gln Ser Gln Val Asp Arg Ile Arg Lys Glu
            165                 170                 175

Ala Tyr Ala Gly Ala Ala Gly Ile Val Ala Gly Pro Phe Gly Leu
            180                 185                 190

Ile Ile Ser Tyr Ser Ile Ala Ala Gly Val Ile Glu Gly Lys Leu Ile
            195                 200                 205

Pro Glu Leu Asn Asn Arg Leu Lys Thr Val Gln Asn Phe Phe Thr Ser
    210                 215                 220

Leu Ser Ala Thr Val Lys Gln Ala Asn Lys Asp Ile Asp Ala Ala Lys
225                 230                 235                 240

Leu Lys Leu Ala Thr Glu Ile Ala Ala Ile Gly Glu Ile Lys Thr Glu
                245                 250                 255

Thr Glu Thr Thr Arg Phe Tyr Val Asp Tyr Asp Asp Leu Met Leu Ser
                260                 265                 270

Leu Leu Lys Gly Ala Ala Lys Lys Met Ile Asn Thr Cys Asn Glu Tyr
        275                 280                 285

Gln Gln Arg His Gly Lys Lys Thr Leu Phe Glu Val Pro Asp Val Ala
    290                 295                 300

Ser Leu Met Ser Asp Trp Glu Asp Glu Asp Leu Asp Thr Asp Asn Asp
305                 310                 315                 320

Asn Ile Pro Asp Ser Tyr Glu Arg Asn Gly Tyr Thr Ile Lys Asp Leu
                325                 330                 335

Ile Ala Val Lys Trp Glu Asp Ser Phe Ala Glu Gln Gly Tyr Lys Lys
                340                 345                 350

Tyr Val Ser Asn Tyr Leu Glu Ser Asn Thr Ala Gly Asp Pro Tyr Thr
            355                 360                 365

Asp Tyr Glu Lys Ala Ser Gly Ser Phe Asp Lys Ala Ile Lys Thr Glu
    370                 375                 380

Ala Arg Asp Pro Leu Val Ala Ala Tyr Pro Ile Val Gly Val Gly Met
385                 390                 395                 400

Glu Lys Leu Ile Ile Ser Thr Asn Glu His Ala Ser Thr Asp Gln Gly
                405                 410                 415

Lys Thr Val Ser Arg Ala Thr Asn Ser Lys Thr Glu Ser Asn Thr
            420                 425                 430

Ala Gly Val Ser Val Asn Val Gly Tyr Gln Asn Gly Phe Thr Ala Asn
            435                 440                 445

Val Thr Thr Asn Tyr Ser His Thr Thr Asp Asn Ser Thr Ala Val Gln
    450                 455                 460

Asp Ser Asn Gly Glu Ser Trp Asn Thr Gly Leu Ser Ile Asn Lys Gly
465                 470                 475                 480

Glu Ser Ala Tyr Ile Asn Ala Asn Val Arg Tyr Tyr Asn Thr Gly Thr
                485                 490                 495

Ala Pro Met Tyr Lys Val Thr Pro Thr Thr Asn Leu Val Leu Asp Gly
            500                 505                 510

Asp Thr Leu Ser Thr Ile Lys Ala Gln Glu Asn Gln Ile Gly Asn Asn
            515                 520                 525

Leu Ser Pro Gly Asp Thr Tyr Pro Lys Lys Gly Leu Ser Pro Leu Ala
    530                 535                 540

Leu Asn Thr Met Asp Gln Phe Ser Ser Arg Leu Ile Pro Ile Asn Tyr
545                 550                 555                 560

-continued

```
Asp Gln Leu Lys Lys Leu Asp Ala Gly Lys Gln Ile Lys Leu Glu Thr
            565                 570                 575
Thr Gln Val Ser Gly Asn Phe Gly Thr Lys Asn Ser Ser Gly Gln Ile
        580                 585                 590
Val Thr Glu Gly Asn Ser Trp Ser Asp Tyr Ile Ser Gln Ile Asp Ser
    595                 600                 605
Ile Ser Ala Ser Ile Ile Leu Asp Thr Glu Asn Glu Ser Tyr Glu Arg
        610                 615                 620
Arg Val Thr Ala Lys Asn Leu Gln Asp Pro Asp Lys Thr Pro Glu
625                 630                 635                 640
Leu Thr Ile Gly Glu Ala Ile Glu Lys Ala Phe Gly Ala Thr Lys Lys
                645                 650                 655
Asp Gly Leu Leu Tyr Phe Asn Asp Ile Pro Ile Asp Glu Ser Cys Val
            660                 665                 670
Glu Leu Ile Phe Asp Asp Asn Thr Ala Asn Lys Ile Lys Asp Ser Leu
        675                 680                 685
Lys Thr Leu Ser Asp Lys Lys Ile Tyr Asn Val Lys Leu Glu Arg Gly
    690                 695                 700
Met Asn Ile Leu Ile Lys Thr Pro Thr Tyr Phe Thr Asn Phe Asp Asp
705                 710                 715                 720
Tyr Asn Asn Tyr Pro Ser Thr Trp Ser Asn Val Asn Thr Thr Asn Gln
                725                 730                 735
Asp Gly Leu Gln Gly Ser Ala Asn Lys Leu Asn Gly Thr Lys Ile
            740                 745                 750
Lys Ile Pro Met Ser Glu Leu Lys Pro Tyr Lys Arg Tyr Val Phe Ser
    755                 760                 765
Gly Tyr Ser Lys Asp Pro Leu Thr Ser Asn Ser Ile Ile Val Lys Ile
    770                 775                 780
Lys Ala Lys Glu Glu Lys Thr Asp Tyr Leu Val Pro Glu Gln Gly Tyr
785                 790                 795                 800
Thr Lys Phe Ser Tyr Glu Phe Glu Thr Thr Glu Lys Asp Ser Ser Asn
                805                 810                 815
Ile Glu Ile Thr Leu Ile Gly Ser Gly Thr Thr Tyr Leu Asp Asn Leu
            820                 825                 830
Ser Ile Thr Glu Leu Asn Ser Thr Pro Glu Ile Leu Asp Glu Pro Glu
        835                 840                 845
Val Lys Ile Pro Thr Asp Gln Glu Ile Met Asp Ala His Lys Ile Tyr
    850                 855                 860
Phe Ala Asp Leu Asn Phe Asn Pro Ser Thr Gly Asn Thr Tyr Ile Asn
865                 870                 875                 880
Gly Met Tyr Phe Ala Pro Thr Gln Thr Asn Lys Glu Ala Leu Asp Tyr
                885                 890                 895
Ile Gln Lys Tyr Arg Val Glu Ala Thr Leu Gln Tyr Ser Gly Phe Lys
            900                 905                 910
Asp Ile Gly Thr Lys Asp Lys Glu Met Arg Asn Tyr Leu Gly Asp Pro
        915                 920                 925
Asn Gln Pro Lys Thr Asn Tyr Val Asn Leu Arg Ser Tyr Phe Thr Gly
    930                 935                 940
Gly Glu Asn Ile Met Thr Tyr Lys Lys Leu Arg Ile Tyr Ala Ile Thr
945                 950                 955                 960
Pro Asp Asp Arg Glu Leu Leu Val Leu Ser Val Asp
                965                 970
```

```
<210> SEQ ID NO 50
<211> LENGTH: 3491
<212> TYPE: DNA
<213> ORGANISM: Artificial Sequence
<220> FEATURE:
<223> OTHER INFORMATION: PompC-clyA*-b2 expression cassette

<400> SEQUENCE: 50
gaattctgtg gtagcacaga ataatgaaaa gtgtgtaaag aagggtaaaa aaaaccgaat      60
gcgaggcatc cggttgaaat agggggtaaac agacattcag aaatgaatga cggtaataaa    120
taaagttaat gatgatagcg ggagttattc tagttgcgag tgaaggtttt gttttgacat    180
tcagtgctgt caaatactta agaataagtt attgatttta accttgaatt attattgctt    240
gatgttaggt gcttatttcg ccattccgca ataatcttaa aaagttccct tgcatttaca    300
ttttgaaaca tctatagcga taaatgaaac atcttaaaag ttttagtatc atattcgtgt    360
tggattattc tgcattttg gggagaatgg acttgccgac tgattaatga gggttaatca    420
gtatgcagtg gcataaaaaa gcaaataaag gcatataaca gatcgatctt aaacatccac    480
aggaggatgg gatccaaaat aaggaggaaa aaaaaatgac tagtattttt gcagaacaaa    540
ctgtagaggt agttaaaagc gcgatcgaaa ccgcagatgg gcattagac ctttataaca    600
aatacctcga ccaggtcatc ccctggaaga cctttgatga accataaaa gagttaagcc    660
gttttaaaca ggagtactcg caggaggctt ctgttttagt tggtgatatt aaagttttgc    720
ttatggacag ccaggacaag tattttgaag cgacacaaac tgtttatgaa tggtgtggtg    780
tcgtgacgca attactctca gcgtatattt tactatttga tgaatataat gagaaaaaag    840
catcagccca gaaagacatt ctcattagga tattagtga tggtgtcaag aaactgaatg    900
aagcgcaaaa atctctcctg acaagttcac aaagtttcaa caacgcttcc ggaaaactgc    960
tggcattaga tagccagctg actaatgatt tttcggaaaa aagtagttat ttccagtcac   1020
aggtggatag aatccgtaag gaggcttatg ccggtgctgc agccggcata gtcgccggtc   1080
cgtttggatt aattatttcc tattctattg ctgcgggcgt gattgaaggg aaattgattc   1140
cagaattgaa taacaggcta aaaacagtgc aaaatttctt tactagctta tcagctacag   1200
tgaaacaagc gaataaagat atcgatgcgg caaaattgaa attagccact gaaatagcag   1260
cgattgggga gataaaaacg gaaaccgaaa caaccagatt ctacgttgat tatgatgatt   1320
taatgctttc tttattaaaa ggagctgcaa agaaaatgat taacacctgt aatgaatacc   1380
aacaacgtca tggtaagaag acgcttttcg aggttcctga cgtcgctagc ctgatgtctg   1440
attgggaaga tgaagacctg gataccgata tgataacat tccggatagt tatgaacgca   1500
atggttacac catcaaagac ctgattgcgg ttaaatggga agatagcttt gccgaacagg   1560
gctacaaaaa atacgtgagc aactacctgg aatctaacac cgccggtgat ccgtatacgg   1620
attacgaaaa agcaagcggc tcttcgata aagcaattaa aaccgaagcg cgtgatccgc   1680
tggttgcggc ctatccgatc gtgggcgttg gtatggaaaa actgattatc tctaccaacg   1740
aacatgcgag taccgatcag ggtaaaaccg tgagtcgcgc caccacgaat agtaaaaccg   1800
aaagcaacac ggcaggcgtg agcgttaatg tgggctatca gaacggtttt accgcgaatg   1860
ttaccacgaa ctacagccac accacggata attctaccgc cgtgcaggat tctaatggcg   1920
aaagttggaa cacgggtctg agtattaaca aggcgaaag cgcctacatc aacgcaaacg   1980
ttcgttacta caacaccggt acggccccga tgtacaaagt taccccgacc acgaacctgg   2040
tgctggatgg cgatacccctg agcacgatta agcacagga aaaccagatc ggtaataacc   2100
```

```
tgtctccggg cgatacctat ccgaaaaaag gtctgagtcc gctggcgctg aataccatgg      2160
atcagtttag tagccgcctg attccgatca actacgatca gctgaaaaaa ctggatgccg      2220
gcaaacagat taaactggaa accacgcaag ttagcggcaa tttcggtacc aaaaactcta      2280
gtggtcagat cgtgacggaa ggcaatagtt ggagcgatta tattagccag atcgattcta      2340
ttagtgcaag cattatcctg gataccgaaa atgaatctta cgaacgtcgc gtgacggcga      2400
aaaacctgca agatccggaa gataaaaccc cggaactgac gatcggtgaa gccattgaaa      2460
aagcatttgg tgcgaccaaa aaagatggcc tgctgtattt caacgatatt ccgatcgatg      2520
aaagctgcgt tgaactgatc ttcgatgata acaccgcaaa caaaatcaaa gatagtctga      2580
aaacgctgag cgataagaaa atttataacg tgaaactgga acgtggcatg aacattctga      2640
tcaaaacccc gacgtacttc accaacttcg atgattacaa caactacccg agtacgtgga      2700
gcaatgttaa caccacgaac caggatggcc tgcagggtag cgccaacaaa ctgaacggtg      2760
aaaccaaaat caaaatcccg atgtctgaac tgaaaccgta taaacgctac gtgtttctg      2820 gctatagtaa agatccgctg acctctaata gtatcatcgt taaaatcaaa gcgaaagaag      2880
aaaaaaccga ttacctggtg ccggaacagg gttacacgaa attcagttac gaatttgaaa      2940
ccacggaaaa agatagctct aacattgaaa tcaccctgat tggcagcggt accacgtatc      3000
tggataatct gtctattacc gaactgaaca gtacgccgga aatcctggat gaaccggaag      3060
tgaaaatccc gaccgatcag gaaatcatgg atgcccataa aatctatttc gcggatctga      3120
acttcaaccc gagcaccggt aatacgtata ttaacggcat gtactttgca ccgacccaga      3180
cgaataaaga agcgctggat tatattcaga aataccgtgt tgaagccacc ctgcagtata      3240
gcggcttcaa agatatcggt acgaaagata aagaaatgcg taattacctg ggcgatccga      3300
accagccgaa aaccaattat gtgaacctgc gctcttactt taccggcggt gaaaacatca      3360
tgacgtacaa aaaactgcgt atctacgcga ttaccccgga tgatcgcgaa ctgctggttc      3420
tgagtgtgga ttaataacct agctgataac ctagcccgcc taatgagcgg gcttttttt      3480 ctcggcctag g                                                          3491
```

<210> SEQ ID NO 51
<211> LENGTH: 60
<212> TYPE: DNA
<213> ORGANISM: Artificial Sequence
<220> FEATURE:
<223> OTHER INFORMATION: Forward amplification primer

<400> SEQUENCE: 51

```
agatctaaaa taaggaggaa aaaaaaatgg ctagcctgat gtctgattgg gaagatgaag      60
```

<210> SEQ ID NO 52
<211> LENGTH: 43
<212> TYPE: DNA
<213> ORGANISM: Artificial Sequence
<220> FEATURE:
<223> OTHER INFORMATION: Reverse amplification primer

<400> SEQUENCE: 52

```
aagcttccta ggttattaat ccacactcag aaccagcagt tcg                       43
```